US009199962B2

(12) United States Patent
Heinrich et al.

(10) Patent No.: US 9,199,962 B2
(45) Date of Patent: Dec. 1, 2015

(54) SUBSTITUTED AZAHETEROCYCLES FOR THE TREATMENT OF CANCER

(75) Inventors: Timo Heinrich, Gross-Umstadt (DE); Nadia Brugger, Cambridge, MA (US); Kristopher Josephson, Wayland, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/131,309

(22) PCT Filed: Jun. 11, 2012

(86) PCT No.: PCT/EP2012/002469
§ 371 (c)(1),
(2), (4) Date: Apr. 14, 2014

(87) PCT Pub. No.: WO2013/004332
PCT Pub. Date: Jan. 10, 2013

(65) Prior Publication Data
US 2014/0221366 A1  Aug. 7, 2014

Related U.S. Application Data

(60) Provisional application No. 61/505,376, filed on Jul. 7, 2011.

(51) Int. Cl.
*C07D 401/04* (2006.01)
*C07D 401/14* (2006.01)
*A61K 31/444* (2006.01)
*A61K 31/4155* (2006.01)
*C07D 401/12* (2006.01)
*C07D 405/14* (2006.01)
*C07D 413/14* (2006.01)
*C07D 417/14* (2006.01)
*C07D 471/04* (2006.01)
*C07D 473/34* (2006.01)
*A61K 31/506* (2006.01)
*A61K 31/52* (2006.01)
*A61K 31/5377* (2006.01)

(52) U.S. Cl.
CPC .......... *C07D 401/04* (2013.01); *A61K 31/4155* (2013.01); *A61K 31/444* (2013.01); *A61K 31/506* (2013.01); *A61K 31/52* (2013.01); *A61K 31/5377* (2013.01); *C07D 401/12* (2013.01); *C07D 401/14* (2013.01); *C07D 405/14* (2013.01); *C07D 413/14* (2013.01); *C07D 417/14* (2013.01); *C07D 471/04* (2013.01); *C07D 473/34* (2013.01)

(58) Field of Classification Search
CPC .............. C07D 401/04; C07D 401/14; A61K 31/4155; A61K 31/444
USPC ............ 544/122, 295, 328; 514/232.2, 235.8, 514/255.05, 256
See application file for complete search history.

(56) References Cited

U.S. PATENT DOCUMENTS

| | | | |
|---|---|---|---|
| 6,710,048 B2 * | 3/2004 | Kuo et al. | 514/252.11 |
| 6,716,851 B2 * | 4/2004 | Cai et al. | 514/275 |
| 2004/0102455 A1 * | 5/2004 | Burns et al. | 514/255.05 |
| 2005/0049247 A1 * | 3/2005 | Wilson et al. | 514/227.8 |
| 2005/0143387 A1 * | 6/2005 | Marquais-Bienewald et al. | 514/252.14 |
| 2005/0245518 A1 * | 11/2005 | Delorme et al. | 514/235.2 |
| 2009/0048282 A1 | 2/2009 | Hauze | |

FOREIGN PATENT DOCUMENTS

| | | | |
|---|---|---|---|
| EP | 0 640 599 A1 | | 3/1995 |
| JP | 2010-126496 | * | 6/2010 |
| JP | 2010 126496 A | | 6/2010 |
| WO | 96/33972 A1 | | 10/1996 |
| WO | 98/18782 A1 | | 5/1998 |
| WO | 02/47690 A1 | | 6/2002 |
| WO | 02/060492 A1 | | 8/2002 |
| WO | 03/077656 A1 | | 9/2003 |
| WO | 2004/106296 A2 | | 12/2004 |
| WO | 2005/003099 A2 | | 1/2005 |
| WO | 2007/008541 A2 | | 1/2007 |
| WO | 2008/113255 A1 | | 9/2008 |
| WO | 2008/116139 A2 | | 9/2008 |
| WO | 2009/027736 A2 | | 3/2009 |
| WO | 2009/039542 A2 | | 4/2009 |
| WO | 2010/090290 A1 | | 8/2010 |
| WO | 2010/126922 A1 | | 11/2010 |
| WO | 2010/141406 A2 | | 12/2010 |
| WO | WO 2013/066839 | * | 5/2013 |

OTHER PUBLICATIONS

Ahlstroem et al., Characterization of Type II Ligands in CYP2C9 and CYP3A4, J. Med. Chem., 51, pp. 1755-1763 (2008).*
El-Deeb et al., Synthesis of New N-Arylpyrimidin-2-amine Derivatives using a palladium catalyst, Molecules, 13, pp. 818-830 (2008).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, 20th Edition, vol. 1, pp. 1004-101 O, 1996.*

(Continued)

Primary Examiner — Deepak Rao
(74) Attorney, Agent, or Firm — Dwight D. Kim; EMD Serono Research and Development Institute

(57) ABSTRACT

The invention provides novel substituted azaheterocyclic compounds according to Formula (I), their manufacture and use for the treatment of hyperproliferative diseases, such as cancer.

21 Claims, No Drawings

(56) References Cited

OTHER PUBLICATIONS

Mclean et al., The Role of Focal-Adhesion Kinase in Cancer—A New Therapeutic Opportunity, 2005, Nat Rev Cancer, 5:505-515.
Owens et al., Overexpression of the Focal Adhesion Kinase (p125FAK) in Invasive Human Tumors, 1995, Cancer Research, 55: 2752-2755.
Agochiya et al., Increased dosage and amplification of the focal adhesion kinase gene in human cancer cells,1999, Oncogene, 18:5646-5653.
Gabarro-Niecko et al., FAK regulates biological processes important for the pathogenesis of cancer, 2003, Cancer Metastasis Rev., 22:359-374.
Recher et al., Expression of Focal Adhesion Kinase in Acute Myeloid Leukemia is Associated with Enhanced Blast Migration, Increased Cellularity, and Poor Prognosis, 2004, Cancer Research, 64:3191-3197.
Grisaru-Granovsky et al., Differential Expression of Protease Activated Receptor1(Par1) and pY397FAK in Benign and Malignant Human Ovarian Tissue Samples, 2005, Int. J. Cancer, 113: 372-378.
Beviglia et al., Focal adhesion kinase N-terminus in breast carcinoma cells induces rounding,detachment and apoptosis, 2003, Biochem J., 373:201-210.
Smith et al., Effect of focal adhesion kinase (FAK) downregulation with FAK antisense oligonucleotides and 5-fluorouracil on the viability of melanoma cell lines, 2005, Melanoma Res., 15:357-362.
Halder et al., Focal Adhesion Kinase Silencing Augments Docetaxel-Mediated Apoptosis in Ovarian Cancer Cells, 2005, Clin. Cancer Res., 11:8829-8836.
Xu et al., Attenuation of the expression of the focal adhesion kinase induces apoptosis in tumor cells, 1996, Cell Growth and Diff, 7:413-418.
Van Nimwegan et al., Requirement for Focal Adhesion Kinase in the Early Phase of Mammary Adenocarcinoma Lung Metastasis Formation, 2005, Cancer Res., 65:4698-4706.
Mitra et al., Intrinsic focal adhesion kinase activity controls orthotopic breast carcinoma metastasis via the regulation of urokinase plasminogen activator expression in a syngeneic tumor model, 2006, Oncogene, 25:4429-4440.
Mitra et al., Intrinsic FAK activity and Y925 phosphorylation facilitate an angiogenic switch in tumors 2006, Oncogene, 25:5969-5984.
El-Deeb, et al., Design and synthesis of new anticancer pyrimidines with multiple-kinase inhibitory effect, 2010, Bioorganic & Medicinal Chemistry, 18(11):3860-3874.
Zhao et al., Signal transduction by focal adhesion kinase in cancer, 2009, Cancer Metastasis Rev., 28:35-49.
Wu Yang et al., Discovery and Structure-Activity Relationships of Trisubstituted Pyrimidines/Pyridinesas Novel Calcium-Sensing ReceptorAntagonists, 2009, Journal of Medicinal Chemistry. vol. 52:1204-1208.
Zhou et al., Discovery of N-(2-Aminophenyl)-4-[(4-pyridin-3-ylpyrimidin-2-ylamino)methyl]benzamide(MGCD0103), an Orally Active Histone Deacetylase Inhibitor, 2008, Journal of Medicinal Chemistry, vol. 51 (14):4072-4075.
Ahlstrom et al., Characterization of TypeII Ligands in CYP2C9 and CYP3A4, 2008, J.Med.Chem., vol. 51 (6):1755-1763.

\* cited by examiner

SUBSTITUTED AZAHETEROCYCLES FOR THE TREATMENT OF CANCER

RELATED APPLICATIONS

This application is a U.S. national stage application of PCT international application PCT/EP2012/002469, filed on Jun. 11, 2012, which claims the benefit of U.S. provisional application U.S. Ser. No. 61/505,376, filed on Jul. 7, 2011. The entire contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Apr. 13, 2015, is named P11-110US-PCT_SL.txt and is 934 bytes in size.

FIELD OF THE INVENTION

The invention relates to a series of novel substituted azaheterocyclic compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Tyrosine kinases play an important role in the regulation of many cell processes including cell proliferation, cell survival, and cell migration. It is known that certain tyrosine kinases become activated by mutation or are abnormally expressed in many human cancers. For example, the epidermal growth factor receptor (EGFR) is found mutated and/or overexpressed in breast, lung, brain, squamous cell, gastric, and other human cancers. Selective inhibitors of the tyrosine kinase activity of EGFR have been shown to be of clinical value in treatment of cancers with mutated and/or overexpressed EGFR. Thus, selective inhibitors of particular tyrosine kinases are useful in the treatment of proliferative diseases such as cancer.

FAK (encoded by the gene PTK2) is a non-receptor tyrosine kinase that integrates signals from integrins and growth factor receptors. FAK has been reported to play a role in the regulation of cell survival, growth, adhesion, migration, and invasion (McLean et al 2005, Nat Rev Cancer 5:505-515). Furthermore, FAK is regulated and activated by phosphorylation on multiple tyrosine residues. Overexpression of FAK mRNA and/or protein has been documented in many solid human tumors, including but not limited to, cancers of the breast, colon, thyroid, lung, ovary, and prostate; but also including cancers of hematological origin, including but not limited to leukemia such as acute myeloid leukemia (AML). (Owens et al. 1995, Cancer Research 55: 2752-2755; Agochiya et al. 1999, Oncogene 18: 5646-5653; Gabarro-Niecko et al. 2003, Cancer Metastasis Rev. 22:359-374; Recher et al. 2004, Cancer Research 64:3191-3197; Zhao and Guan, 2009. Cancer Metastasis Rev.). More significantly, there is evidence that phosphorylated FAK is increased in malignant compared to normal tissues (Grisaru-Granovsky et al. 2005, Int. J. Cancer 113: 372-378) and could represent a prognostic marker of metastasis. FAK activity is clearly implicated in advanced and metastatic human cancer.

Inhibition of FAK by RNAi or expression of a FAK dominant negative has been shown to induce loss of adhesion and cell death in human breast and melanoma cell lines, and to augment docetaxel-mediated apoptosis in ovarian cancer cells (Beviglia et al 2003, Biochem J. 373:201-210, Smith et al 2005, Melanoma Res. 15:357-362, Haider et al 2005, Clin. Cancer Res. 11:8829-8836). However, inhibition of FAK in normal human fibroblasts or immortalized mammary cells (MCFIOA) was found not to cause loss of attachment or apoptosis (Xu et al. 1996 Cell Growth and Diff 7:413-418). Inhibition of FAK by dominant negative expression has also been shown to reduce tumor growth and eliminate lung metastasis of mammary adenocarcinoma cells in a syngeneic rat model (van Nimwegen et al 2005, Cancer Res. 65:4698-4706). Similarly, inhibition of FAK by shRNA inhibited lung metastasis and reduced lethality by 40% in a syngeneic mouse model (Mitra et al 2006, Oncogene 25: 4429-4440). In this study, transient re-expression of wild-type, but not kinase-dead FAK, reversed the shRNA phenotypes. Inhibition of FAK by dominant negative expression in mouse 4TI carcinoma cells reduced tumor growth and angiogenesis in mice (Mitra et al 2006, Oncogene 25:5969-5984). Furthermore, loss of FAK catalytic activity (reconstitution of FAK−/− cells with kinase-dead FAK) reduced growth of v-Src tumors in mice and decreased angiogenesis.

Thus, there is strong evidence to suggest that inhibition of FAK activity induces, for example, apoptosis, loss of adhesion, inhibition of cell growth and migration, and that such inhibition reduces angiogenesis. Accordingly, compounds that inhibit FAK activity would be useful for the treatment of cancer.

Compounds described as suitable for FAK inhibition are disclosed in, i.a. WO 08/116,139, WO 09/039,542 and WO 10/126,922.

DESCRIPTION OF THE INVENTION

It is the object of the present invention to provide novel FAK inhibitors useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel substituted azaheterocyclic compounds and pharmaceutically acceptable salts, solvates or prodrugs thereof, that are kinase inhibitors and useful in the treatment of the above mentioned diseases.

The compounds are defined by Formula (I):

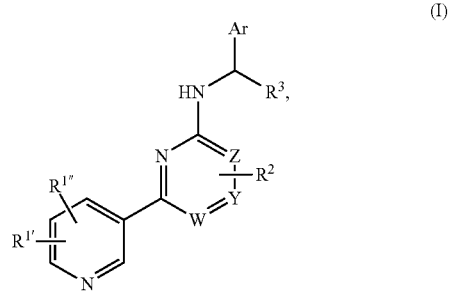

wherein:
$R^{1'}$, $R^{1'''}$ are independently H, A, Hal, Cyc, CO(Cyc),
$R^2$ is H, A, $Q^1$-(C(LA)H)$_n$-$Q^2$, Cyc, $R^3$ is H, A, -LA-Cyc A is unbranched or branched linear or cyclic alkyl having 1, 2, 3, 4 or 5 C atoms, in which one CH$_2$ group may be replaced by an O or S atom and/or by an —NH—, —CO—, —NH-COO—, —NHCONH—, —CONH—, —NHCO—, —CH=CH—, —N=CH— or —CH=N— group, and in which 1-5 H atoms may be replaced by Hal, and in which one CH group may be replaced by N, and in which one CH$_3$ group may be replaced by CN, Hal is F, Cl, Br or I, Cyc is a monocyclic, non-aromatic or aromatic, homo- or heterocycle having 0, 1 or 2, N, O and/or S atoms and 4, 5 or 6 skeleton atoms, which may be unsubstituted or, independently of one another, mono- or disubstituted by Hal, LA, OH, carbonyl oxygen, SH, O(LA), NH$_2$, NH(LA), N(LA)$_2$, NO$_2$, CN, OCN, SCN, COOH, COO(LA), CONH$_2$, CONH(LA), CON(LA)$_2$, NHCO(LA), NHCONH(LA), NHCONH$_2$, NHSO$_2$(LA), CHO, CO(LA), SO$_2$NH$_2$, SO$_2$(LA) and/or SO$_2$Hal, $Q^1$ —NH—, —O—, —COO—, —CONH—, or a bond, $Q^2$ NH$_2$, NH(LA), N(LA)$_2$, CONH$_2$, CONH(LA), CON(LA)$_2$, COOH, COO(LA), Cyc, CO(Cyc), n 0, 1, 2, 3 or 4, Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono-, di- or trisubstituted by Hal, A, OH, SH, OA, NH$_2$, NHA, NA$_2$, NO$_2$, CN, OCN, SCN, COOH, COOA, CONH$_2$, CONHA, CONA$_2$, NHCOA, NHCONHA, NHCONH$_2$, NHSO$_2$A, CHO, COA, SO$_2$NH$_2$, SO$_2$A, SO$_2$Hal and/or (X)$_m$—Cyc, and in which a ring N-atom may be substituted by an O-atom to form an N-oxide group, and in which in the case of a bicyclic ring system one ring may be aromatic, and the other ring non-aromatic,

X CH$_2$, NH, O,

W, Y, Z are CH or N, wherein at least two of W, Y, Z are CH, m 0 or 1, and

LA is H, or unbranched or branched, linear alkyl having 1, 2 or 3 or 4 C atoms, wherein 1, 2 or 3 H atoms may be replaced by Hal.

In general, all residues which occur more than once may be identical or different, i.e. are independent of one another. Above and below, the residues and parameters have the meanings indicated for the Formula (I), unless expressly indicated otherwise. Accordingly, the invention relates, in particular, to the compounds of the Formula (I) in which at least one of the said residues has one of the preferred meanings indicated below.

Hal denotes fluorine, chlorine, bromine or iodine, in particular fluorine or chlorine.

"A" denotes, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, or 1-ethylpropyl.

"A" further denotes alkyl as defined above, in which one CH$_2$ group may be replaced by O or S atoms and/or an —NH—, —CO—, —NHCOO—, —NHCONH—, —CONH—, —NHCO—, —CH=CH—, —N=CH— or —CH=N— group, and in which 1-5 H atoms may be replaced by Hal, and in which one CH group may be replaced by N, and in which one CH$_2$ group may be replaced by CN, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy, N,N'-dimethylaminoalkyl, 2-aminoethyl, 3-aminopropyl, 4-aminobutyl, 5-aminopentyl, 3-aminomethylcyclobutyl or cyanoalkyl.

Cyclic A preferably denotes cyclopropyl, cyclobutyl, cyclopentyl, cyclohexyl or cycloheptyl.

"LA" denotes H, or unbranched or branched, linear alkyl having 1, 2, 3 or 4 C atoms, wherein 1, 2 or 3 H atoms may be replaced by Hal, e.g. methyl, ethyl, trifluoromethyl, difluoromethyl, 1,1,1-trifluoroethyl, propyl, isopropyl, butyl, isobutyl, sec-butyl or tert-butyl.

"Ar" denotes, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

"Ar" furthermore denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methyl-amino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl) phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methyl-sulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxy-phenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4, 6- or 3,4,5-tri-chlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl, (4-methoxyphenyl)methyl, (3-methoxyphenyl)methyl, (4-methoxyphenyl)ethyl, (3-methoxyphenyl)ethyl.

"Ar" furthermore preferably denotes phenyl, 2-, 3- or 4-phenylmethyl, 2-, 3- or 4-phenylethyl, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 3- or 4-pyridylmethyl, 2-, 3- or 4-pyridylethyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3,4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6-, or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, further preferably 1,3-benzodioxol-2-, 4- or 5-yl, thiophen-2- or 3-yl, 1,4-benzodioxan-6-yl, 2,1,3-benzothiadiazol-4- or 5-yl or 2,1,3-benzoxadiazol-5-yl, furan-2- or 3-yl, 2,3-dihydro-benzofuran-2-, 3-, 4- or 5-yl, chromane-2-, 3-, 4-, 5-, 6-, 7- or 8-yl, isoindolin-1-one-2-, 3-, 4-, 5-, or 6-yl, pyrazolo[1,5-a]pyridin-2-, 3-, 4-, 5-, 6- or 7-yl, 2,3-dihydro-benzofuran-3-, 4-, 5-, 6- or 7-yl, 2,3-dihydro-benzo[1,4]dioxin-2-, 3-, 5- or 6-yl, each of which is unsubstituted or may be mono-, di- or trisubstituted, for example, by carbonyl oxygen, F, Cl, Br, methyl, methoxy, ethyl, propyl, phenyl, benzyl, —CH$_2$-cyclohexyl, hydroxyl, methoxy, trifluoromethyl, trifluoromethoxy, N-methyl methanesulfonamidyl, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

"Cyc" denotes, for example, cyclobutyl, cyclopentyl, cyclohexyl, azetidine-1-, 2- or 3-yl, oxetane-2- or 3-yl, thietane-2- or 3-yl, oxazolidine-2-, 3-, 4- or 5-yl, isoxazolidine-2-, 3-, 4- or 5-yl, thiazolidine-2-, 3-, 4- or 5-yl, isothiazolidine-2-, 3-, 4- or 5-yl, dioxolane-2- or 4-yl, dithiolane-3- or 4-yl, thiane-2-, 3-, or 4-yl, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3-, 1-, 5- or 6-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, phenyl, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 2-, 3-, 5-, or 6-pyrazin-1- or 4-yl, 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3,4-thiadiazol-2- or -5-yl, 1,2,4-thiadiazol-3- or -5-yl, 1,2,3-thiadiazol-4- or -5-yl, each of which is unsubstituted or may be mono-, di- or trisubstituted, for example, by carbonyl oxygen, F, Cl, Br, methyl, ethyl, propyl, phenyl, benzyl, —CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

"LA" denotes, e.g., methyl, ethyl, propyl, isopropyl, butyl, isobutyl, sec-butyl, tert-butyl, trifluoromethyl, pentafluoroethyl, 1,1-difluoromethyl or 1,1,1-trifluoroethyl.

The term "substituted" preferably relates to the substitution by the above-mentioned substituents, where a plurality of different degrees of substitution are possible, unless indicated otherwise.

A preferred group of compounds of Formula (I) conform to Formulae (II), (III), (IV) or (V),

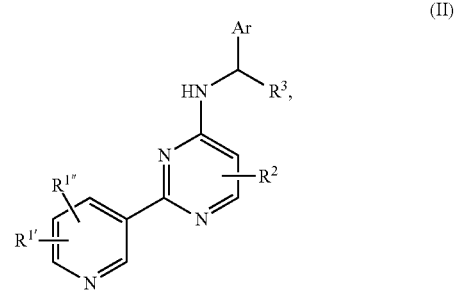

(II)

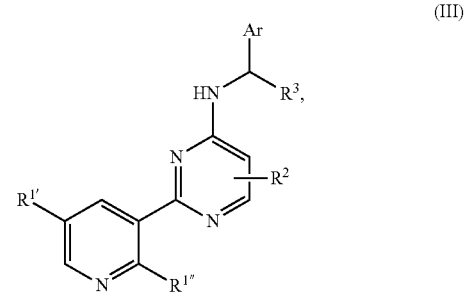

(III)

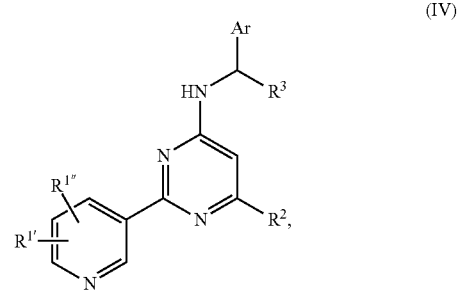

(IV)

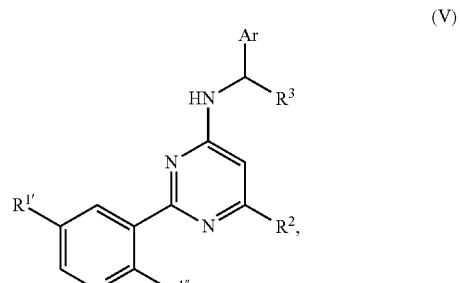

(V)

in which all residues have the meaning indicated for Formula (I).

Further preferred are compounds of Subformulae 1 to 16 of Formulae (I), (II), (III), (IV) or (V), in which the residues not designated in greater detail have the meaning indicated for the Formulae above, wherein in Subformula 1

Ar is phenyl, pyridyl, 2,1,3-benzothiadiazolyl, 1,3-benzodioxolyl, pyrazolo[1,5-a]pyridyl, pyrimidyl, morpholinyl, 2,3-dihydro-benzofuranyl, pyrazolyl, all of which may be unsubstituted, or mono- or disubstituted by Hal, LA, OH, SH, O(LA), NH$_2$, NH(LA), N(LA)$_2$, NO$_2$, CN, OCN, SCN, COOH, COO(LA), CONH$_2$, CONH(LA), CON(LA)$_2$, NHCO(LA), NHCONH(LA), NHCONH$_2$, NHSO$_2$(LA), CHO, CO(LA), SO$_2$NH$_2$, SO$_2$(LA), SO$_2$Hal, (X)$_m$-Cyc in Subformula 2
$R^3$ is H,
in Subformula 3
$R^{1'}$ is H, Hal, LA, O(LA), CO(Cyc),
$R^{1'''}$ is H, $NH_2$,
in Subformula 4
$R^2$ is H,
in Subformula 5
$R^2$ is $Q^1$-(C(LA)H)$_n$-$Q^2$,
in Subformula 6
Ar is phenyl which is, independently, mono- or disubstituted by Hal, LA, OH, SH, O(LA), $NH_2$, NH(LA), $N(LA)_2$, $NO_2$, CN, OCN, SCN, COOH, COO(LA), $CONH_2$, CONH(LA), $CON(LA)_2$, NHCO(LA), NHCONH(LA), $NHCONH_2$, $NHSO_2$(LA), CHO, CO(LA), $SO_2NH_2$, $SO_2$(LA), $SO_2$Hal, Cyc, O-Cyc,
in Subformula 7
Ar is phenyl or pyridyl, which is, independently, mono- or disubstituted in ortho and/or para position by Hal, LA, OH, O(LA), $NH_2$, NH(LA), $N(LA)_2$, $NHSO_2$(LA), CO(LA), $SO_2NH_2$, $SO_2$(LA), $SO_2$Hal,
in Subformula 8
Ar is phenyl which is, independently, mono- or disubstituted in ortho and/or para position by F, Cl, methyl, or $CF_3$,
in Subformula 9
$R^2$ is H,
$R^3$ is H,
in Subformula 10
$R^{1'}$ is H, Hal, LA, O(LA), CO(Cyc),
$R^{1'''}$ is H, $NH_2$,
$R^2$ is H,
$R^3$ is H,
in Subformula 11
Ar is phenyl or pyridyl, which is, independently, mono- or disubstituted in ortho and/or para position by Hal, LA, OH, O(LA), $NH_2$, NH(LA), $N(LA)_2$, $NHSO_2$(LA), CO(LA), $SO_2NH_2$, $SO_2$(LA), $SO_2$Hal,
$R^{1'}$ is H, Hal, LA, O(LA), CO(Cyc),
$R^{1'''}$ is H, $NH_2$,
$R^2$ is H,
$R^3$ is H,
in Subformula 12
$R^2$ is $Q^1$-(CH$_2$)$_n$-$Q^2$,
in Subformula 13
$R^{1'}$ is H, Hal, LA, O(LA), CO(Cyc),
$R^{1'''}$ is H, $NH_2$,
$R^2$ is $Q^1$-(CH$_2$)$_n$-$Q^2$,
in Subformula 14
$R^{1'}$ is H, Hal, LA, O(LA), CO(Cyc),
$R^{1'''}$ is H, $NH_2$,
$R^2$ is $Q^1$-(CH$_2$)$_n$-$Q^2$,
$R^3$ is H,
in Subformula 15
Ar is phenyl or pyridyl, which is, independently, mono- or disubstituted in ortho and/or para position by Hal, LA, OH, O(LA), $NH_2$, NH(LA), $N(LA)_2$, $NHSO_2$(LA), CO(LA), $SO_2NH_2$, $SO_2$(LA), $SO_2$Hal,
$R^{1'}$ is H, Hal, LA, O(LA), CO(Cyc),
$R^{1'''}$ is H, $NH_2$,
$R^2$ is $Q^1$-(CH$_2$)$_n$-$Q^2$,
$R^3$ is H,
in Subformula 16
Ar is phenyl which is disubstituted in ortho and para position by F,
$R^{1'}$ is $CF_3$,
$R^{1'''}$ is H,
$R^2$ is $Q^1$-(CH$_2$)$_n$-$Q^2$,
$R^3$ is H,
and the remaining residues have the meaning as indicated for Formula (I) above.

The compounds of the Formula (I) may have one or more centres of chirality. They may accordingly occur in various enantiomeric forms and be in racemic or optically active form. The invention, therefore, also relates to the optically active forms, enantiomers, racemates, diastereomers, collectively: stereoisomers, of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

It is well known that atoms may have atomic masses or mass numbers which differ from the atomic masses or mass numbers of the atoms which usually occur naturally. Examples of isotopes which are readily commercially available and which can be incorporated into a compound of the present invention by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Incorporation of heavier isotopes, especially deuterium ($^2H$), into a compound of the invention has therapeutic advantages owing to the higher metabolic stability of this isotope-labelled compound. Higher metabolic stability translates directly into an increased in vivo half-life or lower dosages. Therefore, these isotopes are included in the definition of atoms H, C, N etc., as used in the chemical compounds of this invention.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like.

If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt, a solvate, or a solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherare, e.g., diethyl etherate.

Therefore, the following items are also in accordance with the invention:

a) all stereoisomers or tautomers of the compounds, including mixtures thereof in all ratios,
b) prodrugs of the compounds, or stereoisomers or tautomers of these prodrugs,
c) pharmaceutically acceptable salts of the compounds and of the items mentioned under (a) and (b),
d) solvates of the compounds and of the items mentioned under (a), (b) and (c).

It should be understood that all references to compounds include these items, in particular solvates of the compounds or solvates of their pharmaceutically acceptable salts.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other FAK inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast, colon, lung, prostate, stomach, pancreatic, ovarian, skin (melanoma), endocrine, uterine, testicular, bladder. or glioblastoma.

The invention also relates to the use of a compound according to the invention for the preparation of a medicament for the treatment of hyperproliferative diseases related to the hyperactivity of FAK as well as diseases modulated by the FAK cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, and a pharmaceutically acceptable carrier.

In one embodiment, said compound or pharmaceutical composition is for treating a disease selected from the group consisting of hyperproliferative diseases, such as tumor angiogenesis and cancer but also chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, in combination with an amount of another anti-cancer therapeutic, wherein the amounts of the compound, and of the other anti-cancer therapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention or pharmaceutical composition, in combination with radiation therapy, wherein the amounts of the compound or pharmaceutical composition, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention, or pharmaceutical composition, in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutical composition, which amount is effective is sensitizing abnormal cells to treatment with radiation. The amount of the compound in this method can be determined according to the means for ascertaining effective amounts of such compounds described herein.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of a) an effective amount of a compound according to the invention or its stereoisomers or tautomers, or pharmaceutically acceptable salts of each of the foregoing, including mixtures thereof in all ratios, and b) an effective amount of a further medicament active ingredient.

The set comprises suitable containers, such as boxes, individual bottles, bags or ampoules.

By way of example, the set may comprise separate ampoules, each containing an effective amount of a compound according to the invention, and an effective amount of a further medicament active ingredient in dissolved or lyophilised form.

EXPERIMENTAL SECTION

Some abbreviations that may appear in this application are as follows:

| Abbreviations | |
|---|---|
| Designation | |
| ACN | acetonitrile |
| ATP | Adenosine triphosphate |
| br. | Broad peak |
| d | Doublet |
| DMSO | dimethylsulfoxide |
| DIEA | N,N-Diisopropylethylamine |
| DTT | dithiothreitol |
| EDTA | Ethylenediaminetetraacetic acid |
| equiv. | equivalents |
| Et | ethyl |
| h | hour |

-continued

| Abbreviations | |
|---|---|
| Designation | |
| HEPES | 4-(2-hydroxyethyl)-1-piperazineethanesulfonic acid |
| HPLC | High pressure liquid chromatography |
| Hz | Hertz |
| J | Coupling constant |
| LC/MS | Liquid chromatography coupled to mass spectrometry |
| m | multiplet |
| M | Molecular ion |
| m/z | Mass-to-charge ratio |
| Me | methyl |
| min | minute |
| MS | Mass spectrometry |
| N | Normal (unit of concentration) |
| NMO | 4-methylmorpholine N-oxide |
| NMR | Nuclear Magnetic Resonance |
| PG | Protecting group |
| psi | Pounds per square inch |
| q | Quartette (or quartet) |
| Rf | Retention factor |
| RT | Room temperature |
| Rt. | Retention time |
| s | Singlet |
| t | Triplet |
| Tert | Tertiary |
| TEA | Triethylamine |
| TFA | Trifluoroacetic acid |
| THAB | Tetrahexylammonium bromide |
| THF | Tetrahydrofuran |
| TLC | Thin Layer Chromatography |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above.

Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

General Synthetic Procedures

The present invention also relates to processes for manufacturing the compounds of Formulae (I), (II), (III), (IV) or (V), and Subformulae 1-16 according to the hereinafter described schemes and working examples.

Scheme 1

In accordance with general Scheme 1, the present invention relates to a process for the manufacture of compounds of Formula (I), wherein a substituted azaheterocycle according to Formula (X)

is reacted with an aryl amine according to Formula (IX)

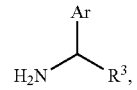

to yield an intermediate according to Formula (VIII)

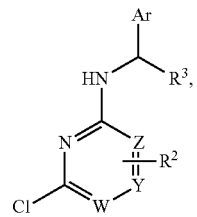

which is then reacted with a boronic acid or ester substituted pyridine according to Formula (VII)

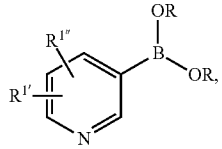

to yield a product according to Formula (I), wherein R is H, LA (as defined above, such as methyl or isopropyl), or an alkyl chain, linking the boronic acid oxygen atoms, such as 1,1,2,2-tetramethylethyl (yielding boronic acid pinacol ester), and all other substituents have the meaning as defined for Formula (I).

Scheme 2 shows a general example for the synthesis of amido substituted azaheterocyclic compounds according to the invention:

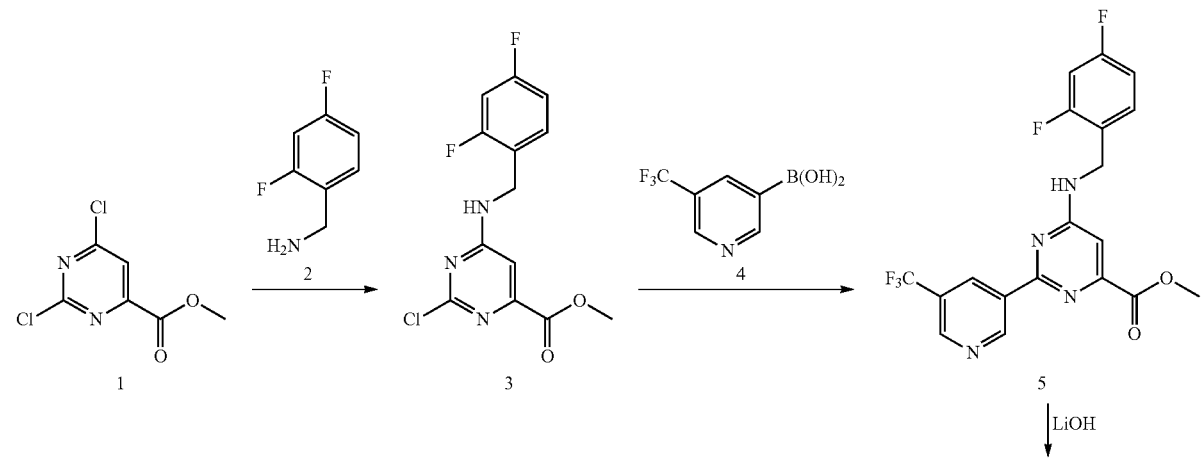

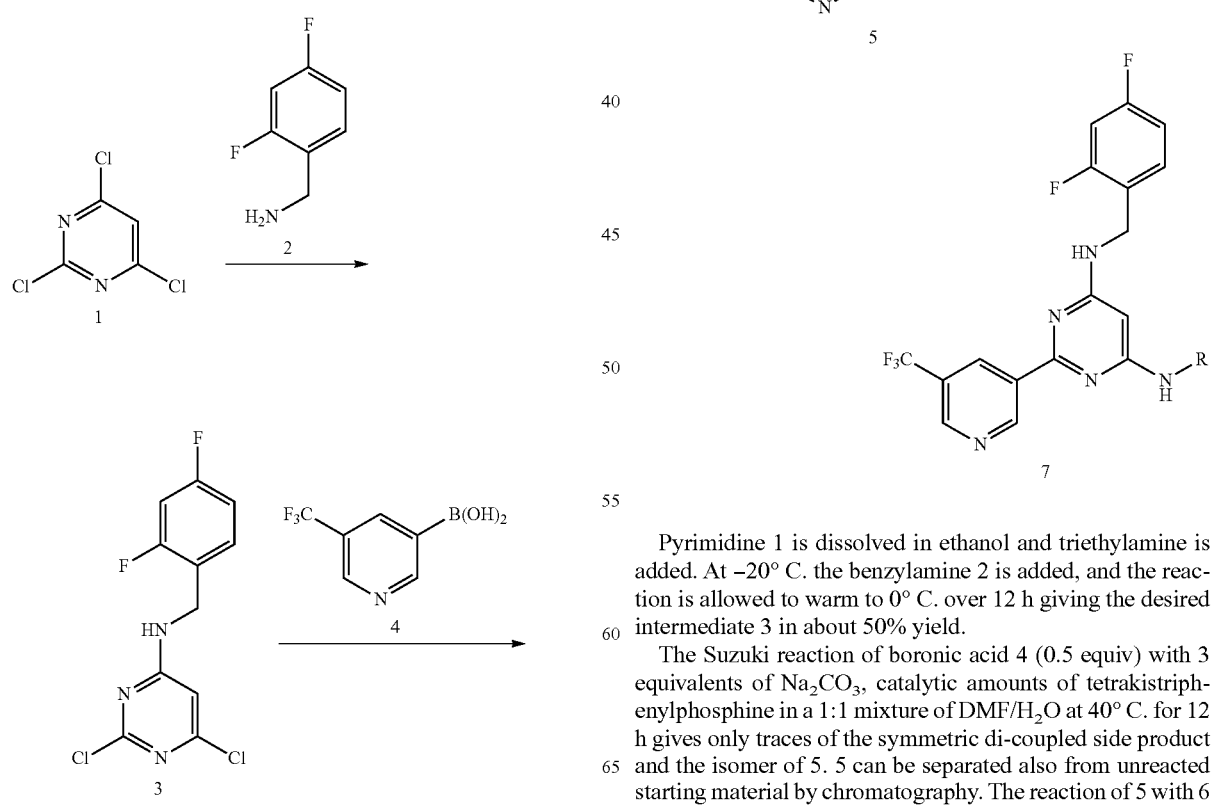

Methyl 2,6-dichloropyrimidine-4-carboxylate 1 is reacted from −20° C. to 0° C. in methanol and triethylamine with benzylamine to intermediate 3. 3 is then coupled with boronic acid 4 under microwave conditions and palladium catalysis to yield ester 5. Adding lithium hydroxide in methanol/water gives the free acid 6, which is finally coupled with an amine 7 in dichloromethane to yield the amides 8 according to Formula (I).

Scheme 3 shows a general example for the synthesis of amino substituted azaheterocyclic compounds according to the invention:

Pyrimidine 1 is dissolved in ethanol and triethylamine is added. At −20° C. the benzylamine 2 is added, and the reaction is allowed to warm to 0° C. over 12 h giving the desired intermediate 3 in about 50% yield.

The Suzuki reaction of boronic acid 4 (0.5 equiv) with 3 equivalents of Na$_2$CO$_3$, catalytic amounts of tetrakistriphenylphosphine in a 1:1 mixture of DMF/H$_2$O at 40° C. for 12 h gives only traces of the symmetric di-coupled side product and the isomer of 5. 5 can be separated also from unreacted starting material by chromatography. The reaction of 5 with 6 to 7 can be done under various conditions, either simple heating of the reactants up to 120° C., either neat or in a solvent like DMF, or by palladium catalysis in solvents like toluene.

Analytical Methodology

Compound numbers 1-55 and 148-273 were all purified and characterized using the following methods:

LCMS

Method: A—0.1% TFA in water, B—0.1% TFA in ACN; Flow rate: 2 ml/min.

Column: XBridge C8 (50×4.6 mm, 3.5μ)

HPLC

Method: A—0.1% TFA in water, B—0.1% TFA in ACN; Flow rate: 2 ml/min

Column: XBridge C8 (50×4.6 mm, 3.5μ)

Compound numbers 77-125, 127-137 and 139-145 were characterized using the following method:

Column: Xterra 2.1×30 3.5 um

Flow: 400 uL/min

Temp: room temp

Solvent A: Water+0.1% TFA

Solvent B: Acetonitrile+0.1% TFA

Gradient: 15-95% B in 3.2 minutes, hold at 95% for 1.4 min

Runtime: 7 minutes

Wavelength: 254 nm

Mass Range: 100-900 Dalton

Compound number 126 was characterized using the following method:

Column: Xbridge C8, 4.6×50 mm 5 um

Mobile Phase A: Water+0.1% TFA

Mobile Phase B: ACN+0.1% TFA

Gradient: 2-100% B in 8 minutes

Flow: 2 mL/min

Wavelength 254 nm

Mass Scan: 100-900 Da

Compound number 138, 146 and 147 were characterized using the following method:

Column: Xbridge C18, 4.6×50 mm 5 um

Mobile Phase A: Water+0.1% TFA

Mobile Phase B: ACN+0.1% TFA

Gradient: 5-95% B in 3.5 minutes

Flow: 0.8 mL/min

Wavelength 254 nm

Mass Scan: 100-900 Da

EXAMPLES

The working examples presented below are intended to illustrate particular embodiments of the invention, and are not intended to limit the scope of the specification or the claims in any way.

Chemical Synthesis

In this section experimental details are provided for a number of Example compounds according to Formula (I), and synthesis intermediates thereof.

Synthesis Intermediates for Azaheterocyclic Compounds where $R^2$ is H:

General Protocol:

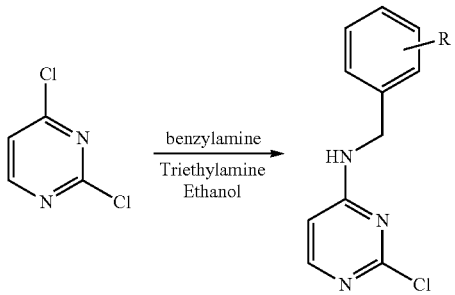

A suspension of 2,4-dichloropyrimidine (1 eq) in ethanol (20 vol) was cooled to −20° C. To this suspension benzylamine (0.9 eq) and triethylamine (1.5 eq) were added. The reaction mixture was stirred at same temperature for 1 hr then at room temperature for 4 hrs. Ethanol was removed under vacuum. The residue was purified by column chromatography to get the compound.

(2-Chloro-pyrimidin-4-yl)-(2,3-difluoro-4-methoxy-benzyl)-amine

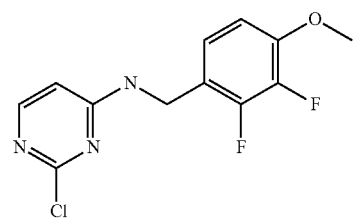 [SMILES: COc1ccc(CNc2ccnc(Cl)n2)c(F)c1F]

Yield: 49.72%

TLC: Petrol ether/Ethyl acetate (7/3): $R_f$: 0.4

LCMS: Mass found (+MS, 286)

Method: A—0.1% TFA in water, B—0.1% TFA in ACN; Flow rate: 2 ml/min.

Column: XBridge C8 (50×4.6 mm, 3.5μ)

Rt (min): 3.56 Area %: 99.03 (at max), 99.45 (at 254 nm).

HPLC: >99%

Method: A—0.1% TFA in water, B—0.1% TFA in ACN; Flow rate: 2 ml/min

Column: XBridge C8 (50×4.6 mm, 3.5μ)

Rt (min): 3.58 Area %: 99.58 (at max), 99.83 (at 254 nm).

$^1$H NMR (400 MHz, DMSO-d6): δ 8.36 (brs, 1H), 8.25-7.93 (m, 1H), 7.15-7.11 (m, 1H), 7.02-6.97 (m, 1H), 6.50 (d, J=5.96 Hz, 1H), 4.48-4.41 (m, 2H), 3.84 (s, 3H).

(2-Chloro-pyrimidin-4-yl)-[4-(4-fluoro-phenoxy)-benzyl]amine

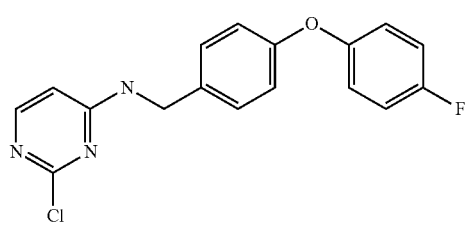 [SMILES: Fc1ccc(Oc2ccc(CNc3ccnc(Cl)n3)cc2)cc1]

Yield: 54.14%
TLC: Pet ether/Ethyl acetate (7/3): $R_f$: 0.3
LCMS: Mass found (+MS, 330)
Method: A—0.1% TFA in water, B—0.1% TFA in ACN; Flow rate: 2 ml/min.
Column: XBridge C8 (50×4.6 mm, 3.5μ)
Rt (min): 4.63 Area %: 98.73 (at max), 98.10 (at 254 nm).
HPLC: >98%
Method: A—0.1% TFA in water, B—0.1% TFA in ACN; Flow rate: 2 ml/min
Column: XBridge C8 (50×4.6 mm, 3.5μ)
Rt (min): 4.55 Area %: 98.42 (at max), 98.04 (at 254 nm).
$^1$H NMR (400 MHz, DMSO-d6): δ 8.49-8.35 (m, 1H), 8.05-7.91 (m, 1H), 7.34-7.30 (m, 2H), 7.24-7.18 (m, 2H), 7.06-7.00 (m, 2H), 6.96 (d, J=8.52 Hz, 2H), 6.49 (d, J=5.84 Hz, 1H), 4.47-4.45 (m, 2H).

(4-Chloro-2-fluoro-benzyl)-(2-chloro-pyrimidin-4-yl)-amine

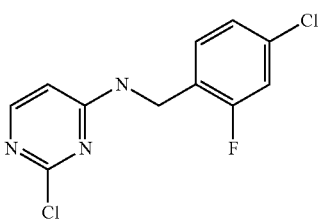 [SMILES: Fc1cc(Cl)ccc1CNc1ccnc(Cl)n1]

Yield: 43.60%
TLC: Pet ether/Ethyl acetate (7/3): $R_f$: 0.4
LCMS: Mass found (+MS, 272)
Method: A—0.1% TFA in water, B—0.1% TFA in ACN; Flow rate: 2 ml/min.
Column: XBridge C8 (50×4.6 mm, 3.5μ)
Rt (min): 3.93 Area %: 98.20 (at max), 99.01 (at 254 nm).
HPLC: >99%
Method: A—0.1% TFA in water, B—0.1% TFA in ACN; Flow rate: 2 ml/min
Column: XBridge C8 (50×4.6 mm, 3.5μ)
Rt (min): 3.81 Area %: 99.30 (at max), 99.25 (at 254 nm).
$^1$H NMR (400 MHz, DMSO-d6): δ 8.39 (t, J=5.36 Hz, 1H), 7.94 (d, J=5.56 Hz, 1H), 7.44 (dd, J=10.04, 2.04 Hz, 1H), 7.40-7.36 (m, 1H), 7.27 (dd, J=8.28, 1.88 Hz, 1H), 6.52 (d, J=5.80 Hz, 1H), 4.50 (d, J=4.88 Hz, 2H).

(2-Chloro-pyrimidin-4-yl)-(2,2-dimethyl-2,3-dihydro-benzofuran-7-ylmethyl)-amine

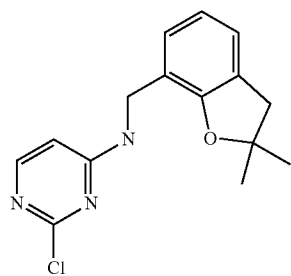 [SMILES: CC1(C)Cc2cccc(CNc3ccnc(Cl)n3)c2O1]

Yield: 54.64%
TLC: Pet ether/Ethyl acetate (7/3): $R_f$: 0.3
LCMS: Mass found (+MS, 290)
Method: A—0.1% TFA in water, B—0.1% TFA in ACN; Flow rate: 2 ml/min.
Column: XBridge C8 (50×4.6 mm, 3.5μ)
Rt (min): 4.00 Area %: 98.05 (at max), 99.43 (at 254 nm).
HPLC: >99%
Method: A—0.1% TFA in water, B—0.1% TFA in ACN; Flow rate: 2 ml/min
Column: XBridge C8 (50×4.6 mm, 3.5μ)
Rt (min): 4.00 Area %: 99.61 (at max), 99.63 (at 254 nm).
$^1$H NMR (400 MHz, DMSO-d6): δ 8.35-8.20 (m, 1H), 8.00-7.90 (m, 1H), 7.08 (d, J=7.20 Hz, 1H), 7.00 (d, J=7.40 Hz, 1H), 6.76 (t, J=7.48 Hz, 1H), 6.52-6.42 (m, 1H), 4.36-4.21 (m, 2H), 3.00 (s, 2H), 1.41 (s, 6H).

(2-Chloro-pyrimidin-4-yl)[3-(pyrazin-2-yloxy)-benzyl]amine

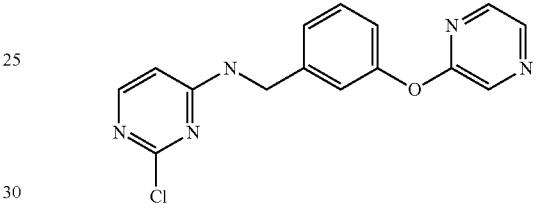

Yield: 38.02%
TLC: CHCl3/MeOH (9.5/0.5): $R_f$: 0.5
LCMS: Mass found (+MS, 314)
Method: A—0.1% TFA in water, B—0.1% TFA in ACN; Flow rate: 2 ml/min.
Column: XBridge C8 (50×4.6 mm, 3.5μ)
Rt (min): 3.19 Area %: 96.86 (at max), 98.78 (at 254 nm).
HPLC: >96%
Method: A—0.1% TFA in water, B—0.1% TFA in ACN; Flow rate: 2 ml/min
Column: XBridge C8 (50×4.6 mm, 3.5μ)
Rt (min): 3.05 Area %: 96.54 (at max), 98.26 (at 254 nm).
$^1$H NMR (400 MHz, DMSO-d6): δ 8.53 (d, J=1.28 Hz, 1H), 8.40-8.39 (m, 1H), 8.37 (d, J=2.64 Hz, 1H), 8.19-8.18 (m, 1H), 8.00-7.92 (m, 1H), 7.41 (t, J=7.88 Hz, 1H), 7.20 (d, J=7.76 Hz, 1H), 7.14 (s, 1H), 7.11-7.09 (m, 1H), 6.51 (d, J=5.72 Hz, 1H), 4.53-4.52 (m, 2H).

(2-Chloro-pyrimidin-4-yl)-(4-morpholin-4-yl-benzyl)-amine

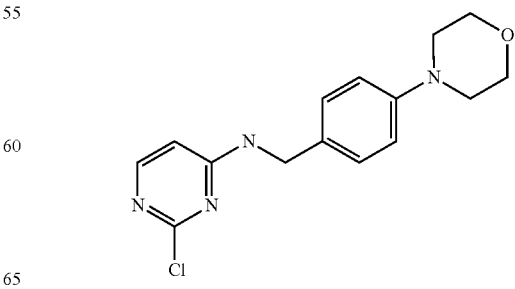

Yield: 32.58%
TLC: Pet ether/Ethyl acetate (5/5): $R_f$: 0.4
LCMS: Mass found (+MS, 305)
Method: A—0.1% TFA in water, B—0.1% TFA in ACN; Flow rate: 2 ml/min.
Column: XBridge C8 (50×4.6 mm, 3.5μ)
Rt (min): 2.15 Area %: 96.87 (at max), 98.74 (at 254 nm).
HPLC: >99%
Method: A—0.1% TFA in water, B—0.1% TFA in ACN; Flow rate: 2 ml/min
Column: XBridge C8 (50×4.6 mm, 3.5μ)
Rt (min): 2.15 Area %: 99.87 (at max), 99.62 (at 254 nm).
$^1$H NMR (400 MHz, DMSO-d6): δ 8.42-8.25 (m, 1H), 7.99-7.88 (m, 1H), 7.18 (d, J=8.56 Hz, 2H), 6.90 (d, J=8.52 Hz, 2H), 6.47 (d, J=5.64 Hz, 1H), 4.38-4.30 (m, 2H), 2.71 (t, J=4.84 Hz, 4H), 3.05 (t, J=4.76 Hz, 4H).

(2-Chloro-pyrimidin-4-yl)-(3-pyrazol-1-yl-benzyl)-amine

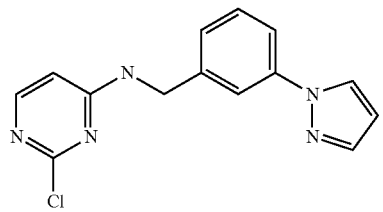 [SMILES: Clc1nccc(NCc2cccc(-n3cccn3)c2)n1]

Yield: 51.47%
TLC: CHCl3/MeOH (9.5/0.5): $R_f$: 0.5
LCMS: Mass found (+MS, 286)
Method: A—0.1% TFA in water, B—0.1% TFA in ACN; Flow rate: 2 ml/min.
Column: XBridge C8 (50×4.6 mm, 3.5μ)
Rt (min): 3.24 Area %: 99.72 (at max), 99.79 (at 254 nm).
HPLC: >98%
Method: A—0.1% TFA in water, B—0.1% TFA in ACN; Flow rate: 2 ml/min
Column: XBridge C8 (50×4.6 mm, 3.5μ)
Rt (min): 3.14 Area %: 98.15 (at max), 99.57 (at 254 nm).
$^1$H NMR (400 MHz, DMSO-d6): δ 8.48-8.44 (m, 2H), 7.94 (d, J=5.72 Hz, 1H), 7.82 (s, 1H), 7.73-7.71 (m, 2H), 7.45 (t, J=7.92 Hz, 1H), 7.24 (d, J=7.56 Hz, 1H), 6.54-6.53 (m, 2H), 4.58-4.46 (m, 2H).

(2-Chloro-pyrimidin-4-yl)-(2,3-dihydro-benzo[1,4]dioxin-6-ylmethyl)-amine

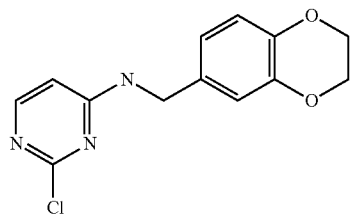 [SMILES: Clc1nccc(NCc2ccc3c(c2)OCCO3)n1]

Yield: 56.81%
TLC: Pet ether/Ethyl acetate (6/4): $R_f$: 0.3
LCMS: Mass found (+MS, 278)
Method: A—0.1% TFA in water, B—0.1% TFA in ACN; Flow rate: 2 ml/min.
Column: XBridge C8 (50×4.6 mm, 3.5μ)
Rt (min): 3.12 Area %: 97.86 (at max), 98.16 (at 254 nm).
HPLC: >98%
Method: A—0.1% TFA in water, B—0.1% TFA in ACN; Flow rate: 2 ml/min
Column: XBridge C8 (50×4.6 mm, 3.5μ)
Rt (min): 3.04 Area %: 98.95 (at max), 98.21 (at 254 nm).
$^1$H NMR (400 MHz, DMSO-d6): δ 8.43-8.27 (m, 1H), 7.95-7.89 (m, 1H), 6.81-6.75 (m, 3H), 6.47 (d, J=5.84 Hz, 1H), 4.35 (d, J=5.36 Hz, 2H), 4.20 (s, 4H).

(2-Chloro-pyrimidin-4-yl)-cyclopropylmethyl-amine

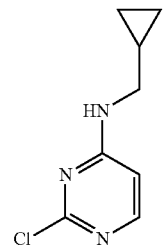 [SMILES: Clc1nccc(NCC2CC2)n1]

Yield: 33.52%
TLC: Pet ether/Ethyl acetate (7/3): $R_f$: 0.4
LCMS: Mass found (+MS, 184.0)
Method: A—0.1% TFA in water, B—0.1% TFA in ACN; Flow rate: 2 ml/min.
Column: XBridge C8 (50×4.6 mm, 3.5μ)
Rt (min): 2.28 Area %: 99.02 (at max), 99.32 (at 254 nm).
HPLC: >99%
Method: A—0.1% TFA in water, B—0.1% TFA in ACN; Flow rate: 2 ml/min
Column: XBridge C8 (50×4.6 mm, 3.5μ)
Rt (min): 2.27 Area %: 99.33 (at max), 99.07 (at 254 nm).
$^1$H NMR (400 MHz, DMSO-d6): δ 8.02 (brs, 1H), 7.86 (d, J=5.76 Hz, 1H), 6.44 (d, J=5.84 Hz, 1H), 3.14-3.11 (m, 2H), 1.04-0.96 (m, 1H), 0.47-0.43 (m, 2H), 0.23-0.19 (m, 2H).

(2-Chloro-pyrimidin-4-yl)-cyclohexylmethyl-amine

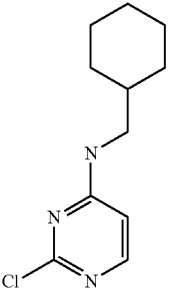 [SMILES: Clc1nccc(NCC2CCCCC2)n1]

Yield: 40.64%
TLC: Pet ether/Ethyl acetate (6/4): $R_f$: 0.5
LCMS: Mass found (+MS, 226.2)
Method: A—0.1% TFA in water, B—0.1% TFA in ACN; Flow rate: 2 ml/min.
Column: XBridge C8 (50×4.6 mm, 3.5μ)
Rt (min): 3.75 Area %: 99.56 (at max), 99.80 (at 254 nm).

HPLC: >99%
Method: A—0.1% TFA in water, B—0.1% TFA in ACN; Flow rate: 2 ml/min
Column: XBridge C8 (50×4.6 mm, 3.5µ)
Rt (min): 2.28 Area %: 99.13 (at max), 99.06 (at 254 nm).
¹H NMR (400 MHz, DMSO-d6): δ 7.87-7.83 (m, 2H), 6.43 (d, J=5.92 Hz, 1H), 3.11 (t, J=6.20, 2H), 1.71-1.59 (m, 5H), 1.22-1.15 (m, 4H), 0.92-0.86 (m, 2H).

Benzyl-(2-chloro-pyrimidin-4-yl)-amine

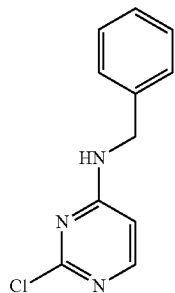 [SMILES: Clc1nccc(NCc2ccccc2)n1]

Yield: 40.85%
TLC: Pet ether/Ethyl acetate (6/4): R$_f$: 0.5
LCMS: Mass found (+MS, 220)
Method: A—0.1% TFA in water, B—0.1% TFA in ACN; Flow rate: 2 ml/min.
Column: XBridge C8 (50×4.6 mm, 3.5µ)
Rt (min): 3.14 Area %: 99.75 (at max), 99.50 (at 254 nm).
HPLC: >99%
Method: A—0.1% TFA in water, B—0.1% TFA in ACN; Flow rate: 2 ml/min
Column: XBridge C8 (50×4.6 mm, 3.5µ)
Rt (min): 3.13 Area %: 99.81 (at max), 99.39 (at 254 nm).
¹H NMR (400 MHz, DMSO-d6): δ 8.37 (s, 1H), 7.92 (d, J=5.60 Hz, 1H), 7.36-7.24 (m, 5H), 6.51 (d, J=5.64 Hz, 1H), 4.49 (d, J=5.16 Hz, 2H).

(2-Chloro-pyrimidin-4-yl)-(2-fluoro-benzyl)-amine

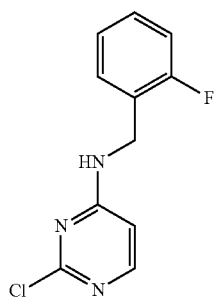 [SMILES: Fc1ccccc1CNc1ccnc(Cl)n1]

Yield: 45.82%
TLC: Pet ether/Ethyl acetate (6/4): R$_f$: 0.5
LCMS: Mass found (+MS, 238)
Method: A—0.1% TFA in water, B—0.1% TFA in ACN; Flow rate: 2 ml/min.
Column: XBridge C8 (50×4.6 mm, 3.5µ)
Rt (min): 3.32 Area %: 98.65 (at max), 99.10 (at 254 nm).
HPLC: >99%
Method: A—0.1% TFA in water, B—0.1% TFA in ACN; Flow rate: 2 ml/min
Column: XBridge C8 (50×4.6 mm, 3.5µ)
Rt (min): 3.36 Area %: 99.25 (at max), 99.08 (at 254 nm).
¹H NMR (400 MHz, DMSO-d6): δ 8.37 (brs, 1H), 7.93 (d, J=5.76 Hz, 1H), 7.39-7.31 (m, 2H), 7.22-7.16 (m, 2H), 6.52 (d, J=5.64 Hz, 1H), 4.52 (d, J=5.20 Hz, 2H).

(2-Chloro-pyrimidin-4-yl)-(4-fluoro-benzyl)-amine

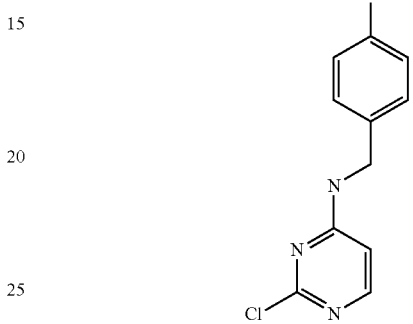

Yield: 42.72%
TLC: Pet ether/Ethyl acetate (6/4): R$_f$: 0.5
LCMS: Mass found (+MS, 238.0)
Method: A—0.1% TFA in water, B—0.1% TFA in ACN; Flow rate: 2 ml/min.
Column: XBridge C8 (50×4.6 mm, 3.5µ)
Rt (min): 3.30 Area %: 97.62 (at max), 99.24 (at 254 nm).
HPLC: >99%
Method: A—0.1% TFA in water, B—0.1% TFA in ACN; Flow rate: 2 ml/min
Column: XBridge C8 (50×4.6 mm, 3.5µ)
Rt (min): 3.24 Area %: 99.00 (at max), 99.40 (at 254 nm).
¹H NMR (400 MHz, DMSO-d6): δ 8.37 (s, 1H), 7.92 (d, J=5.36 Hz, 1H), 7.37-7.33 (m, 2H), 7.19-7.14 (m, 2H), 6.50 (d, J=6.16 Hz, 1H), 4.47 (d, J=5.40 Hz, 2H).

(2-Chloro-pyrimidin-4-yl)-(2,5-difluoro-benzyl)-amine

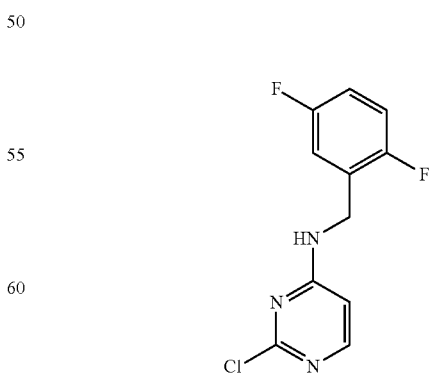

Yield: 39.51%
TLC: Pet ether/Ethyl acetate (6/4): R$_f$: 0.5

LCMS: Mass found (+MS, 256.0)

Method: A—0.1% TFA in water, B—0.1% TFA in ACN; Flow rate: 2 ml/min.

Column: XBridge C8 (50×4.6 mm, 3.5μ)

Rt (min): 3.48 Area %: 97.51 (at max), 98.99 (at 254 nm).

HPLC: >97%

Method: A—0.1% TFA in water, B—0.1% TFA in ACN; Flow rate: 2 ml/min

Column: XBridge C8 (50×4.6 mm, 3.5μ)

Rt (min): 3.41 Area %: 97.89 (at max), 98.48 (at 254 nm).

$^1$H NMR (400 MHz, DMSO-d6): δ 8.39 (t, J=5.36 Hz, 1H), 7.95 (d, J=5.52 Hz, 1H), 7.30-7.24 (m, 1H), 7.20-7.15 (m, 2H), 6.53 (d, J=5.92 Hz, 1H), 4.51 (d, J=4.96 Hz, 2H).

Examples of azaheterocyclic compounds where $R^2$ is H:

General Protocol:

To a 10 ml microwave vial with stir bar was added the chloro-pyrimidine intermediate (1 equiv), respective boronic acid (1.5 equiv), palladium acetate (0.05 equiv), 2-dicyclohexylphosphino-2',6'-dimethoxybiphenyl (0.15 equiv) and potassium carbonate (5 equiv). Reagents were suspended in dioxane (3 ml)/water (0.5 ml) and run in microwave reactor at 120° C. for 45 minutes. The reaction was cooled to room temperature diluted with water (30 ml) and EtOAc (50 ml) and extracted with EtOAc (30 ml). The combined organic layer was washed with water (50 ml) and brine solution then dried over anhydrous sodium sulphate and evaporated. The residue was purified by column chromatography to get the final compound. In some cases preparative HPLC was used to purify the final compounds.

1

(2,3-Difluoro-4-methoxy-benzyl)-[2-(5-methoxy-pyridin-3-yl)-pyrimidin-4-yl]-amine

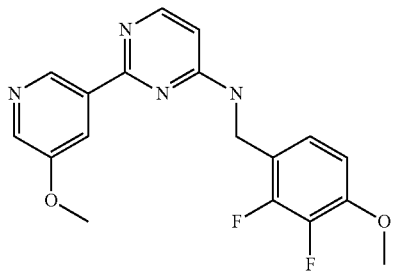 [SMILES: COc1cncc(-c2nccc(NCc3ccc(OC)c(F)c3F)n2)c1]

Yield: 16.98%

TLC: Pet ether/Ethyl acetate (4/6): $R_f$: 0.4

LCMS: Mass found (+MS, 359)

Rt (min): 3.16 Area %: 98.12 (at max), 97.40 (at 254 nm).

HPLC: >97%

Rt (min): 3.17 Area %: 97.68 (at max), 97.17 (at 254 nm).

$^1$H NMR (400 MHz, DMSO-d6): δ 9.03 (d, J=1.6 Hz, 1H), 8.36 (d, J=2.92 Hz, 1H), 8.25-8.19 (m, 1H), 8.15-8.10 (m, 1H), 8.08-8.07 (m, 1H), 7.19 (t, J=7.76 Hz, 1H), 7.00-6.95 (m, 1H), 6.52 (d, J=5.88 Hz, 1H), 4.63 (brs, 2H), 3.89 (s, 3H), 3.82 (s, 3H).

2

[4-(4-Fluoro-phenoxy)-benzyl]-[2-(5-methoxy-pyridin-3-yl)-pyrimidin-4-yl]-amine

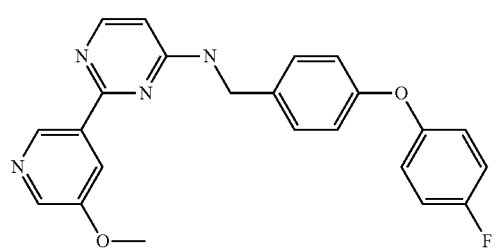 [SMILES: COc1cncc(-c2nccc(NCc3ccc(Oc4ccc(F)cc4)cc3)n2)c1]

Yield: 25.04%

TLC: Pet ether/Ethyl acetate (4/6): $R_f$: 0.3

LCMS: Mass found (+MS, 403.3)

Rt (min): 3.98 Area %: 97.05 (at max), 97.62 (at 254 nm).

HPLC: >97%

Rt (min): 3.99 Area %: 97.29 (at max), 97.35 (at 254 nm).

$^1$H NMR (400 MHz, DMSO-d6): δ 9.02 (s, 1H), 8.36 (d, J=2.84 Hz, 1H), 8.19-8.18 (m, 1H), 8.10 (t, J=5.84 Hz, 1H), 8.06 (s, 1H), 7.39 (d, J=8.32 Hz, 2H), 7.19 (t, J=8.72 Hz, 2H), 7.03-6.99 (m, 2H), 6.95 (d, J=8.48 Hz, 2H), 6.51 (d, J=5.00 Hz, 1H), 4.62 (brs, 2H), 3.87 (s, 3H).

3

[2-(5-Methoxy-pyridin-3-yl)-pyrimidin-4-yl]-[3-(pyrazin-2-yloxy)-benzyl]-amine

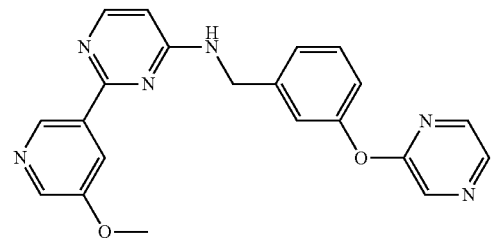 [SMILES: COc1cncc(-c2nccc(NCc3cccc(Oc4cnccn4)c3)n2)c1]

Yield: 24.41%

TLC: CHCl3/MeOH (9/1): $R_f$: 0.4

LCMS: Mass found (+MS, 387.3)

Rt (min): 2.79 Area %: 94.44 (at max), 96.00 (at 254 nm).

HPLC: >94%

Rt (min): 2.78 Area %: 94.89 (at max), 95.35 (at 254 nm).

$^1$H NMR (400 MHz, DMSO-d6): δ 9.00 (s, 1H), 8.50 (s, 1H), 8.33 (s, 2H), 8.17-8.12 (m, 3H), 8.03 (s, 1H), 7.40 (t,

J=7.84 Hz, 1H), 7.28 (d, J=7.56 Hz, 1H), 7.22 (s, 1H), 7.07 (d, J=7.96 Hz, 1H), 6.52 (d, J=4.68 Hz, 1H), 4.67 (brs, 2H), 3.85 (s, 3H).

7.44 (t, J=7.88 Hz, 1H), 7.32 (d, J=7.60 Hz, 1H), 6.55-6.52 (m, 2H), 4.71 (brs, 2H), 3.83 (s, 3H).

4

[2-(5-Methoxy-pyridin-3-yl)-pyrimidin-4-yl]-(4-morpholin-4-yl-benzyl)-amine

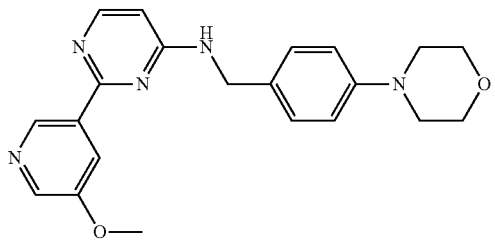 [SMILES: COc1cncc(-c2nccc(NCc3ccc(N4CCOCC4)cc3)n2)c1]

Yield: 23.13%

TLC: CHCl3/MeOH (9.5/0.5): R$_f$: 0.4

LCMS: Mass found (+MS, 378)

Rt (min): 2.20 Area %: 97.47 (at max), 95.91 (at 254 nm).

HPLC: >94%

Rt (min): 2.21 Area %: 97.32 (at max), 94.93 (at 254 nm).

$^1$H NMR (400 MHz, DMSO-d6): δ 9.03 (s, 1H), 8.36 (d, J=2.92 Hz, 1H), 8.16 (brs, 1H), 8.08-8.07 (m, 1H), 8.05-7.96 (m, 1H), 7.25 (d, J=8.40 Hz, 2H), 6.90 (d, J=8.72 Hz, 2H), 6.48 (d, J=5.08 Hz, 1H), 4.54 (brs, 2H), 3.88 (s, 3H), 3.70 (t, J=4.92 Hz, 4H), 3.04 (t, J=4.80 Hz, 4H).

5

[2-(5-Methoxy-pyridin-3-yl)-pyrimidin-4-yl]-(3-pyrazol-1-yl-benzyl)-amine

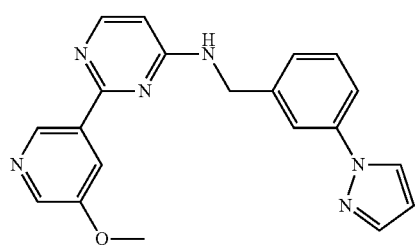 [SMILES: COc1cncc(-c2nccc(NCc3cccc(-n4cccn4)c3)n2)c1]

Yield: 9.45%

TLC: CHCl3/MeOH (9/1): R$_f$: 0.4

LCMS: Mass found (+MS, 359.3)

Rt (min): 2.86 Area %: 93.69 (at max), 93.01 (at 254 nm).

HPLC: >92%

Rt (min): 2.86 Area %: 93.29 (at max), 92.91 (at 254 nm).

$^1$H NMR (400 MHz, DMSO-d6): δ 9.01 (d, J=1.36 Hz, 1H), 8.45 (d, J=2.40 Hz, 1H), 8.34 (d, J=2.72 Hz, 1H), 8.22-8.19 (m, 2H), 8.04 (s, 1H), 7.91 (s, 1H), 7.71-7.68 (m, 2H),

6

(2,3-Dihydro-benzo[1,4]dioxin-6-ylmethyl)-[2-(5-methoxy-pyridin-3-yl)-pyrimidin-4-yl]-amine

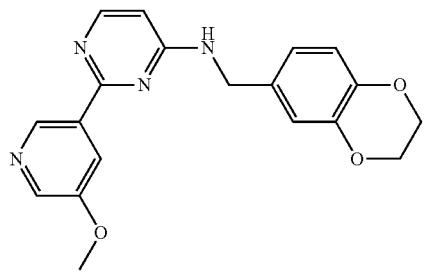 [SMILES: COc1cncc(-c2nccc(NCc3ccc4c(c3)OCCO4)n2)c1]

Yield: 13.14%

TLC: Pet ether/Ethyl acetate (4/6): R$_f$: 0.3

LCMS: Mass found (+MS, 351)

Rt (min): 2.80 Area %: 97.74 (at max), 95.87 (at 254 nm).

HPLC: >94%

Rt (min): 2.83 Area %: 94.72 (at max), 96.83 (at 254 nm).

$^1$H NMR (400 MHz, DMSO-d6): δ 9.03 (s, 1H), 8.36 (d, J=2.84 Hz, 1H), 8.17 (brs, 1H), 8.07-8.02 (m, 2H), 6.88-6.78 (m, 3H), 6.49 (d, J=4.72 Hz, 1H), 4.51 (brs, 2H), 4.18 (s, 4H), 3.89 (s, 3H).

7

[4-(4-Fluoro-phenoxy)-benzyl]-[2-(5-fluoro-pyridin-3-yl)-pyrimidin-4-yl]-amine

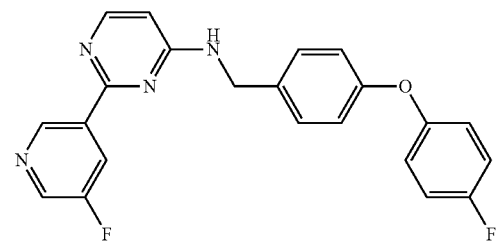

Yield: 23.06%

TLC: Pet ether/Ethyl acetate (4/6): R$_f$: 0.4

LCMS: Mass found (+MS, 391)

Rt (min): 4.11 Area %: 98.76 (at max), 98.47 (at 254 nm).

HPLC: >97%

Rt (min): 4.12 Area %: 98.50 (at max), 97.81 (at 254 nm).

$^1$H NMR (400 MHz, DMSO-d6): δ 9.28 (t, J=1.56 Hz, 1H), 8.67 (d, J=2.84 Hz, 1H), 8.32 (dd, J=10.02, 1.64 Hz, 1H), 8.20-8.13 (m, 2H), 7.39 (d, J=8.48 Hz, 2H), 7.22-7.17 (m, 2H), 7.03-6.99 (m, 2H), 6.98-6.94 (m, 2H), 6.54 (d, J=5.84 Hz, 1H), 4.64 (brs, 2H).

8

(2,2-Dimethyl-2,3-dihydro-benzofuran-7-ylmethyl)-[2-(5-fluoro-pyridin-3-yl)-pyrimidin-4-yl]-amine

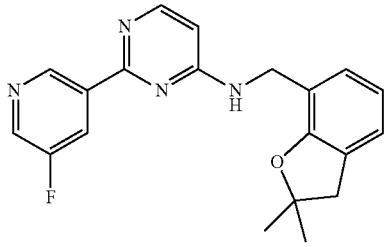 [SMILES: CC1(C)Cc2cccc(CNc3ccnc(-c4cncc(F)c4)n3)c2O1]

Yield: 15.74%

TLC: Pet ether/Ethyl acetate (5/5): $R_f$: 0.3

LCMS: Mass found (+MS, 351.3)

Rt (min): 3.71 Area %: 97.04 (at max), 97.77 (at 254 nm).

HPLC: >96%

Rt (min): 3.70 Area %: 96.27 (at max), 98.78 (at 254 nm).

$^1$H NMR (400 MHz, DMSO-d6): δ 9.28 (s, 1H), 8.66 (d, J=2.80 Hz, 1H), 8.31-8.28 (m, 1H), 8.18 (d, J=5.12 Hz, 1H), 8.05 (t, J=6.00 Hz, 1H), 7.05 (d, J=7.20 Hz, 2H), 6.74 (t, J=7.44 Hz, 1H), 6.55-6.54 (m, 1H), 4.54 (brs, 2H), 3.00 (s, 2H), 1.44 (s, 6H).

9

[2-(5-Fluoro-pyridin-3-yl)-pyrimidin-4-yl]-[3-(pyrazin-2-yloxy)-benzyl]-amine

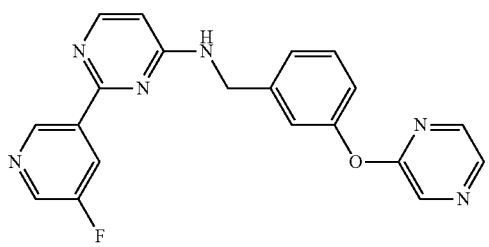 [SMILES: Fc1cncc(-c2nccc(NCc3cccc(Oc4cnccn4)c3)n2)c1]

Yield: 17.74%

TLC: CHCl3/MeOH (9/1): $R_f$: 0.5

LCMS: Mass found (+MS, 375)

Rt (min): 2.84 Area %: 92.75 (at max), 96.57 (at 254 nm).

HPLC: >92%

Rt (min): 2.89 Area %: 92.00 (at max), 96.14 (at 254 nm).

$^1$H NMR (400 MHz, DMSO-d6): δ 9.26 (t, J=1.52 Hz, 1H), 8.65 (d, J=2.68 Hz, 1H), 8.50 (d, J=1.08 Hz, 1H), 8.33-8.28 (m, 2H), 8.21-8.19 (m, 2H), 8.11 (s, 1H), 7.40 (t, J=7.84 Hz, 1H), 7.28 (d, J=7.64 Hz, 1H), 7.22 (s, 1H), 7.08 (dd, J=7.98, 1.68 Hz, 1H), 6.55 (d, J=5.80 Hz, 1H), 4.68 (brs, 2H).

10

[2-(5-Fluoro-pyridin-3-yl)-pyrimidin-4-yl]-(4-morpholin-4-yl-benzyl)-amine

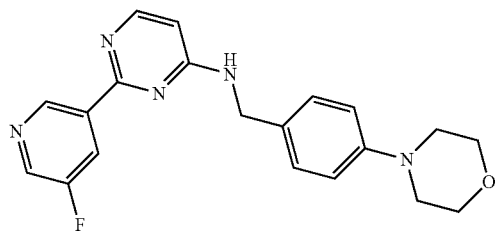 [SMILES: Fc1cncc(-c2nccc(NCc3ccc(N4CCOCC4)cc3)n2)c1]

Yield: 38.09%

TLC: CHCl3/MeOH (9.5/0.5): $R_f$: 0.4

LCMS: Mass found (+MS, 366)

Rt (min): 2.26 Area %: 96.60 (at max), 98.58 (at 254 nm).

HPLC: >98%

Rt (min): 2.26 Area %: 98.02 (at max), 98.03 (at 254 nm).

$^1$H NMR (400 MHz, DMSO-d6): δ 9.30 (s, 1H), 8.67 (d, J=2.88 Hz, 1H), 8.34 (d, J=9.72 Hz, 1H), 8.18 (d, J=4.88 Hz, 1H), 8.06 (brs, 1H), 7.25 (d, J=8.40 Hz, 2H), 6.90 (d, J=8.72 Hz, 2H), 6.52 (d, J=5.24 Hz, 1H), 4.56 (brs, 2H), 3.70 (t, J=4.92 Hz, 4H), 3.04 (t, J=4.84 Hz, 4H).

11

[2-(5-Fluoro-pyridin-3-yl)-pyrimidin-4-yl]-(3-pyrazol-1-yl-benzyl)-amine

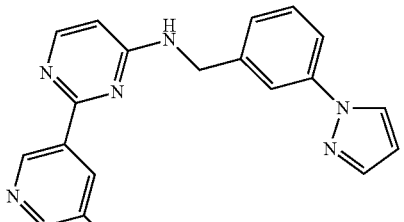

Yield: 19.82%

TLC: CHCl3/MeOH (9.5/0.5): $R_f$: 0.4

LCMS: Mass found (+MS, 347)

Rt (min): 2.96 Area %: 98.88 (at max), 99.53 (at 254 nm).

HPLC: >98%

Rt (min): 2.98 Area %: 98.67 (at max), 99.63 (at 254 nm).

$^1$H NMR (400 MHz, DMSO-d6): δ 9.28 (d, J=1.44 Hz, 1H), 8.65 (d, J=2.56 Hz, 1H), 8.46 (d, J=2.44 Hz, 1H), 8.35-8.31 (m, 1H), 8.26-8.21 (m, 2H), 7.92 (s, 1H), 7.71-7.69 (m,

2H), 7.45 (t, J=7.88 Hz, 1H), 7.32 (d, J=7.60 Hz, 1H), 6.58 (d, J=5.08 Hz, 1H), 6.53-6.52 (m, 1H), 4.74 (brs, 2H).

12

(2,3-Dihydro-benzo[1,4]dioxin-6-ylmethyl)-[2-(5-fluoro-pyridin-3-yl)-pyrimidin-4-yl]-amine

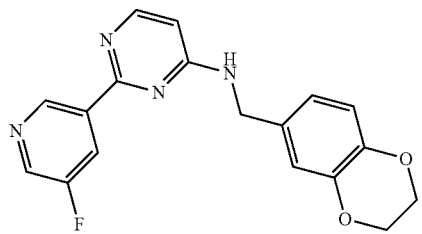 [SMILES: Fc1cncc(-c2nccc(NCc3ccc4c(c3)OCCO4)n2)c1]

Yield: 8.90%
TLC: Pet ether/Ethyl acetate (5/5): $R_f$: 0.3
LCMS: Mass found (+MS, 339)
Rt (min): 2.90 Area %: 95.46 (at max), 96.88 (at 254 nm).
HPLC: >97%
Rt (min): 2.94 Area %: 97.58 (at max), 97.30 (at 254 nm).
$^1$H NMR (400 MHz, DMSO-d6): δ 9.29 (s, 1H), 8.67 (d, J=2.84 Hz, 1H), 8.34-8.31 (m, 1H), 8.19 (brs, 1H), 8.07 (brs, 1H), 6.87-6.78 (m, 3H), 6.52 (d, J=5.16 Hz, 1H), 4.53 (brs, 2H), 4.18 (s, 4H).

13

(5-{4-[4-(4-Fluoro-phenoxy)-benzylamino]-pyrimidin-2-yl}-pyridin-3-yl)-morpholin-4-yl-methanone

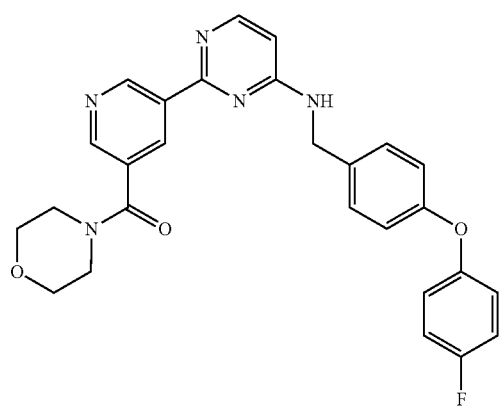 [SMILES: O=C(c1cncc(-c2nccc(NCc3ccc(Oc4ccc(F)cc4)cc3)n2)c1)N1CCOCC1]

Yield: 21.34%
TLC: CHCl3/MeOH (9.5/0.5): $R_f$: 0.4
LCMS: Mass found (+MS, 486.3)
Rt (min): 3.63 Area %: 97.12 (at max), 97.24 (at 254 nm).
HPLC: >95%
Rt (min): 3.70 Area %: 95.92 (at max), 97.14 (at 254 nm).
$^1$H NMR (400 MHz, DMSO-d6): δ 9.45 (d, J=2.00 Hz, 1H), 8.69 (d, J=2.08 Hz, 1H), 8.54-8.53 (m, 1H), 8.20 (d, J=4.32 Hz, 1H), 8.13 (t, J=5.84 Hz, 1H), 7.39 (d, J=8.52 Hz, 2H), 7.22-7.17 (m, 2H), 7.03-7.00 (m, 2H), 6.97-6.94 (m, 2H), 6.53 (d, J=4.44 Hz, 1H), 4.64 (brs, 2H), 3.65-3.53 (m, 8H).

14

Morpholin-4-yl-{5-[4-(4-morpholin-4-yl-benzylamino)-pyrimidin-2-yl]-pyridin-3-yl}-methanone

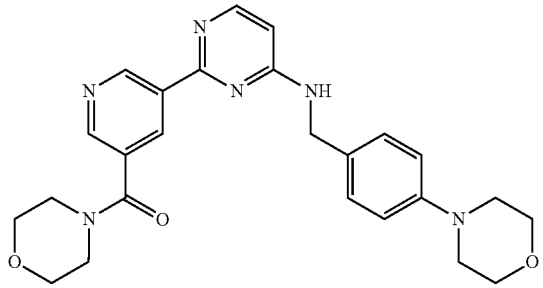 [SMILES: O=C(c1cncc(-c2nccc(NCc3ccc(N4CCOCC4)cc3)n2)c1)N1CCOCC1]

Yield: 42.47%
TLC: CHCl3/MeOH (9/1): $R_f$: 0.4
LCMS: Mass found (+MS, 461.2)
Rt (min): 2.02 Area %: 99.33 (at max), 99.78 (at 254 nm).
HPLC: >99%
Rt (min): 2.00 Area %: 99.48 (at max), 99.60 (at 254 nm).
$^1$H NMR (400 MHz, DMSO-d6): δ 9.46 (s, 1H), 8.69 (d, J=2.12 Hz, 1H), 8.54 (t, J=2.04 Hz, 1H), 8.18 (brs, 1H), 8.04 (brs, 1H), 7.24 (d, J=8.52 Hz, 2H), 6.90 (d, J=8.72 Hz, 2H), 6.50 (brs, 1H), 4.56 (brs, 2H), 3.71-3.66 (m, 8H), 3.56-3.51 (m, 2H), 3.40-3.37 (m, 2H), 3.04 (t, J=4.80 Hz, 4H).

15

(5-{4-[(2,3-Dihydro-benzo[1,4]dioxin-6-ylmethyl)-amino]-pyrimidin-2-yl}-pyridin-3-yl)-morpholin-4-yl-methanone

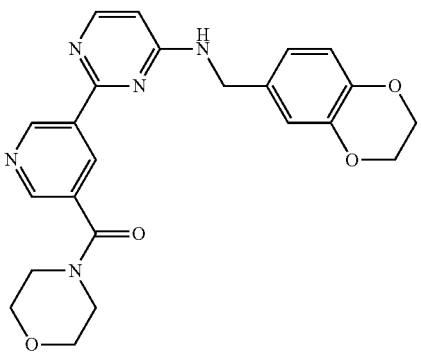 [SMILES: O=C(c1cncc(-c2nccc(NCc3ccc4c(c3)OCCO4)n2)c1)N1CCOCC1]

Yield: 34.11%
TLC: CHCl3/MeOH (9.5/0.5): $R_f$: 0.4
LCMS: Mass found (+MS, 434)
Rt (min): 2.51 Area %: 97.17 (at max), 97.84 (at 254 nm).
HPLC: >96%
Rt (min): 2.53 Area %: 96.83 (at max), 97.27 (at 254 nm).
$^1$H NMR (400 MHz, DMSO-d6): δ 9.46 (s, 1H), 8.69 (d, J=2.04 Hz, 1H), 8.54 (t, J=2.04 Hz, 1H), 8.19 (d, J=4.64 Hz, 1H), 8.06 (t, J=6.12 Hz, 1H), 6.87-6.78 (m, 3H), 6.51 (d, J=4.96 Hz, 1H), 4.53 (brs, 2H), 4.18 (s, 4H), 3.66-3.54 (m, 8H).

16

(4-Chloro-2-fluoro-benzyl)-[2-(5-methoxy-pyridin-3-yl)-pyrimidin-4-yl]-amine

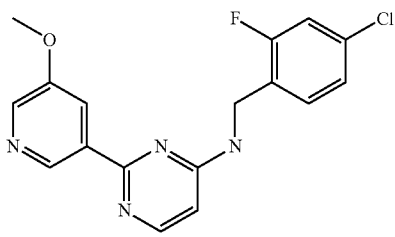 [SMILES: COc1cncc(-c2nccc(NCc3ccc(Cl)cc3F)n2)c1]

Yield: 8.74%
TLC: Pet ether/Ethyl acetate (4/6): $R_f$: 0.4
LCMS: Mass found (+MS, 345)
Rt (min): 3.36 Area %: 94.97 (at max), 96.56 (at 254 nm).
HPLC: >96%
Rt (min): 3.35 Area %: 96.86 (at max), 97.08 (at 254 nm).
$^1$H NMR (400 MHz, DMSO-d6): δ 8.99 (s, 1H), 8.35 (d, J=2.8 Hz, 1H), 8.20-8.15 (m, 2H), 8.03 (s, 1H), 7.45-7.41 (m, 2H), 7.25 (dd, J=8.30, 1.76 Hz, 1H), 6.55 (d, J=5.48 Hz, 1H), 4.64 (brs, 2H), 3.87 (s, 3H).

17

(2,2-Dimethyl-2,3-dihydro-benzofuran-7-ylmethyl)-[2-(5-methoxy-pyridin-3-yl)-pyrimidin-4-yl]-amine

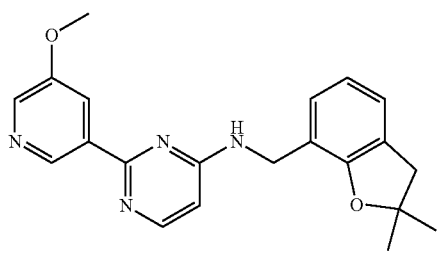 [SMILES: COc1cncc(-c2nccc(NCc3cccc4c3OC(C)(C)C4)n2)c1]

Yield: 13.81%
TLC: Pet ether/Ethyl acetate (4/6): $R_f$: 0.3
LCMS: Mass found (+MS, 363.3)
Rt (min): 3.51 Area %: 98.36 (at max), 98.55 (at 254 nm).
HPLC: >98%
Rt (min): 3.53 Area %: 98.66 (at max), 98.40 (at 254 nm).
$^1$H NMR (400 MHz, DMSO-d6): δ 9.02 (d, J=1.28 Hz, 1H), 8.35 (d, J=2.92 Hz, 1H), 8.16 (brs, 1H), 8.06-8.05 (m, 1H), 7.96 (t, J=5.76 Hz, 1H), 7.07-7.04 (m, 2H), 6.74 (t, J=7.48 Hz, 1H), 6.51 (brs, 1H), 4.53 (brs, 2H), 3.87 (s, 3H), 3.00 (s, 2H), 1.43 (s, 6H).

18

[2-(5-Chloro-pyridin-3-yl)-pyrimidin-4-yl]-(2,2-dimethyl-2,3-dihydro-benzofuran-7-ylmethyl)-amine

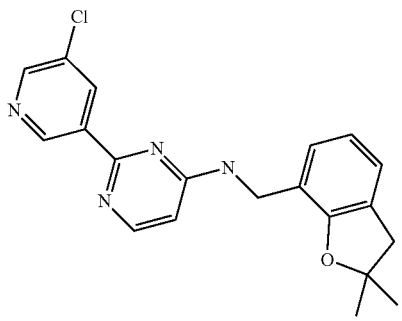 [SMILES: CC1(C)Cc2cccc(CNc3ccnc(-c4cncc(Cl)c4)n3)c2O1]

Yield: 14.85%
TLC: Pet ether/Ethyl acetate (5/5): $R_f$: 0.3
LCMS: Mass found (+MS, 367)
Rt (min): 3.89 Area %: 98.19 (at max), 98.95 (at 254 nm).
HPLC: >99%
Rt (min): 3.94 Area %: 99.21 (at max), 99.39 (at 254 nm).
$^1$H NMR (400 MHz, DMSO-d6): δ 9.33 (d, J=1.64 Hz, 1H), 8.70 (d, J=2.4 Hz, 1H), 8.51 (s, 1H), 8.18 (brs, 1H), 8.06 (t, J=5.60 Hz, 1H), 7.05 (d, J=7.44 Hz, 2H), 6.74 (t, J=7.44 Hz, 1H), 6.55 (brs, 1H), 4.54 (brs, 2H), 3.00 (s, 2H), 1.44 (s, 6H).

19

[2-(5-Chloro-pyridin-3-yl)-pyrimidin-4-yl]-[3-(pyrazin-2-yloxy)-benzyl]-amine

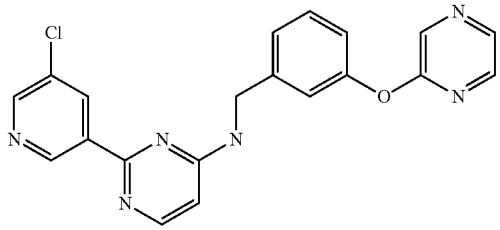 [SMILES: Clc1cncc(-c2nccc(NCc3cccc(Oc4cnccn4)c3)n2)c1]

Yield: 18.57%
TLC: CHCl3/MeOH (9.5/0.5): $R_f$: 0.4
LCMS: Mass found (+MS, 391)
Rt (min): 3.08 Area %: 94.75 (at max), 95.16 at 254 nm).
HPLC: >92%
Rt (min): 3.10 Area %: 92.07 (at max), 92.93 (at 254 nm).
$^1$H NMR (400 MHz, DMSO-d6): δ 9.31 (d, J=1.72 Hz, 1H), 8.69 (d, J=2.24 Hz, 1H), 8.51-8.50 (m, 2H), 8.32 (d, J=2.4 Hz, 1H), 8.22-8.19 (m, 2H), 8.10 (brs, 1H), 7.41 (t, J=7.80 Hz, 1H), 7.27 (d, J=7.96 Hz, 1H), 7.21 (s, 1H), 7.08 (dd, J=7.80, 1.64 Hz, 1H), 6.55 (brs, 1H), 4.67 (brs, 2H).

20

[2-(5-Chloro-pyridin-3-yl)-pyrimidin-4-yl]-(4-morpholin-4-yl-benzyl)-amine

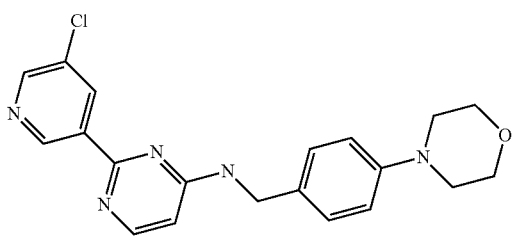 [SMILES: Clc1cncc(-c2nccc(NCc3ccc(N4CCOCC4)cc3)n2)c1]

Yield: 4.71%
TLC: CHCl3/MeOH (9.5/0.5): R_f: 0.4
LCMS: Mass found (+MS, 382)
Rt (min): 2.54 Area %: 98.20 (at max), 98.94 (at 254 nm).
HPLC: >98%
Rt (min): 2.53 Area %: 98.09 (at max), 98.92 (at 254 nm).
$^1$H NMR (400 MHz, DMSO-d6): δ 9.34 (s, 1H), 8.71 (d, J=2.44 Hz, 1H), 8.56-8.55 (m, 1H), 8.17 (brs, 1H), 8.06 (brs, 1H), 7.25 (d, J=8.40 Hz, 2H), 6.90 (d, J=8.72 Hz, 2H), 6.52 (brs, 1H), 4.54 (brs, 2H), 3.70 (t, J=4.72 Hz, 4H), 3.04 (t, J=4.80 Hz, 4H).

21

(2,3-Difluoro-4-methoxy-benzyl)-[2-(5-fluoro-pyridin-3-yl)-pyrimidin-4-yl]-amine

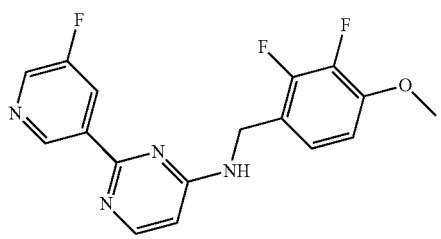 [SMILES: COc1ccc(CNc2ccnc(-c3cncc(F)c3)n2)c(F)c1F]

Yield: 14.17%
TLC: Pet ether/Ethyl acetate (5/5): R_f: 0.4
LCMS: Mass found (+MS, 347)
Rt (min): 3.33 Area %: 99.62 (at max), 99.66 (at 254 nm).
HPLC: >99%
Rt (min): 3.25 Area %: 99.27 (at max), 99.50 (at 254 nm).
$^1$H NMR (400 MHz, DMSO-d6): δ 9.27 (s, 1H), 8.73 (d, J=2.48 Hz, 1H), 8.59 (s, 1H), 8.37-8.35 (m, 1H), 8.23-8.22

(m, 1H), 7.21-7.19 (m, 1H), 7.01-6.97 (m, 1H), 6.62 (d, J=6.2 Hz, 1H), 4.69 (brs, 2H), 3.82 (s, 3H).

22

{5-[4-(4-Chloro-2-fluoro-benzylamino)-pyrimidin-2-yl]-pyridin-3-yl}-morpholin-4-yl-methanone

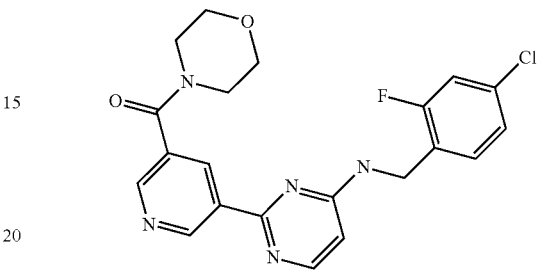

Yield: 11.34%
TLC: CHCl3/MeOH (9.5/0.5): R_f: 0.4
LCMS: Mass found (+MS, 428.0)
Rt (min): 3.37 Area %: 95.61 (at max), 95.92 (at 254 nm).
HPLC: >96%
Rt (min): 3.03 Area %: 97.52 (at max), 96.69 (at 254 nm).
$^1$H NMR (400 MHz, DMSO-d6): δ 9.43 (d, J=2.00 Hz, 1H), 8.69 (d, J=2.00 Hz, 1H), 8.50 (s, 1H), 8.23-8.18 (m, 2H), 7.46-7.41 (m, 2H), 7.26-7.24 (m, 1H), 6.56 (d, J=5.72 Hz, 1H), 4.66 (brs, 2H), 3.66-3.54 (m, 8H).

23

Morpholin-4-yl-(5-{4-[3-(pyrazin-2-yloxy)-benzylamino]-pyrimidin-2-yl}-pyridin-3-yl)-methanone

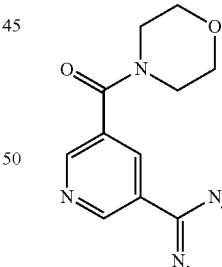

Yield: 14.15%
TLC: CHCl3/MeOH (9/1): R_f: 0.2
LCMS: Mass found (+MS, 470.3)
Rt (min): 2.50 Area %: 97.14 (at max), 99.02 (at 254 nm).
HPLC: >97%
Rt (min): 2.55 Area %: 97.21 (at max), 98.66 (at 254 nm).
$^1$H NMR (400 MHz, DMSO-d6): δ 9.43 (d, J=2.00 Hz, 1H), 8.68 (d, J=2.00 Hz, 1H), 8.52-8.50 (m, 2H), 8.33 (d, J=2.40 Hz, 1H), 8.21-8.13 (m, 3H), 7.40 (t, J=8.00 Hz, 1H), 7.27 (d, J=7.60 Hz, 1H), 7.20 (s, 1H), 7.08 (dd, J=7.98, 1.64 Hz, 1H), 6.54 (d, J=5.84 Hz, 1H), 4.69 (brs, 2H), 3.32-3.65 (m, 6H).

24

(2,3-Difluoro-4-methoxy-benzyl)-[2-(5-trifluoromethyl-pyridin-3-yl)-pyrimidin-4-yl]-amine

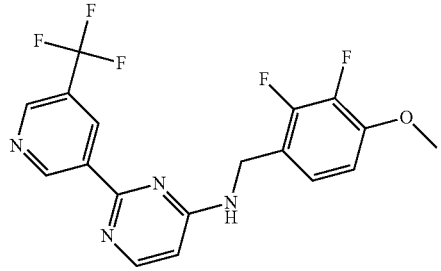 [SMILES: COc1ccc(CNc2ccnc(-c3cncc(C(F)(F)F)c3)n2)c(F)c1F]

Yield: 12.09%

TLC: Pet ether/Ethyl acetate (5/5): R$_f$: 0.4

LCMS: Mass found (+MS, 397)

Rt (min): 3.87 Area %: 90.42 (at max), 97.36 (at 254 nm).

HPLC: >94%

Rt (min): 3.87 Area %: 94.12 (at max), 97.58 (at 254 nm).

$^1$H NMR (400 MHz, DMSO-d6): δ 9.67 (d, J=1.60 Hz, 1H), 9.07 (d, J=1.48 Hz, 1H), 8.79 (s, 1H), 8.26-8.22 (m, 2H), 7.20-7.17 (m, 1H), 6.99-6.95 (m, 1H), 6.58 (d, J=5.96 Hz, 1H), 4.63 (s, 2H), 3.81 (s, 3H).

25

[4-(4-Fluoro-phenoxy)-benzyl]-[2-(5-trifluoromethyl-pyridin-3-yl)-pyrimidin-4-yl]-amine

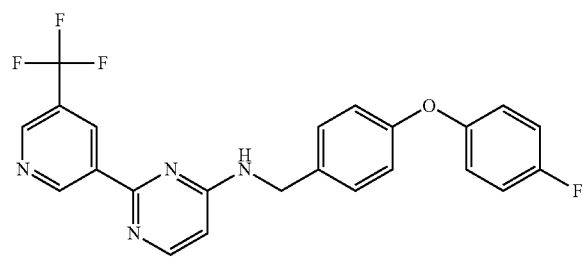 [SMILES: Fc1ccc(Oc2ccc(CNc3ccnc(-c4cncc(C(F)(F)F)c4)n3)cc2)cc1]

Yield: 42.62%

TLC: Pet ether/Ethyl acetate (5/5): R$_f$: 0.4

LCMS: Mass found (+MS, 441.3)

Rt (min): 4.62 Area %: 97.72 (at max), 98.95 (at 254 nm).

HPLC: >98%

Rt (min): 4.62 Area %: 98.37 (at max), 98.18 (at 254 nm).

$^1$H NMR (400 MHz, DMSO-d6): δ 9.65 (d, J=1.72 Hz, 1H), 9.07 (d, J=1.32 Hz, 1H), 8.77 (s, 1H), 8.26-8.22 (m, 2H), 7.39 (d, J=8.44 Hz, 2H), 7.21-7.16 (m, 2H), 7.02-6.93 (m, 4H), 6.57 (d, J=5.48 Hz, 1H), 4.63 (s, 2H).

26

(2,2-Dimethyl-2,3-dihydro-benzofuran-7-ylmethyl)-[2-(5-trifluoromethyl-pyridin-3-yl)-pyrimidin-4-yl]-amine

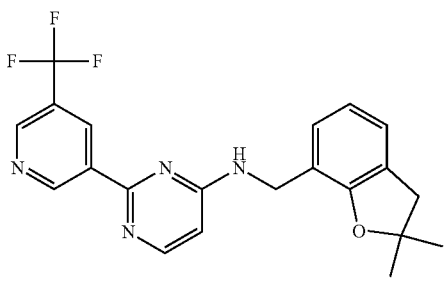 [SMILES: CC1(C)Cc2cccc(CNc3ccnc(-c4cncc(C(F)(F)F)c4)n3)c2O1]

Yield: 14.98%

TLC: Pet ether/Ethyl acetate (4/6): R$_f$: 0.4

LCMS: Mass found (+MS, 401.2)

Rt (min): 4.34 Area %: 98.50 (at max), 99.21 (at 254 nm).

HPLC: >98%

Rt (min): 4.33 Area %: 98.94 (at max), 99.19 (at 254 nm).

$^1$H NMR (400 MHz, DMSO-d6): δ 9.66 (d, J=1.60 Hz, 1H), 9.06 (s, 1H), 8.77 (s, 1H), 8.21-8.11 (m, 2H), 7.06-7.05 (m, 2H), 6.74 (t, J=7.36 Hz, 1H), 6.58 (brs, 1H), 4.55 (brs, 2H), 3.00 (s, 2H), 1.43 (s, 6H).

27

[3-(Pyrazin-2-yloxy)-benzyl]-[2-(5-trifluoromethyl-pyridin-3-yl)-pyrimidin-4-yl]-amine

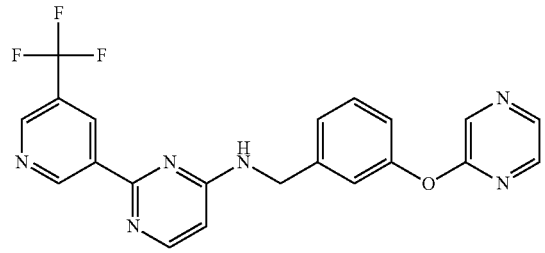 [SMILES: FC(F)(F)c1cncc(-c2nccc(NCc3cccc(Oc4cnccn4)c3)n2)c1]

Yield: 7.92%

TLC: CHCl3/MeOH (9.5/0.5): R$_f$: 0.3

LCMS: Mass found (+MS, 425.3)

Rt (min): 3.49 Area %: 93.59 (at max), 94.61 (at 254 nm).

HPLC: >95%

Rt (min): 3.45 Area %: 97.16 (at max), 95.35 (at 254 nm).

$^1$H NMR (400 MHz, DMSO-d6): δ 9.63 (s, 1H), 9.06 (s, 1H), 8.76 (s, 1H), 8.49 (s, 1H), 8.37-8.31 (m, 2H), 8.24-8.22

(m, 1H), 8.09 (s, 1H), 7.40 (t, J=7.88 Hz, 1H), 7.28 (d, J=7.68 Hz, 2H), 7.07 (d, J=7.6 Hz, 1H), 6.59 (d, J=5.88 Hz 1H), 4.69 (brs, 2H).

28

(4-Morpholin-4-yl-benzyl)-[2-(5-trifluoromethyl-pyridin-3-yl)-pyrimidin-4-yl]-amine

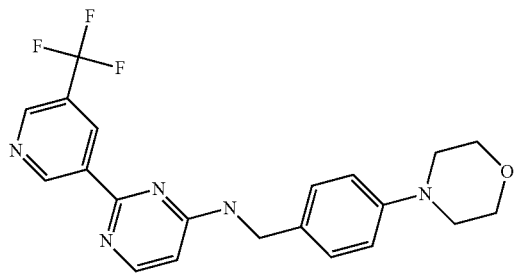 [SMILES: FC(F)(F)c1cncc(-c2nccc(NCc3ccc(N4CCOCC4)cc3)n2)c1]

Yield: 50.30%
TLC: CHCl3/MeOH (9.5/0.5): R$_f$: 0.4
LCMS: Mass found (+MS, 416.0)
Rt (min): 2.88 Area %: 98.06 (at max), 98.51 (at 254 nm).
HPLC: >99%
Rt (min): 2.91 Area %: 99.21 (at max), 99.52 (at 254 nm).
$^1$H NMR (400 MHz, DMSO-d6): δ 9.67 (s, 1H), 9.07 (d, J=1.20 Hz, 1H), 8.80 (s, 1H), 8.20-8.13 (m, 2H), 7.25 (d, J=8.32 Hz, 2H), 6.90 (d, J=8.80 Hz, 2H), 6.54 (d, J=5.72 Hz, 1H), 4.54 (brs, 2H), 3.70 (t, J=4.92 Hz, 4H), 3.04 (t, J=5.08 Hz, 4H).

29

(3-Pyrazol-1-yl-benzyl)-[2-(5-trifluoromethyl-pyridin-3-yl)-pyrimidin-4-yl]-amine

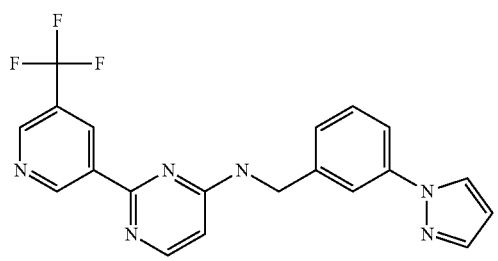 [SMILES: FC(F)(F)c1cncc(-c2nccc(NCc3cccc(-n4cccn4)c3)n2)c1]

Yield: 31.43%
TLC: CHCl3/MeOH (9.5/0.5): R$_f$: 0.4
LCMS: Mass found (+MS, 397.0)
Rt (min): 3.53 Area %: 99.29 (at max), 99.56 (at 254 nm).
HPLC: >99%
Rt (min): 3.61 Area %: 99.69 (at max), 99.44 (at 254 nm).
$^1$H NMR (400 MHz, DMSO-d6): δ 9.66 (d, J=1.60 Hz, 1H), 9.05 (s, 1H), 8.76 (s, 1H), 8.45 (d, J=2.40 Hz, 1H), 8.32-8.23 (m, 2H), 7.91 (s, 1H), 7.71-7.68 (m, 2H), 7.44 (t, J=7.88 Hz, 1H), 7.32 (d, J=7.52 Hz, 1H), 6.61 (d, J=5.2 Hz, 1H), 6.52-6.51 (m, 1H), 4.73 (brs, 2H).

30

(2,3-Dihydro-benzo[1,4]dioxin-6-ylmethyl)-[2-(5-trifluoromethyl-pyridin-3-yl)-pyrimidin-4-yl]-amine

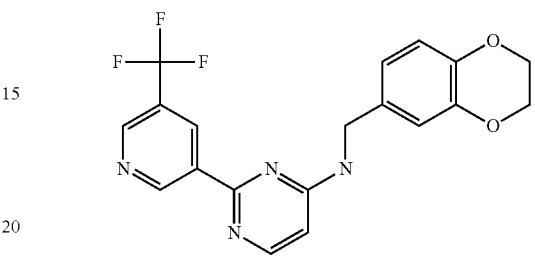

Yield: 12.75%
TLC: Pet ether/Ethyl acetate (5/5): R$_f$: 0.4
LCMS: Mass found (+MS, 389.0)
Rt (min): 3.50 Area %: 98.03 (at max), 98.70 (at 254 nm).
HPLC: >99%
Rt (min): 3.61 Area %: 99.46 (at max), 99.60 (at 254 nm).
$^1$H NMR (400 MHz, DMSO-d6): δ 9.67 (s, 1H), 9.07 (d, J=1.36 Hz, 1H), 8.79 (s, 1H), 8.21-8.14 (m, 2H), 6.87-6.78 (m, 3H), 6.55 (d, J=5.52 Hz, 1H), 4.52 (brs, 2H), 4.18 (s, 4H).

31

[2-(5-Chloro-pyridin-3-yl)-pyrimidin-4-yl]-[4-(4-fluoro-phenoxy)-benzyl]-amine

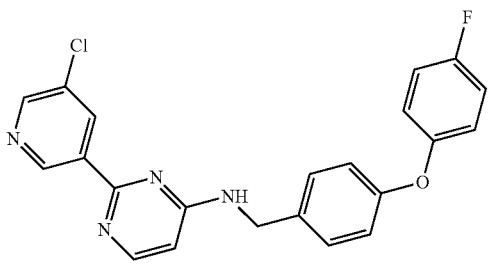 [SMILES: Fc1ccc(Oc2ccc(CNc3ccnc(-c4cncc(Cl)c4)n3)cc2)cc1]

Yield: 5.83%
TLC: Pet ether/Ethyl acetate (5/5): R$_f$: 0.3
LCMS: Mass found (+MS, 407)
Rt (min): 4.30 Area %: 97.51 (at max), 97.49 (at 254 nm).
HPLC: >97%
Rt (min): 4.33 Area %: 97.19 (at max), 97.23 (at 254 nm).
$^1$H NMR (400 MHz, DMSO-d6): δ 9.33 (d, J=1.72 Hz, 1H), 8.71 (d, J=2.44 Hz, 1H), 8.54-8.53 (m, 1H), 8.20-8.16

(m, 2H), 7.39 (d, J=8.52 Hz, 2H), 7.22-7.17 (m, 2H), 7.04-6.99 (m, 2H), 6.98-6.94 (m, 2H), 6.54 (d, J=5.96 Hz, 1H), 4.64 (s, 2H).

32

(4-Chloro-2-fluoro-benzyl)-[2-(5-chloro-pyridin-3-yl)-pyrimidin-4-yl]-amine

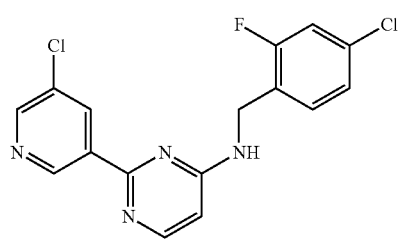 [SMILES: Fc1cncc(-c2nccc(NCc3ccc(Cl)cc3F)n2)c1]

Yield: 3.97%

TLC: Pet ether/Ethyl acetate (5/5): $R_f$: 0.3

LCMS: Mass found (+MS, 349)

Rt (min): 3.74 Area %: 96.65 (at max), 98.63 (at 254 nm).

HPLC: >98%

Rt (min): 3.76 Area %: 98.92 (at max), 98.76 (at 254 nm).

$^1$H NMR (400 MHz, CDCl3): δ 9.44 (d, J=1.76 Hz, 1H), 8.65-8.61 (m, 2H), 8.30 (d, J=5.88 Hz, 1H), 7.38-7.34 (m, 1H), 7.16-7.12 (m, 2H), 6.35 (d, J=5.92 Hz, 1H), 5.34 (brs, 1H), 4.72 (brs, 2H).

33

(4-Chloro-2-fluoro-benzyl)-[2-(5-fluoro-pyridin-3-yl)-pyrimidin-4-yl]-amine

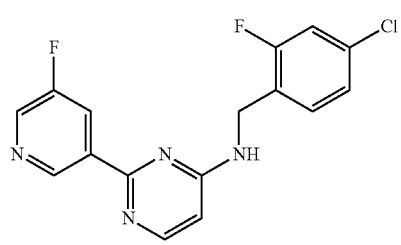

Yield: 44.56%

TLC: Pet ether/Ethyl acetate (5/5): $R_f$: 0.4

LCMS: Mass found (+MS, 333)

Rt (min): 3.52 Area %: 93.46 (at max), 93.80 (at 254 nm).

HPLC: >93%

Rt (min): 3.49 Area %: 93.70 (at max), 93.80 (at 254 nm).

$^1$H NMR (400 MHz, DMSO-d6): δ 9.26-9.26 (m, 1H), 8.67 (d, J=2.88 Hz, 1H), 8.33-8.29 (m, 1H), 8.22-8.19 (m, 2H), 7.46-7.42 (m, 2H), 7.25 (dd, J=8.26, 1.80 Hz, 1H), 6.56 (d, J=5.84 Hz, 1H), 4.67 (s, 2H).

34

Morpholin-4-yl-{5-[4-(3-pyrazol-1-yl-benzylamino)-pyrimidin-2-yl]-pyridin-3-yl}-methanone

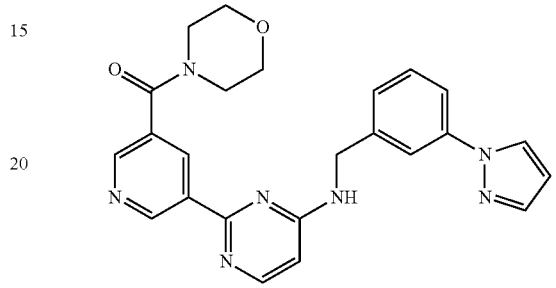

Yield: 14.77%

TLC: CHCl3/MeOH (9/1): $R_f$: 0.3

LCMS: Mass found (+MS, 442)

Rt (min): 2.63 Area %: 99.55 (at max), 99.30 (at 254 nm).

HPLC: >98%

Rt (min): 2.60 Area %: 98.79 (at max), 99.22 (at 254 nm).

$^1$H NMR (400 MHz, DMSO-d6): δ 9.45 (d, J=1.96 Hz, 1H), 8.68 (d, J=1.60 Hz, 1H), 8.53 (s, 1H), 8.46 (d, J=2.48 Hz, 1H), 8.25-8.15 (m, 2H), 7.90 (s, 1H), 7.71-7.69 (m, 2H), 7.44 (t, J=7.88 Hz, 1H), 7.32 (d, J=7.60 Hz, 1H), 6.58 (d, J=3.52 Hz, 1H), 6.52-6.51 (m, 1H), 4.74 (s, 2H), 3.64-3.51 (m, 8H).

35

(4-Chloro-2-fluoro-benzyl)-[2-(5-trifluoromethyl-pyridin-3-yl)-pyrimidin-4-yl]-amine

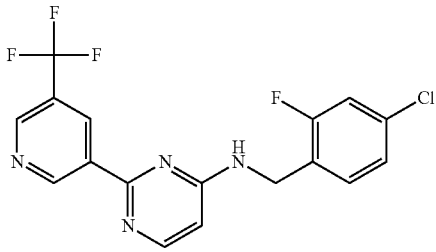 [SMILES: Fc1cc(Cl)ccc1CNc1ccnc(-c2cncc(C(F)(F)F)c2)n1]

Yield: 18.21%

TLC: Pet ether/Ethyl acetate (5/5): $R_f$: 0.4

LCMS: Mass found (+MS, 383)

Rt (min): 4.11 Area %: 99.19 (at max), 98.32 (at 254 nm).

HPLC: >99%

Rt (min): 4.10 Area %: 99.66 (at max), 99.33 (at 254 nm).

¹H NMR (400 MHz, DMSO-d6): δ 9.63 (s, 1H), 9.10 (s, 1H), 8.76 (s, 1H), 8.54 (s, 1H), 8.25 (d, J=5.52 Hz, 1H), 7.48-7.41 (m, 2H), 7.25 (d, J=8.04 Hz, 1H), 6.64 (d, J=6.04 Hz, 1H), 4.68 (s, 2H).

36

[2-(5-Chloro-pyridin-3-yl)-pyrimidin-4-yl]-cyclopropylmethyl-amine

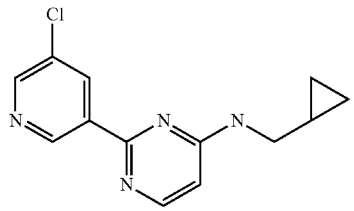 [SMILES: Clc1cncc(-c2nccc(NCC3CC3)n2)c1]

Yield: 12.20%

TLC: Pet ether/Ethyl acetate (5/5): $R_f$: 0.4

LCMS: Mass found (+MS, 261)

Rt (min): 2.88 Area %: 98.18 (at max), 97.74 (at 254 nm).

HPLC: >98%

Rt (min): 2.90 Area %: 98.87 (at max), 98.03 (at 254 nm).

¹H NMR (400 MHz, DMSO-d6): δ 9.35 (d, J=1.20 Hz, 1H), 8.72 (d, J=2.44 Hz, 1H), 8.57-8.55 (m, 1H), 8.16 (brs, 1H), 7.75 (brs, 1H), 6.50 (d, J=5.80 Hz, 1H), 1.09-1.07 (m, 1H), 0.50-0.45 (m, 2H), 0.28-0.25 (m, 2H).

¹H NMR (400 MHz, DMSO-d6, D₂O): δ 9.32 (d, J=1.44 Hz, 1H), 8.69 (d, J=2.44 Hz, 1H), 8.55-8.54 (m, 1H), 8.13 (brs, 1H), 6.48 (d, J=5.84 Hz, 1H), 3.28 (s, 2H), 1.06-1.05 (m, 1H), 0.48-0.43 (m, 2H), 0.26-0.22 (m, 2H).

37

[2-(5-Chloro-pyridin-3-yl)-pyrimidin-4-yl]-cyclohexylmethyl-amine

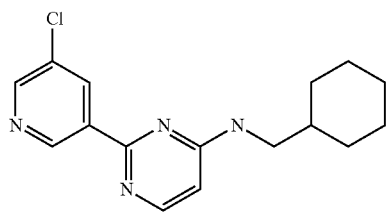 [SMILES: Clc1cncc(-c2nccc(NCC3CCCCC3)n2)c1]

Yield: 17.29%

TLC: Pet ether/Ethyl acetate (5/5): $R_f$: 0.4

LCMS: Mass found (+MS, 303)

Rt (min): 3.92 Area %: 99.34 (at max), 99.56 (at 254 nm).

HPLC: >97%

Rt (min): 3.89 Area %: 97.87 (at max), 99.56 (at 254 nm).

¹H NMR (400 MHz, DMSO-d6): δ 9.34 (s, 1H), 8.72 (d, J=2.48 Hz, 1H), 8.55-8.54 (m, 1H), 8.12 (d, J=5.76 Hz, 1H), 7.66-7.65 (m, 1H), 6.48 (d, J=5.88 Hz, 1H), 3.32-3.28 (m, 2H), 1.77-1.67 (m, 4H), 1.62-1.60 (m, 2H), 1.24-1.12 (m, 3H), 1.02-0.93 (m, 2H).

38

[2-(5-Chloro-pyridin-3-yl)-pyrimidin-4-yl]-(2-fluoro-benzyl)-amine

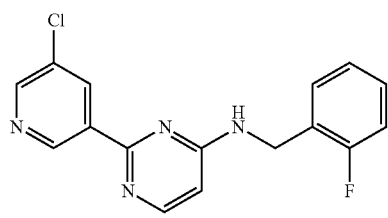 [SMILES: Fc1ccccc1CNc1ccnc(-c2cncc(Cl)c2)n1]

Yield: 20.18%

TLC: Pet ether/Ethyl acetate (6/4): $R_f$: 0.3

LCMS: Mass found (+MS, 315)

Rt (min): 3.34 Area %: 99.20 (at max), 99.59 (at 254 nm).

HPLC: >99%

Rt (min): 3.32 Area %: 99.16 (at max), 99.38 (at 254 nm).

¹H NMR (400 MHz, DMSO-d6): δ 9.32 (s, 1H), 8.71 (d, J=2.08 Hz, 1H), 8.54 (s, 1H), 8.19 (brs, 2H), 7.43 (t, J=7.48 Hz, 1H), 7.32-7.28 (m, 1H), 7.23-7.14 (m, 2H), 6.57 (d, J=5.84 Hz, 1H), 4.68 (s, 2H).

39

[2-(5-Chloro-pyridin-3-yl)-pyrimidin-4-yl]-(4-fluoro-benzyl)-amine

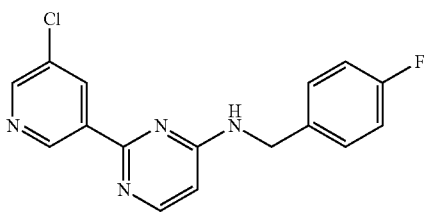 [SMILES: Fc1ccc(CNc2ccnc(-c3cncc(Cl)c3)n2)cc1]

Yield: 11.09%

TLC: Pet ether/Ethyl acetate (6/4): $R_f$: 0.3

LCMS: Mass found (+MS, 315)

Rt (min): 3.35 Area %: 97.23 (at max), 98.28 (at 254 nm).

HPLC: >97%

Rt (min): 3.40 Area %: 97.29 (at max), 98.95 (at 254 nm).

¹H NMR (400 MHz, DMSO-d6): δ 9.32 (d, J=1.56 Hz, 1H), 8.71 (d, J=2.24 Hz, 1H), 8.53 (s, 1H), 8.21 (s, 2H), 7.43-7.40 (m, 2H), 7.18-7.13 (m, 2H), 6.55 (d, J=4.88 Hz, 1H), 4.64 (brs, 2H).

40

(5-{4-[(2,2-Dimethyl-2,3-dihydro-benzofuran-7-ylmethyl)-amino]-pyrimidin-2-yl}-pyridin-3-yl)-morpholin-4-yl-methanone

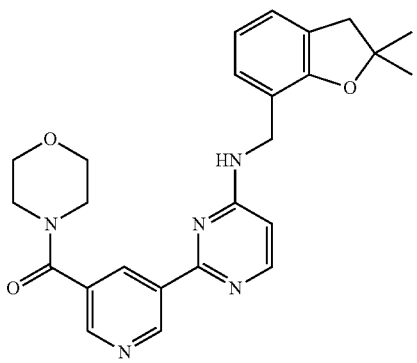 [SMILES: CC1(C)Cc2cccc(CNc3ccnc(-c4cncc(C(=O)N5CCOCC5)c4)n3)c2O1]

Yield: 7.81%
TLC: CHCl3/MeOH (9.5/0.5): $R_f$: 0.5
LCMS: Mass found (+MS, 446.3)
Rt (min): 3.21 Area %: 97.75 (at max), 97.85 (at 254 nm).
HPLC: >98%
Rt (min): 3.20 Area %: 98.19 (at max), 97.78 (at 254 nm).
¹H NMR (400 MHz, DMSO-d6): δ 9.41 (s, 1H), 8.52-8.51 (m, 1H), 8.22 (d, J=6.00 Hz, 1H), 7.08 (d, J=7.16 Hz, 2H), 6.75 (t, J=8.56 Hz, 1H), 6.66 (d, J=6.36 Hz, 1H), 4.60 (s, 2H), 3.65-3.54 (m, 6H), 3.00 (s, 2H), 1.42 (s, 6H).

Synthesis Intermediates for Amido Substituted Azaheterocyclic Compounds

2-Chloro-6-(2,4-difluoro-benzylamino)-pyrimidine-4-carboxylic acid methyl ester

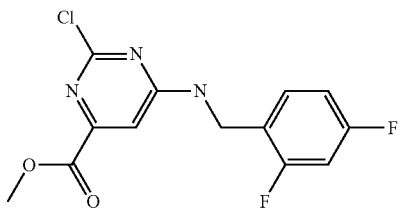 [SMILES: COC(=O)c1cc(NCc2ccc(F)cc2F)nc(Cl)n1]

A suspension of methyl 2,6-dichloropyrimidine-4-carboxylate (1 g, 4.87 mmol) in methanol (20 ml) was cooled to −20° C., to this 2,4-difluoro benzylamine (0.627 mg, 4.39 mmol) and triethylamine (0.98 mg, 9.74 mmol) were added. The reaction mixture was stirred at same temperature for 1 hr then at room temperature for 4 hrs. Methanol was removed under vacuum. The residue was purified by column chromatography to get the title compound.

Yield: 45.93%
TLC: Pet ether/Ethyl acetate (7/3): $R_f$: 0.4
LCMS: Mass found (+MS, 314.0)
Rt (min): 4.16 Area %: 97.75 (at max), 98.54 (at 254 nm)
HPLC: >99%
Rt (min): 4.23 Area %: 99.27 (at max), 98.66 (at 254 nm)
¹H NMR (400 MHz, DMSO-d6): δ 8.79-8.76 (m, 1H), 7.47-7.41 (m, 1H), 7.30-7.24 (m, 1H), 7.12 (s, 1H), 7.10-7.05 (m, 1H), 4.71 (d, J=5.52 Hz, 2H), 3.83 (s, 3H).

A13

6-(2,4-Difluoro-benzylamino)-2-(5-trifluoromethyl-pyridin-3-yl)-pyrimidine-4-carboxylic acid methyl ester

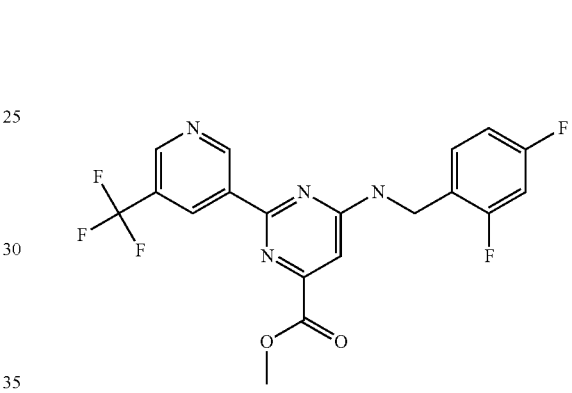

To a 20 ml microwave vial with stir bar was added the 2-Chloro-6-(2,4-difluoro-benzylamino)-pyrimidine-4-carboxylic acid methyl ester, the pyrimidine from above (500 mg, 1.597 mmol), 5-trifluoromethylpyridine 3-boronic acid (566.9 mg, 2.076 mmol), palladium acetate (17.9 mg, 0.0798 mmol), 2-dicyclohexylphosphino-2',6'-dimethoxybiphenyl (98.2 mg, 0.239 mmol) and potassium carbonate (661 mg, 4.791 mmol). Reagents were suspended in dioxane (10 ml)/water (1 ml) and run in microwave reactor at 120° C. for 30 minutes. The reaction was cooled to room temperature, diluted with water (60 ml) and EtOAc (100 ml) and extracted with EtOAc (50 ml). The combined organic layer was washed with water (100 ml) and brine solution then dried over anhydrous sodium sulphate and evaporated. The residue was purified by column chromatography to get the title compound.

Yield: 44.31%
TLC: Pet ether/Ethyl acetate (7/3): $R_f$: 0.4
LCMS: Mass found (+MS, 425.0)
Rt (min): 5.08 Area %: 94.29 (at max), 96.71 (at 254 nm).
HPLC: >98%
Rt (min): 5.08 Area %: 98.15 (at max), 98.80 (at 254 nm).
¹H NMR (400 MHz, DMSO-d6): δ 9.67 (d, J=1.52 Hz, 1H), 9.10 (d, J=1.32 Hz, 1H), 8.77 (s, 1H), 8.66 (t, J=5.72 Hz, 1H), 7.54-7.48 (m, 1H), 7.27-7.20 (m, 2H), 7.07-7.04 (m, 1H), 4.71 (d, J=5.48 Hz, 2H), 3.89 (s, 3H).

A14

6-(2,4-Difluoro-benzylamino)-2-(5-trifluoromethyl-pyridin-3-yl)-pyrimidine-4-carboxylic acid

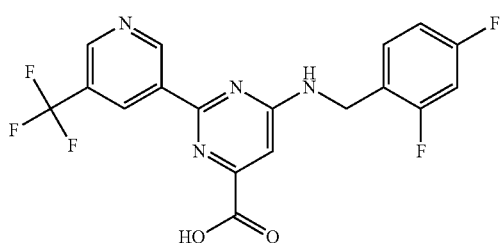 [SMILES: O=C(O)c1cc(NCc2ccc(F)cc2F)nc(-c2cncc(C(F)(F)F)c2)n1]

A solution of methyl 6-(2,4-Difluoro-benzylamino)-2-(5-trifluoromethyl-pyridin-3-yl)-pyrimidine-4-carboxylic acid methyl ester (1 g, 0.0023 mol) in THF (10 ml), MeOH (10 ml) and H$_2$O (10 ml) was added LiOH (0.198 g, 0.0047 mol) and the reaction mixture was stirred at room temperature for 2 hours. The reaction mixture was concentrated in vacuum, reaction mass was diluted with water and neutralized with 5% citric acid solution. The obtained precipitate was filtered and washed with water, dried well under vacuum to get the title compound as a white solid.

Yield: 95.44%

TLC: CHCl3/MeOH (9/1): R$_f$: 0.3

LCMS: Mass found (+MS, 411.0)

Rt (min): 4.47 Area %: 98.02 (at max), 99.15 (at 254 nm).

HPLC: >98%

Rt (min): 4.46 Area %: 98.29 (at max), 98.61 (at 254 nm).

$^1$H NMR (400 MHz, DMSO-d6): δ 9.72 (d, J=1.6 Hz, 1H), 9.08 (d, J=1.40 Hz, 1H), 8.89 (s, 1H), 8.58 (s, 1H), 7.53-7.47 (m, 1H), 7.27-7.21 (m, 1H), 7.15 (s, 1H), 7.07-7.03 (m, 1H), 4.71 (d, J=5.00 Hz, 2H).

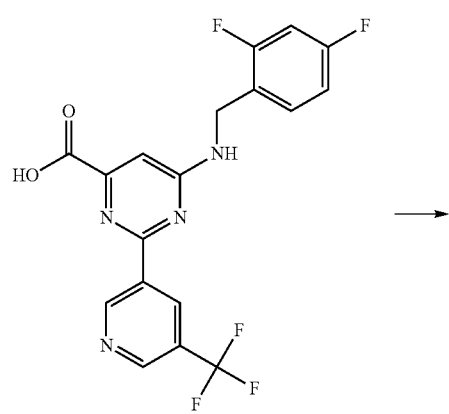

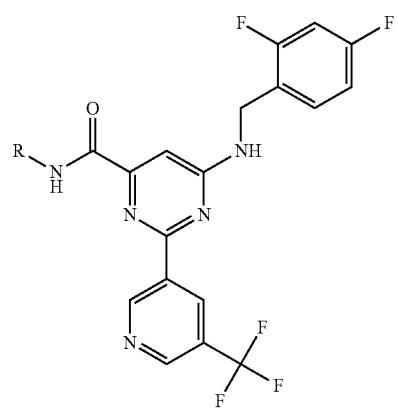

A solution of 6-[(2,4-difluorobenzyl)amino]-2-[5-(trifluoromethyl)pyridin-3-yl]pyrimidine-4-carboxylic acid (1 equiv) in 10 ml dichloromethane was mixed with R—NH2 (1.2 equiv) and Et$_3$N (3 equiv). T3P (3 equiv) was added to the reaction mixture at 0° C. The reaction mixture was stirred at room temperature for 12 hours. The reaction mixture was diluted with dichloromethane (20 ml) and washed with water (1×20 ml), followed by brine solution (1×20 ml), then dried over anhydrous sodium sulphate, filtered and evaporated. The residue was purified by column chromatography on silica gel to get the required product.

Examples of Amido Substituted Azaheterocyclic Compounds

41

6-(2,4-Difluoro-benzylamino)-2-(5-trifluoromethyl-pyridin-3-yl)-pyrimidine-4-carboxylic acid (2-carbamoyl-ethyl)-amide

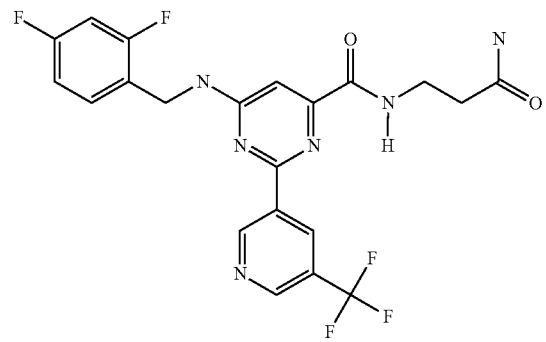 [SMILES: NC(=O)CCNC(=O)c1cc(NCc2ccc(F)cc2F)nc(-c2cncc(C(F)(F)F)c2)n1]

Yield: 33.90%

$^1$H NMR (400 MHz, DMSO): δ 9.92 (s, 1H), 9.19-9.17 (m, 1H), 9.10 (s, 1H), 8.97 (s, 1H), 8.62-8.59 (m, 1H), 7.52-7.46 (m, 1H), 7.40 (s, 1H), 7.25-7.20 (m, 1H), 7.17 (s, 1H), 7.06-

7.02 (m, 1H), 6.89 (s, 1H), 4.71 (d, J=5.36 Hz, 2H), 3.52-3.47 (m, 2H), 2.38 (t, J=7.20 Hz, 2H).

42

6-(2,4-Difluoro-benzylamino)-2-(5-trifluoromethyl-pyridin-3-yl)-pyrimidine-4-carboxylic acid (2-diethylcarbamoyl-ethyl)-amide

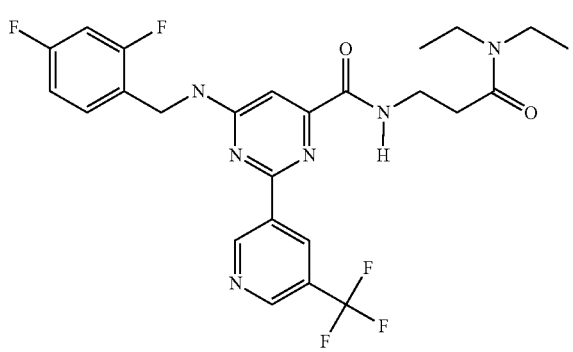

Yield: 44.96%

¹H NMR (400 MHz, DMSO-d6): δ 9.90 (s, 1H), 9.20-9.17 (m, 1H), 9.10 (s, 1H), 8.97 (s, 1H), 8.63-8.60 (m, 1H), 7.53-7.47 (m, 1H), 7.26-7.21 (m, 1H), 7.17 (s, 1H), 7.06-7.02 (m, 1H), 4.71 (d, J=5.28 Hz, 2H), 3.53-3.52 (m, 2H), 3.30-3.26 (m, 4H), 2.60 (t, J=7.16 Hz, 2H), 1.08 (t, J=7.16 Hz, 3H), 1.00 (t, J=8.92 Hz, 3H).

43

6-(2,4-Difluoro-benzylamino)-2-(5-trifluoromethyl-pyridin-3-yl)-pyrimidine-4-carboxylic acid (3-morpholin-4-yl-3-oxo-propyl)-amide

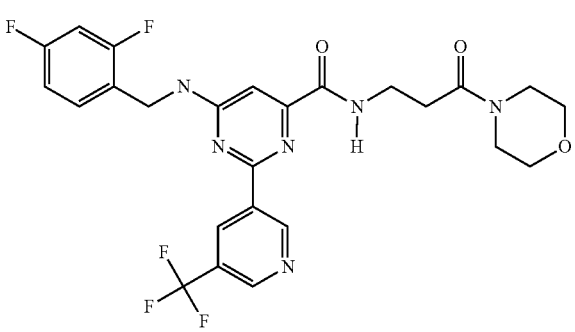 [SMILES: O=C(NCCC(=O)N1CCOCC1)c1cc(NCc2ccc(F)cc2F)nc(-c2cncc(C(F)(F)F)c2)n1]

Yield: 31.52%

¹H NMR (400 MHz, DMSO-d6): δ 9.91 (s, 1H), 9.18 (t, J=6.2 Hz, 1H), 9.10 (s, 1H), 8.97 (s, 1H), 8.62 (t, J=5.68 Hz, 1H), 7.52-7.47 (m, 1H), 7.26-7.21 (m, 1H), 7.17 (s, 1H), 7.06-7.02 (m, 1H), 4.71 (d, J=5.40 Hz, 2H), 3.55-3.50 (m, 6H), 3.45-3.43 (m, 4H), 2.63 (t, J=7.12 Hz, 2H).

44

6-(2,4-Difluoro-benzylamino)-2-(5-trifluoromethyl-pyridin-3-yl)-pyrimidine-4-carboxylic acid [3-(4-methyl-piperazin-1-yl)-3-oxo-propyl]-amide

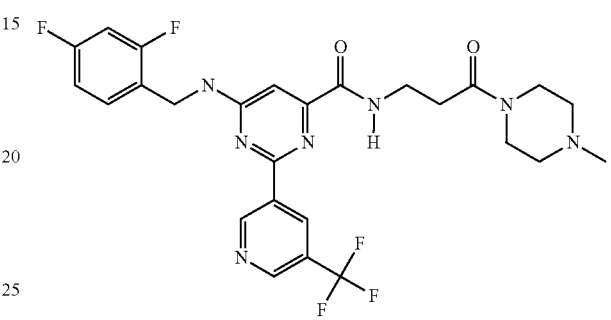

Yield: 28.71%

¹H NMR (400 MHz, DMSO-d6): δ 9.90 (s, 1H), 9.17 (t, J=6.08 Hz, 1H), 9.10 (s, 1H), 8.96 (s, 1H), 8.62 (t, J=5.56 Hz, 1H), 7.52-7.46 (m, 1H), 7.26-7.21 (m, 1H), 7.17 (s, 1H), 7.06-7.02 (m, 1H), 4.71 (d, J=5.32 Hz, 2H), 3.53-3.49 (m, 2H), 3.46-3.41 (m, 4H), 2.62 (t, J=7.04 Hz, 2H), 2.26-2.20 (m, 4H), 2.12 (s, 3H).

45

6-(2,4-Difluoro-benzylamino)-2-(5-trifluoromethyl-pyridin-3-yl)-pyrimidine-4-carboxylic acid (3-dimethylamino-propyl)-amide

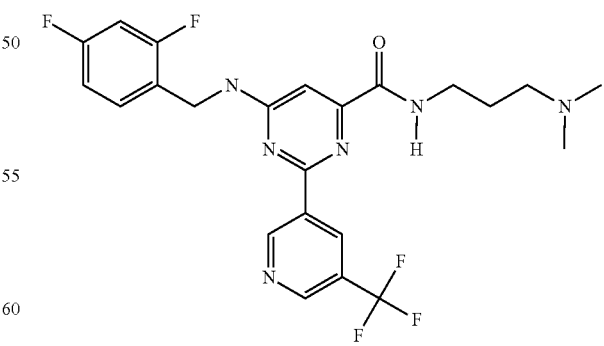

Yield: 22.77%

¹H NMR (400 MHz, DMSO-d6): δ 9.94 (s, 1H), 9.20-9.19 (m, 1H), 9.10 (s, 1H), 8.95 (s, 1H), 8.62-8.60 (m, 1H), 7.52-7.46 (m, 1H), 7.26-7.21 (m, 1H), 7.18 (s, 1H), 7.06-7.02 (m,

1H), 4.70 (d, J=5.32 Hz, 2H), 3.37-3.32 (m, 2H), 2.39 (s, 2H), 2.23 (s, 6H), 1.72-1.69 (m, 2H).

46

6-(2,4-Difluoro-benzylamino)-2-(5-trifluoromethyl-pyridin-3-yl)-pyrimidine-4-carboxylic acid (3-imidazol-1-yl-propyl)-amide

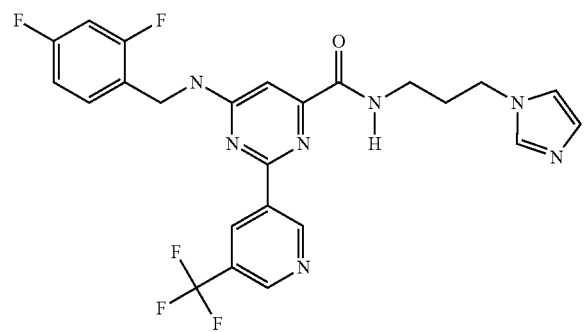 [SMILES: O=C(NCCCn1ccnc1)c1cc(NCc2ccc(F)cc2F)nc(-c2cncc(C(F)(F)F)c2)n1]

Yield: 58.05%

$^1$H NMR (400 MHz, DMSO-d6): δ 9.97 (s, 1H), 9.14 (t, J=6.08 Hz, 1H), 9.10 (s, 1H), 8.99 (s, 1H), 8.60 (t, J=5.68 Hz, 1H), 7.66 (s, 1H), 7.52-7.46 (m, 1H), 7.26-7.18 (m, 3H), 7.06-7.02 (m, 1H), 6.88 (s, 1H), 4.71 (d, J=5.36 Hz, 2H), 4.00 (t, J=6.84 Hz, 2H), 3.33-3.29 (m, 2H), 2.02-1.95 (m, 2H).

47

6-(2,4-Difluoro-benzylamino)-2-(5-trifluoromethyl-pyridin-3-yl)-pyrimidine-4-carboxylic acid [3-(2-oxo-pyrrolidin-1-yl)-propyl]-amide

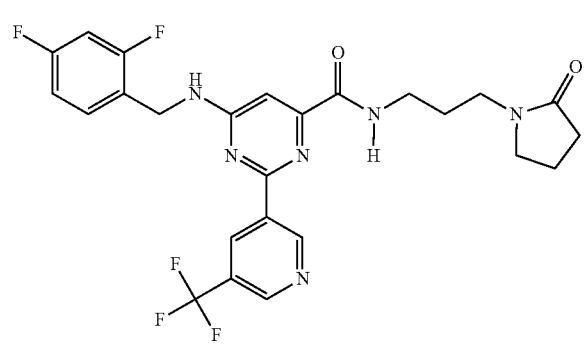 [SMILES: O=C(NCCCN1CCCC1=O)c1cc(NCc2ccc(F)cc2F)nc(-c2cncc(C(F)(F)F)c2)n1]

Yield: 67.63%

$^1$H NMR (400 MHz, DMSO-d6): δ 9.95 (s, 1H), 9.23 (t, J=6.08 Hz, 1H), 9.10 (d, J=5.64 Hz, 2H), 8.60 (t, J=4.92 Hz, 1H), 7.53-7.47 (m, 1H), 7.26-7.21 (m, 1H), 7.17 (s, 1H), 7.06-7.02 (m, 1H), 4.71 (d, J=4.96 Hz, 2H), 3.37-3.32 (m, 2H), 3.28-3.24 (m, 4H), 2.32-2.31 (m, 2H), 1.96-1.89 (m, 2H), 1.71-1.68 (m, 2H).

48

6-(2,4-Difluoro-benzylamino)-2-(5-trifluoromethyl-pyridin-3-yl)-pyrimidine-4-carboxylic acid (3-morpholin-4-yl-propyl)-amide Yield: 54.12%

$^1$H NMR (400 MHz, CD3OD): δ 9.84 (s, 1H), 9.12 (s, 1H), 8.97 (s, 1H), 7.51-7.46 (m, 1H), 7.19 (s, 1H), 7.00-6.90 (m, 2H), 4.77 (s, 2H), 3.69 (t, J=4.68 Hz, 4H), 3.50 (t, J=6.92 Hz, 2H), 2.50-2.46 (m, 6H), 1.91-1.84 (m, 2H).

49

1-[6-(2,4-Difluoro-benzylamino)-2-(5-trifluoromethyl-pyridin-3-yl)-pyrimidine-4-carbonyl]-piperidine-4-carboxylic acid amide

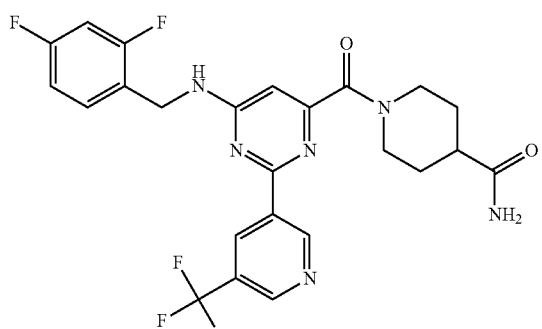

Yield: 42.56%

$^1$H NMR (400 MHz, DMSO-d6): δ 9.64 (d, J=1.28 Hz, 1H), 9.10 (s, 1H), 8.75 (s, 1H), 8.50-8.47 (m, 1H), 7.53-7.51 (m, 1H), 7.31 (s, 1H), 7.27-7.21 (m, 1H), 7.08-7.03 (m, 1H), 6.82 (s, 1H), 6.65 (s, 1H), 4.69 (brs, 2H), 4.41 (d, J=12.92 Hz, 1H), 3.79 (d, J=12.60 Hz, 1H), 3.09-3.03 (m, 1H), 2.87-2.80 (m, 1H), 2.43-2.36 (m, 1H), 1.81-1.52 (m, 4H).

50

1-[6-(2,4-Difluoro-benzylamino)-2-(5-trifluoromethyl-pyridin-3-yl)-pyrimidine-4-carbonyl]-piperidine-3-carboxylic acid amide

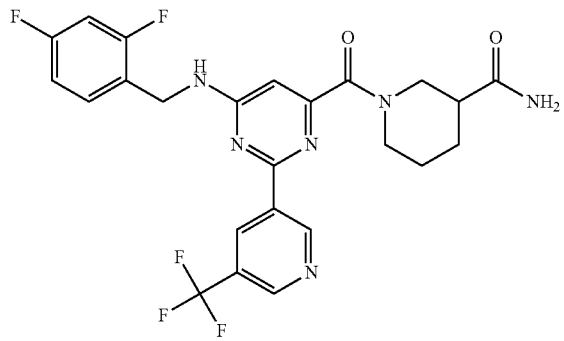 [SMILES: NC(=O)C1CCCN(C(=O)c2cc(NCc3ccc(F)cc3F)nc(-c3cncc(C(F)(F)F)c3)n2)C1]

Yield: 48.26%

$^1$H NMR (400 MHz, DMSO-d6): δ 9.64 (s, 1H), 9.10 (s, 1H), 8.74 (s, 1H), 8.49-8.48 (m, 1H), 7.52-7.51 (m, 1H), 7.42-7.21 (m, 2H), 7.05 (t, J=8.52 Hz, 1H), 6.92-6.81 (m, 1H), 6.65 (d, J=10.84 Hz, 1H), 4.70-4.69 (m, 2H), 4.49-4.30 (m, 1H), 3.85-3.70 (m, 1H), 3.20-2.97 (m, 1H), 2.82 (t, J=14.00 Hz, 1H), 2.40-2.31 (m, 1H), 2.01-1.90 (m, 1H), 1.79-1.53 (m, 2H), 1.45-1.42 (m, 1H).

51

6-(2,4-Difluoro-benzylamino)-2-(5-trifluoromethyl-pyridin-3-yl)-pyrimidine-4-carboxylic acid (1-methyl-pyrrolidin-3-ylmethyl)-amide

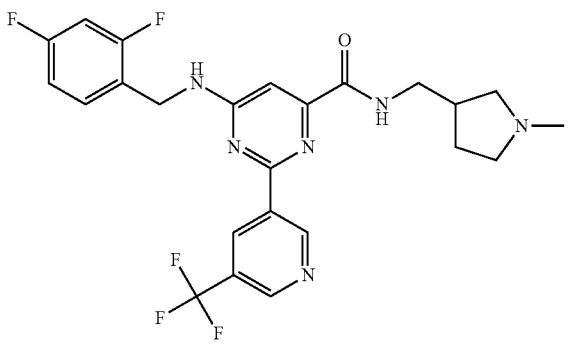 [SMILES: CN1CCC(CNC(=O)c2cc(NCc3ccc(F)cc3F)nc(-c3cncc(C(F)(F)F)c3)n2)C1]

Yield: 40.23%

$^1$H NMR (400 MHz, DMSO-d6): δ 9.97 (s, 1H), 9.21 (t, J=5.56 Hz, 1H), 9.10 (s, 1H), 8.96 (s, 1H), 8.63 (t, J=5.72 Hz, 1H), 7.52-7.46 (m, 1H), 7.26-7.20 (m, 1H), 7.18 (s, 1H), 7.06-7.02 (m, 1H), 4.70 (d, J=5.36 Hz, 2H), 3.33 (brs, 2H), 2.85-2.81 (m, 2H), 2.67-2.66 (m, 2H), 2.60-2.56 (m, 1H), 2.50-2.47 (m, 3H), 1.99-1.90 (m, 1H), 1.65-1.57 (m, 1H).

52

6-(2,4-Difluoro-benzylamino)-2-(5-trifluoromethyl-pyridin-3-yl)-pyrimidine-4-carboxylic acid [2-(1H-imidazol-4-yl)-ethyl]-amide

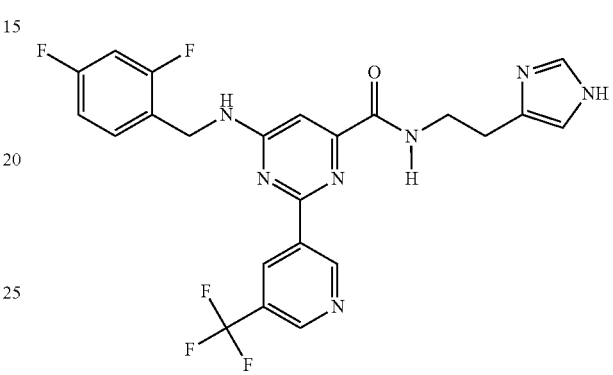

Yield: 61.30%

$^1$H NMR (400 MHz, DMSO-d6): δ 11.90 (brs, 1H), 9.97 (s, 1H), 9.37 (s, 1H), 9.10 (s, 1H), 8.99 (s, 1H), 8.60 (t, J=5.44 Hz, 1H), 7.57 (s, 1H), 7.52-7.47 (m, 1H), 7.26-7.18 (m, 2H), 7.06-7.02 (m, 1H), 6.88 (s, 1H), 4.71 (d, J=5.20 Hz, 2H), 3.56-3.51 (m, 2H), 2.78 (t, J=7.2 Hz, 2H).

53

6-(2,4-Difluoro-benzylamino)-2-(5-trifluoromethyl-pyridin-3-yl)-pyrimidine-4-carboxylic acid (4-dimethylamino-butyl)-amide

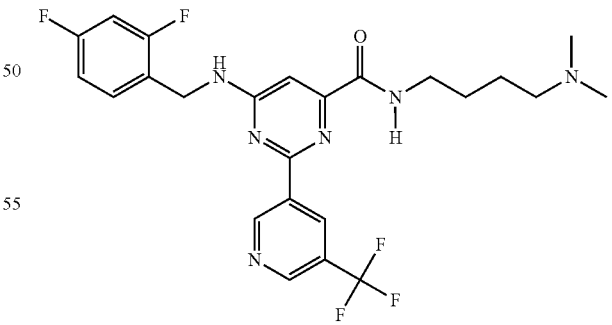

Yield: 59.52%

$^1$H NMR (400 MHz, DMSO-d6, D2O): δ 9.91 (s, 1H), 9.07 (s, 1H), 8.97 (s, 1H), 7.50-7.44 (m, 1H), 7.21-7.15 (m, 2H), 7.04-6.99 (m, 1H), 4.67 (s, 2H), 3.30 (t, J=7.00 Hz, 2H), 2.43-2.39 (m, 2H), 2.24 (s, 6H), 1.55-1.45 (m, 4H).

54

6-(2,4-Difluoro-benzylamino)-2-(5-trifluoromethyl-pyridin-3-yl)-pyrimidine-4-carboxylic acid (1-methyl-piperidin-4-yl)-amide

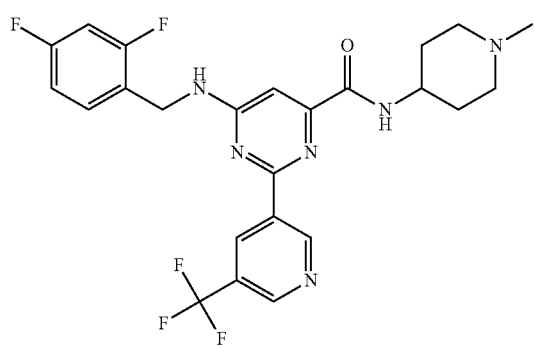 [SMILES: CN1CCC(NC(=O)c2cc(NCc3ccc(F)cc3F)nc(-c3cncc(C(F)(F)F)c3)n2)CC1]

Yield: 14.13%

¹H NMR (400 MHz, DMSO-d6): δ 10.02 (s, 1H), 9.11 (s, 1H), 8.92 (s, 1H), 8.73 (d, J=8.08 Hz, 1H), 8.60 (t, J=5.12 Hz, 1H), 7.51-7.45 (m, 1H), 7.26-7.18 (m, 2H), 7.06-7.02 (m, 1H), 4.70 (d, J=5.40 Hz, 2H), 3.80-3.78 (m, 1H), 2.82 (brs, 2H), 2.21 (s, 3H), 2.02 (brs, 2H), 1.80-1.74 (m, 4H).

Synthesis Intermediates for Amine Substituted Azaheterocyclic Compounds (2,6-Dichloro-pyrimidin-4-yl)-(2,4-difluoro-benzyl)-amine

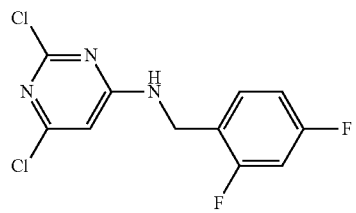 [SMILES: Fc1ccc(CNc2cc(Cl)nc(Cl)n2)c(F)c1]

A suspension of methyl 2,4,6-trichloropyrimidine (1 g, 4.87 mmol) in methanol (20 ml) was cooled –20° C., to this 2,4-difluoro benzylamine (0.627 mg, 4.39 mmol) and triethylamine (0.98 mg, 9.74 mmol) were added. RM was stirred at same temperature for 1 hr then at room temperature for 4 hrs. Methanol was removed under vacuum. The residue was purified by column chromatography to get the title compound.

Yield: 37.97%

TLC: Pet ether/Ethyl acetate (8/2): R_f: 0.4

LCMS: Mass found (+MS, 290.0)

Rt (min): 4.74 Area %: 97.36 (at max), 99.51 (at 254 nm)

HPLC: >99%

Rt (min): 4.81 Area %: 99.61 (at max), 99.49 (at 254 nm)

¹H NMR (400 MHz, DMSO-d6): δ 8.65-8.63 (m, 1H), 7.46-7.40 (m, 1H), 7.29-7.24 (m, 1H), 7.10-7.05 (m, 1H), 6.57 (s, 1H), 4.52-4.44 (m, 2H).

[6-Chloro-2-(5-trifluoromethyl-pyridin-3-yl)-pyrimidin-4-yl]-(2,4-difluoro-benzyl)-amine

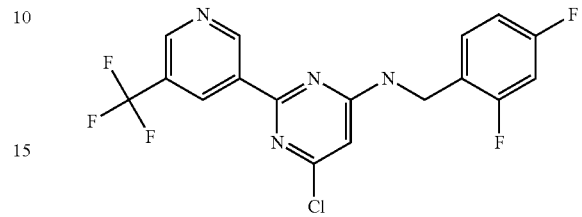

A mixture of (2,6-Dichloro-pyrimidin-4-yl)-(2,4-difluoro-benzyl)-amine (1 g, 0.0034 mol) and 5-trifluoromethylpyridine-3-boronic acid (0.726 g, 0.0038 mol) were taken in dioxane:water (20:5) ml and to this CsF (2.1 g, 0.0138 mol) was added and degassed. Then bis-triphenylphosphine-palladium(II) chloride (0.24 g, 0.00034 mol) was added and degassed. The mixture was stirred at 60° C. for 12 hrs. The reaction was cooled to room temperature diluted with water (50 ml) and ethyl acetate (100 ml). After standard work-up, the residue was purified by column chromatography to get compound as white solid.

Yield: 21.73%

TLC: Pet ether/Ethyl acetate (8/2): R_f: 0.4

LCMS: Mass found (+MS, 401.0)

Rt (min): 5.70 Area %: 98.35 (at max), 95.87 (at 254 nm)

HPLC: >97%

Rt (min): 5.79 Area %: 98.74 (at max), 97.70 (at 254 nm)

¹H NMR (400 MHz, DMSO-d6): δ 9.61 (s, 1H), 9.12 (s, 1H), 8.75-8.71 (m, 1H), 8.53 (t, J=4.92 Hz, 1H), 7.53-7.47 (m, 1H), 7.27-7.21 (m, 1H), 7.07-7.03 (m, 1H), 6.63 (s, 1H), 4.69 (d, J=5.36 Hz, 2H).

Example of an Amine Substituted Azaheterocyclic Compound

55

1-[6-(2,4-Difluoro-benzylamino)-2-(5-trifluoromethyl-pyridin-3-yl)-pyrimidin-4-yl]-piperidine-3-carboxylic acid amide

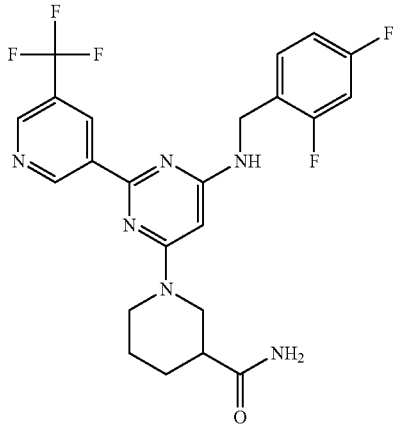 [SMILES: NC(=O)C1CCCN(c2cc(NCc3ccc(F)cc3F)nc(-c3cncc(C(F)(F)F)c3)n2)C1]

[6-Chloro-2-(5-trifluoromethyl-pyridin-3-yl)-pyrimidin-4-yl]-(2,4-difluoro-benzyl)-amine (80 mg, 0.199 mmol) was taken in pressure tube, to this amine (101 mg, 0.796 mmol) was added and the reaction mixture was stirred at 120° C. for 12 hours. The reaction mixture was diluted with 10% NaHCO3 (20 ml) solution and ethyl acetate (50 ml), organic layer was separated washed with 10% citric acid solution (20 ml), water (20 ml), brine solution. The combined extract was dried over anhydrous sodium sulphate, filtered and evaporated. The residue was purified by column chromatography to get compound as white solid.

Yield: 20.80%

TLC: CHCl3/MeOH (9/1): $R_f$: 0.4

LCMS: Mass found (+MS, 493.0)

Rt (min): 4.07 Area %: 97.80 (at max), 96.94 (at 254 nm).

HPLC: >96%

Rt (min): 4.03 Area %: 97.81 (at max), 96.66 (at 254 nm).

$^1$H NMR (400 MHz, DMSO-d6): δ 9.63 (d, J=1.64 Hz, 1H), 9.03 (d, J=1.40 Hz, 1H), 8.72 (s, 1H), 7.51-7.47 (m, 1H), 7.45-7.41 (m, 1H), 7.38 (s, 1H), 7.22-7.17 (m, 1H), 7.05-7.01 (m, 1H), 6.88 (s, 1H), 5.76 (s, 1H), 4.56 (s, 2H), 4.45-4.20 (m, 2H), 2.96-2.82 (m, 2H), 2.32-2.26 (m, 1H), 1.90-1.87 (m, 1H), 1.73-1.70 (m, 1H), 1.66-1.55 (m, 1H), 1.49-1.36 (m, 1H).

Biological Activity

1. Biochemical Enzyme Assays for FAK Activity

The FAK assays described here are performed on two Caliper Life Sciences systems, the LC3000 and the EZ Reader II. These provide data on enzyme activity via measurement of the relative amounts of phosphorylated or unphosphorylated fluorescently labelled substrate peptide at the end of an enzymatic reaction. These different states of peptide are resolved by applying a potential difference across the sample. The presence of the charged phosphate group on the product (as opposed to the substrate) causes different peptide mobility between the two peptides. This is visualized by excitation of the fluorescent label on the substrate and product peptides and represented as peaks within the analysis software.

a) LC3000 Method

In order to measure inhibitor activity of FAK, inhibitors in the Caliper Life Sciences LC3000, a TTP Mosquito liquid handling instrument is used to place 0.25 ul of the appropriate concentration of inhibitor in 100% DMSO (for a dose response curve calculation) into each well of a 384-well plate. To this reaction components are added to a final volume of 25 ul:

0.067 ng/ul GST-FAK (N-terminal GST fusion with truncated human FAK (376-1052 (end) amino acids))

100 uM ATP 1 mM DTT 1 mM MgCl$_2$ 1 uM substrate peptide (sequence FITC-KGWMEDY-DYVHLQGKK-(CONH$_2$)SEQ ID NO: 1))

1 mM FERM peptide (sequence NH2-GATQSFIIR-COOH (SEQ ID NO: 2))

100 mM HEPES pH 7.5

0.015% Brij-35

The reaction is incubated for 90 min at 25 C, and then stopped by the addition of 70 ul of Stop buffer (100 mM HEPES pH 7.5, 0.015% Brij-35, 10 mM EDTA).

The plate is read on a Caliper LC 3000 in an Off-Chip mobility shift assay format, using the following parameters for a 12-sipper chip: screening pressure—1.9 psi, upstream voltage—3000, downstream voltage—700. These conditions cause unphosphorylated substrate and phosphorylated product peptide to resolve as separate peaks allowing direct measurement of percentage of conversion of substrate to product. The percent conversion can be plotted against concentration of inhibitor to produce a sigmoid dose response curve, from which an IC50 can be calculated using XLFit for Microsoft Excel.

b) EZ Reader II Method

The EZ Reader II utilizes the same principle as the LC 3000 for calculating percentage conversion of a substrate to product. Caliper Life Sciences provides proprietary flash frozen pre-made 384 well plates containing selected kinases. Each column in the 384 well plate contains a particular selected kinase. A second plate, the 'substrate plate' contains a mix of fluorescently labeled peptide substrate and ATP. These are arranged in columns so that transfer for substrate plate to enzyme plate provides the correct enzyme with the correct substrate/ATP concentration. Compounds are added to a thawed enzyme plate in the desired format, in single concentrations. Reactions are initiated by transfer of the substrate/ATP mix from the substrate plate. The enzyme plate is incubated for 90 mins at 25 C. The reaction is stopped by addition of 70 ul of Stop Buffer (100 mM HEPES pH 7.5, 0.015% Brij-35, 10 mM EDTA).

Reading of the plate in the EZ Reader II is identical to the LC3000, and the ratio between substrate and product peaks provides the activity of the enzyme in that well. This is best represented by a plate heat map which colors each well by percent inhibition as compared to positive and negative controls (no inhibitors and no ATP, respectively)

2. Assay Principle for Celluar Testing of FAK Inhibitors

Cellular activity of focal adhesion kinase (FAK) is determined by the degree of FAK autophosphorylation at tyrosine 397 using a Luminex-based assay. HT29 cells are plated with 30,000 cells per well of a 96-well plate in 100 μl medium (90% DMEM/10% FCS). At the following day, test compounds are added in a serial dilution under serum-free conditions for 30 min. Then, cells were lysed with 90 μl lysis buffer (20 mM Tris/HCl pH 8.0, 150 mM NaCl, 1% NP40, 10% Glycerol, 1% Phosphatase-Inhibitor II, 20 mM □-Glycerolphosphat, 0.1% Protease-Inhibitor Cocktail III, 0.01% Benzonase) and lysates were cleared by centrifugation through a 96-well filter plate (0.65 μm). Samples were incubated with Luminex-beads which were coupled with an anti-total FAK antibody overnight at 4° C. with under gentle agitation. For detection of phospho-Y397-FAK a phospho-specific antibody and a species specific PE-labeled secondary antibody are added. The amount of phospho-Y397-FAK is determined in a Luminex100 machine measuring 100 events per well within 60 seconds.

Counts from samples treated with a FAK reference inhibitor are subtracted as pharmacological blank. Counts from samples treated with test compounds are calculated as percent of control from solvent treated (0.3% DMSO) samples. IC50 values were determined using AssayExplorer software.

To assess the inhibitory potential of the compounds, IC50-values were determined, as shown in Tables below.

Ranges for IC50 were assigned as follows: A: <0.1 μM; B: 0.100-1 μM; C: 1-10 μM; D: >10 μM TABLE 1
| | Structure | Chemical Name | FAK IC50 | HPLC Retention time [min] LCMS Mass found Yield [%] |
|---|---|---|---|---|
| 1 | 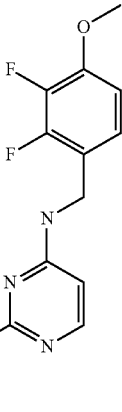 | (2,3-Difluoro-4-methoxy-benzyl)-[2-(5-methoxy-pyridin-3-yl)-pyrimidin-4-yl]-amine | C | RT: 3.17 min; Mass found[M]+: 359; Yield: 17 |
| 2 | 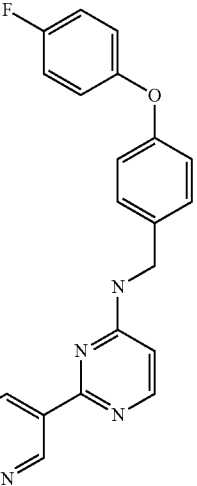 | [4-(4-Fluoro-phenoxy)-benzyl]-[2-(5-methoxy-pyridin-3-yl)-pyrimidin-4-yl]-amine | D | RT: 3.99 min; Mass found[M]+: 403.3; Yield: 25 |
| 3 | 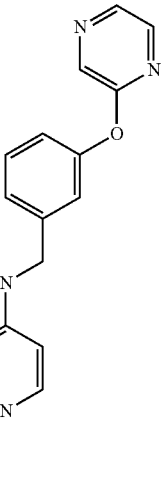 | [2-(5-Methoxy-pyridin-3-yl)-pyrimidin-4-yl]-[3-(pyrazin-2-yloxy)-benzyl]-amine | D | RT: 2.78 min; Mass found[M]+: 387.3; Yield: 24.4 |

TABLE 1-continued
| Structure | Chemical Name | FAK IC50 | HPLC Retention time [min] LCMS Mass found Yield [%] |
|---|---|---|---|
| 4 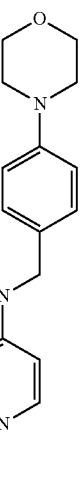 | [2-(5-Methoxy-pyridin-3-yl)-pyrimidin-4-yl]-(4-morpholin-4-yl-benzyl)-amine | D | RT: 2.21 min; Mass found[M]+: 378; Yield: 23.1 |
| 5 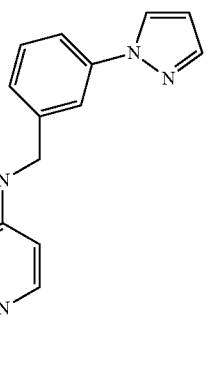 | [2-(5-Methoxy-pyridin-3-yl)-pyrimidin-4-yl]-(3-pyrazol-1-yl-benzyl)-amine | C | RT: 2.86 min; Mass found[M]+: 359.3; Yield: 9.4 |
| 6 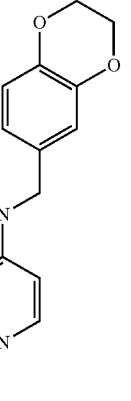 | (2,3-Dihydro-benzo[1,4]dioxin-6-ylmethyl)-[2-(5-methoxy-pyridin-3-yl)-pyrimidin-4-yl]-amine | D | RT: 2.83 min; Mass found[M]+: 351; Yield: 13.1 |

TABLE 1-continued

| Structure | Chemical Name | FAK IC50 | HPLC Retention time [min] LCMS Mass found Yield [%] |
|---|---|---|---|
| 7 | [4-(4-Fluoro-phenoxy)-benzyl]-[2-(5-fluoro-pyridin-3-yl)-pyrimidin-4-yl]-amine | D | RT: 4.12 min; Mass found[M]+: 391; Yield: 23.1 |
| 8 | (2,2-Dimethyl-2,3-dihydro-benzofuran-7-ylmethyl)-[2-(5-fluoro-pyridin-3-yl)-pyrimidin-4-yl]-amine | D | RT: 3.7 min; Mass found[M]+: 351.3; Yield: 15.7 |
| 9 | [2-(5-Fluoro-pyridin-3-yl)-pyrimidin-4-yl]-[3-(pyrazin-2-yloxy)-benzyl]-amine | D | RT: 2.89 min; Mass found[M]+: 375; Yield: 17.7 |

TABLE 1-continued

| Structure | Chemical Name | FAK IC50 | HPLC Retention time [min] LCMS Mass found Yield [%] |
|---|---|---|---|
| 10 | [2-(5-Fluoro-pyridin-3-yl)-pyrimidin-4-yl]-(4-morpholin-4-yl-benzyl)-amine | D | RT: 2.26 min; Mass found[M]+: 366; Yield: 38.1 |
| 11 | [2-(5-Fluoro-pyridin-3-yl)-pyrimidin-4-yl]-(3-pyrazol-1-yl-benzyl)-amine | D | RT: 2.98 min; Mass found[M]+: 347; Yield: 19.8 |
| 12 | (2,3-Dihydro-benzo[1,4]dioxin-6-ylmethyl)-[2-(5-fluoro-pyridin-3-yl)-pyrimidin-4-yl]-amine | D | RT: 2.94 min; Mass found[M]+: 339; Yield: 8.9 |

TABLE 1-continued

| Structure | Chemical Name | FAK IC50 | HPLC Retention time [min] LCMS Mass found Yield [%] |
|---|---|---|---|
| 13 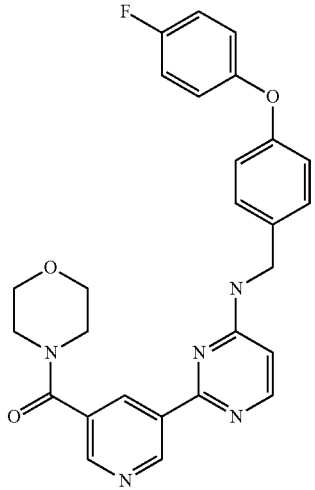 [SMILES: O=C(c1cncc(-c2nccc(NCc3ccc(Oc4ccc(F)cc4)cc3)n2)c1)N1CCOCC1] | (5-{4-[4-(4-Fluoro-phenoxy)-benzylamino]-pyrimidin-2-yl}-pyridin-3-yl)-morpholin-4-yl-methanone | D | RT: 3.7 min; Mass found[M]+: 486.3; Yield: 21.3 |
| 14 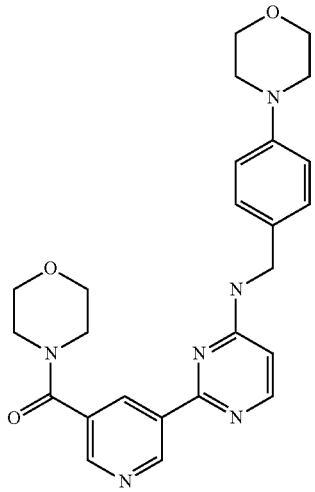 [SMILES: O=C(c1cncc(-c2nccc(NCc3ccc(N4CCOCC4)cc3)n2)c1)N1CCOCC1] | Morpholin-4-yl-{5-[4-(4-morpholin-4-yl-benzylamino)-pyrimidin-2-yl]-pyridin-3-yl}-methanone | D | RT: 2 min; Mass found[M]+: 461.2; Yield: 42.5 |
| 15 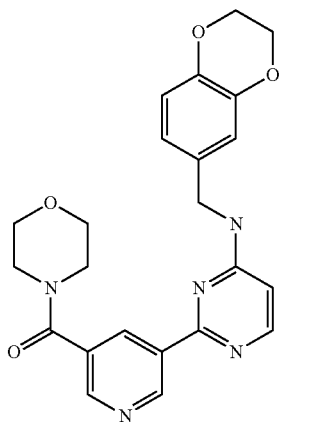 [SMILES: O=C(c1cncc(-c2nccc(NCc3ccc4c(c3)OCCO4)n2)c1)N1CCOCC1] | (5-{4-[(2,3-Dihydro-benzo[1,4]dioxin-6-ylmethyl)-amino]-pyrimidin-2-yl)-pyridin-3-yl)-morpholin-4-yl-methanone | D | RT: 2.53 min; Mass found[M]+: 434; Yield: 34.1 |

TABLE 1-continued

| Structure | Chemical Name | FAK IC50 | HPLC Retention time [min] LCMS Mass found Yield [%] |
|---|---|---|---|
| 16 | (4-Chloro-2-fluoro-benzyl)-[2-(5-methoxy-pyridin-3-yl)-pyrimidin-4-yl]-amine | B | RT: 3.35 min; Mass found[M]+: 345; Yield: 8.7 |
| 17 | (2,2-Dimethyl-2,3-dihydro-benzofuran-7-ylmethyl)-[2-(5-methoxy-pyridin-3-yl)-pyrimidin-4-yl]-amine | D | RT: 3.53 min; Mass found[M]+: 363.3; Yield: 13.8 |
| 18 | [2-(5-Chloro-pyridin-3-yl)-pyrimidin-4-yl]-(2,2-dimethyl-2,3-dihydro-benzofuran-7-ylmethyl)-amine | D | RT: 3.94 min; Mass found[M]+: 367; Yield: 14.8 |

TABLE 1-continued
| | Structure | Chemical Name | FAK IC50 | HPLC Retention time [min] LCMS Mass found Yield [%] |
|---|---|---|---|---|
| 19 | 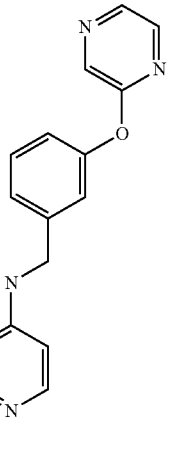 | [2-(5-Chloro-pyridin-3-yl)-pyrimidin-4-yl]-[3-(pyrazin-2-yloxy)-benzyl]-amine | D | RT: 3.1 min; Mass found[M]+: 391; Yield: 18.6 |
| 20 | 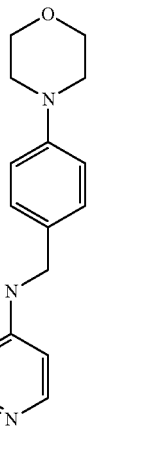 | [2-(5-Chloro-pyridin-3-yl)-pyrimidin-4-yl]-(4-morpholin-4-yl-benzyl)-amine | D | RT: 2.53 min; Mass found[M]+: 382; Yield: 4.7 |
| 21 | 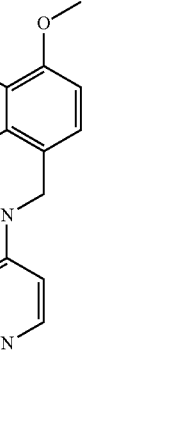 | (2,3-Difluoro-4-methoxy-benzyl)-[2-(5-fluoro-pyridin-3-yl)-pyrimidin-4-yl]-amine | C | RT: 3.25 min; Mass found [M]+: 347; Yield: 14.2 |

TABLE 1-continued

| Structure | Chemical Name | FAK IC50 | HPLC Retention time [min] LCMS Mass found Yield [%] |
|---|---|---|---|
| 22 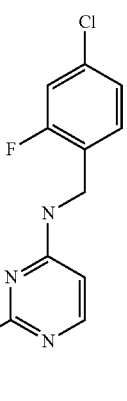 | {5-[4-(4-Chloro-2-fluoro-benzylamino)-pyrimidin-2-yl]-pyridin-3-yl}-morpholin-4-yl-methanone | D | RT: 3.03 min; Mass found[M]+: 428; Yield: 11.3 |
| 23 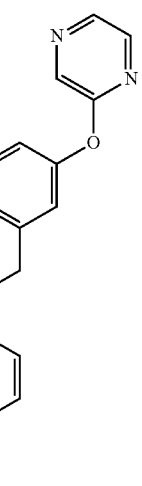 | Morpholin-4-yl-(5-{4-[3-(pyrazin-2-yloxy)-benzylamino]-pyrimidin-2-yl}-pyridin-3-yl)-methanone | D | RT: 2.55 min; Mass found[M]+: 470.3; Yield: 14.1 |
| 24 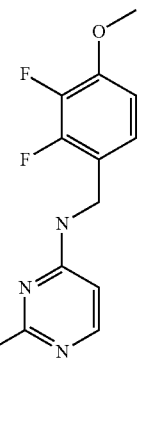 | (2,3-Difluoro-4-methoxy-benzyl)-[2-(5-trifluoromethyl-pyridin-3-yl)-pyrimidin-4-yl]-amine | C | RT: 3.87 min; Mass found[M]+: 397; Yield: 12.1 |

TABLE 1-continued

| | Structure | Chemical Name | FAK IC50 | HPLC Retention time [min] LCMS Mass found Yield [%] |
|---|---|---|---|---|
| 25 | 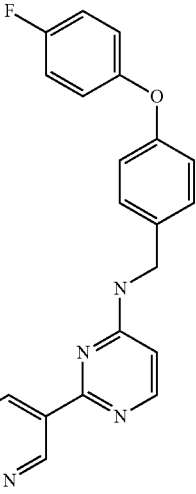 | [4-(4-Fluoro-phenoxy)-benzyl]-[2-(5-trifluoromethyl-pyridin-3-yl)-pyrimidin-4-yl]-amine | D | RT: 4.62 min; Mass found[M]+: 441.3; Yield: 42.6 |
| 26 | 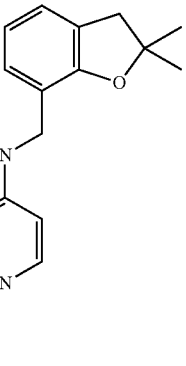 | (2,2-Dimethyl-2,3-dihydro-benzofuran-7-ylmethyl)-[2-(5-trifluoromethyl-pyridin-3-yl)-pyrimidin-4-yl]-amine | D | RT: 4.33 min; Mass found[M]+: 401.2; Yield: 15 |
| 27 | 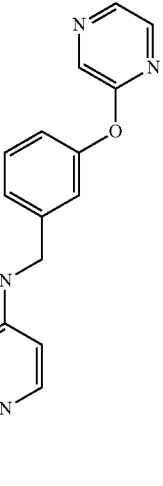 | [3-(Pyrazin-2-yloxy)-benzyl]-[2-(5-trifluoromethyl-pyridin-3-yl)-pyrimidin-4-yl]-amine | D | RT: 3.45 min; Mass found[M]+: 425.3; Yield: 7.9 |

| Structure | Chemical Name | FAK IC50 | HPLC Retention time [min] LCMS Mass found Yield [%] |
|---|---|---|---|
| 28 | (4-Morpholin-4-yl-benzyl)-[2-(5-trifluoromethyl-pyridin-3-yl)-pyrimidin-4-yl]-amine | D | RT: 2.91 min; Mass found[M]+: 416; Yield: 50.3 |
| 29 | (3-Pyrazol-1-yl-benzyl)-[2-(5-trifluoromethyl-pyridin-3-yl)-pyrimidin-4-yl]-amine | C | RT: 3.61 min; Mass found[M]+: 397; Yield: 31.4 |
| 30 | (2,3-Dihydro-benzo[1,4]dioxin-6-ylmethyl)-[2-(5-trifluoromethyl-pyridin-3-yl)-pyrimidin-4-yl]-amine | D | RT: 3.61 min; Mass found[M]+: 389; Yield: 12.8 |

TABLE 1-continued
| Structure | Chemical Name | FAK IC50 | HPLC Retention time [min] LCMS Mass found Yield [%] |
|---|---|---|---|
| 31 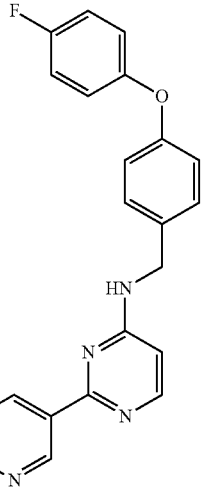 | [2-(5-Chloro-pyridin-3-yl)-pyrimidin-4-yl]-[4-(4-fluoro-phenoxy)-benzyl]-amine | D | RT: 4.33 min; Mass found[M]+: 407; Yield: 5.8 |
| 32 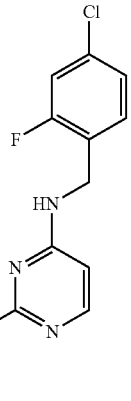 | (4-Chloro-2-fluoro-benzyl)-[2-(5-chloro-pyridin-3-yl)-pyrimidin-4-yl]-amine | A | RT: 3.76 min; Mass found[M]+: 349; Yield: 4 |
| 33 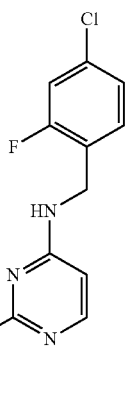 | (4-Chloro-2-fluoro-benzyl)-[2-(5-fluoro-pyridin-3-yl)-pyrimidin-4-yl]-amine | A | RT: 3.49 min; Mass found[M]+: 333; Yield: 44.6 |

TABLE 1-continued

| | Structure | Chemical Name | FAK IC50 | HPLC Retention time [min] LCMS Mass found Yield [%] |
|---|---|---|---|---|
| 34 | 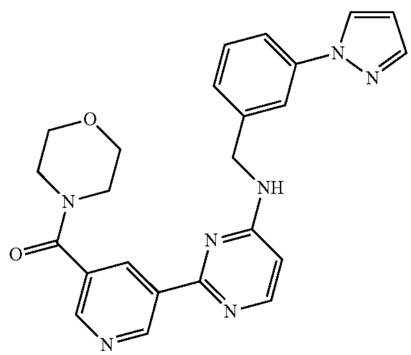 [SMILES: O=C(c1cncc(-c2nccc(NCc3cccc(-n4cccn4)c3)n2)c1)N1CCOCC1] | Morpholin-4-yl-{5-[4-(3-pyrazol-1-yl-benzylamino)-pyrimidin-2-yl]-pyridin-3-yl}-methanone | D | RT: 2.6 min; Mass found[M]+: 442.3; Yield: 14.8 |
| 35 | 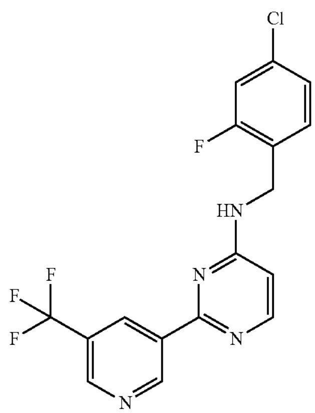 [SMILES: Fc1cc(Cl)ccc1CNc1ccnc(-c2cncc(C(F)(F)F)c2)n1] | (4-Chloro-2-fluoro-benzyl)-[2-(5-trifluoromethyl-pyridin-3-yl)-pyrimidin-4-yl]-amine | A | RT: 4.1 min; Mass found[M]+: 383; Yield: 18.2 |
| 36 | 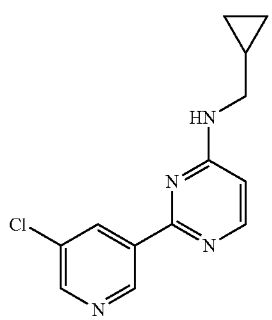 [SMILES: Clc1cncc(-c2nccc(NCC3CC3)n2)c1] | [2-(5-Chloro-pyridin-3-yl)-pyrimidin-4-yl]-cyclopropylmethyl-amine | C | RT: 2.9 min; Mass found[M]+: 261; Yield: 12.2 |
| 37 | 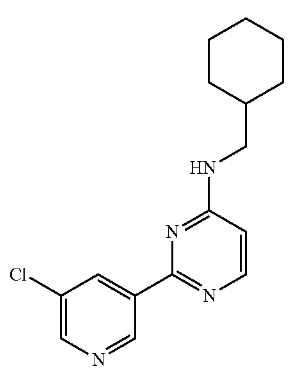 [SMILES: Clc1cncc(-c2nccc(NCC3CCCCC3)n2)c1] | [2-(5-Chloro-pyridin-3-yl)-pyrimidin-4-yl]-cyclohexylmethyl-amine | C | RT: 3.89 min; Mass found[M]+: 303; Yield: 17.3 |

TABLE 1-continued

| Structure | Chemical Name | FAK IC50 | HPLC Retention time [min] LCMS Mass found Yield [%] |
|---|---|---|---|
| 38 | [2-(5-Chloro-pyridin-3-yl)-pyrimidin-4-yl]-(2-fluoro-benzyl)-amine | A | RT: 3.32 min; Mass found[M]+: 315; Yield: 20.2 |
| 39 | [2-(5-Chloro-pyridin-3-yl)-pyrimidin-4-yl]-(4-fluoro-benzyl)-amine | B | RT: 3.4 min; Mass found[M]+: 315; Yield: 11.1 |
| 40 | (5-{4-[(2,2-Dimethyl-2,3-dihydro-benzofuran-7-ylmethyl)-amino]-pyrimidin-2-yl}-pyridin-3-yl)-morpholin-4-yl-methanone | D | RT: 3.2 min; Mass found[M]+: 446.3; Yield: 7.8 |

TABLE 2

| | Structure | Chemical Name | FAK IC50 | HT-29 IC50 | Purity % retention time Mass found yield % |
|---|---|---|---|---|---|
| 41 | 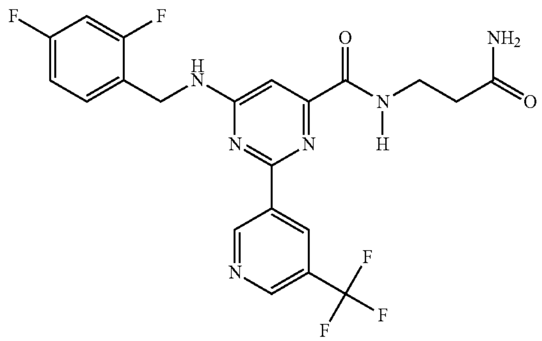 [SMILES: NC(=O)CCNC(=O)c1cc(NCc2ccc(F)cc2F)nc(-c2cncc(C(F)(F)F)c2)n1] | 6-(2,4-Difluoro-benzylamino)-2-(5-trifluoromethyl-pyridin-3-yl)-pyrimidine-4-carboxylic acid (2-carbamoyl-ethyl)-amide | A | B | 94.99%, RT: 4.38 min; Mass found[M]+: 481; Yield: 33.9 |
| 42 | 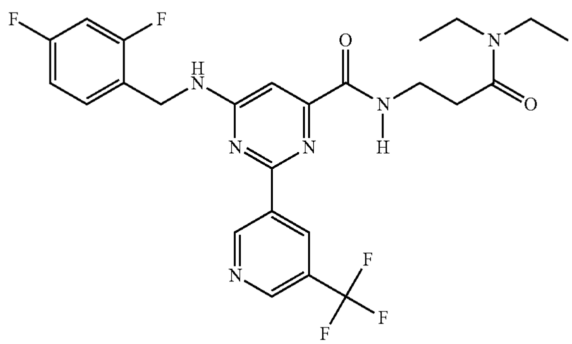 [SMILES: CCN(CC)C(=O)CCNC(=O)c1cc(NCc2ccc(F)cc2F)nc(-c2cncc(C(F)(F)F)c2)n1] | 6-(2,4-Difluoro-benzylamino)-2-(5-trifluoromethyl-pyridin-3-yl)-pyrimidine-4-carboxylic acid (2-diethylcarbamoyl-ethyl)-amide | A | C | 98.59%,; RT: 5.15 min; Mass found[M]+: 537.3; Yield: 45 |
| 43 | 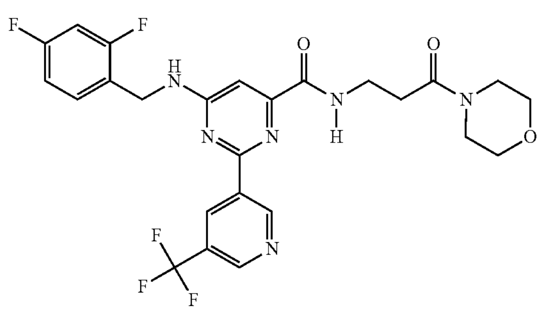 [SMILES: O=C(NCCC(=O)N1CCOCC1)c1cc(NCc2ccc(F)cc2F)nc(-c2cncc(C(F)(F)F)c2)n1] | 6-(2,4-Difluoro-benzylamino)-2-(5-trifluoromethyl-pyridin-3-yl)-pyrimidine-4-carboxylic acid (3-morpholin-4-yl-3-oxo-propyl)-amide | A | C | 97.44%,; RT: 4.66 min; Mass found[M]+: 551.2; Yield: 31.5 |
| 44 | 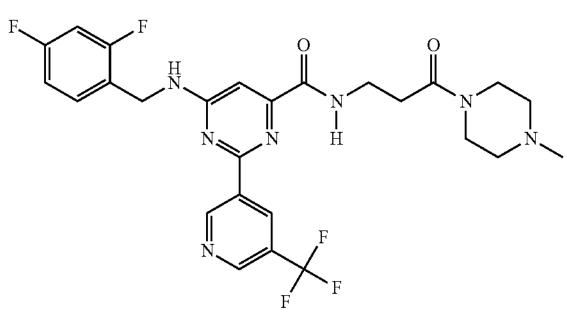 [SMILES: CN1CCN(C(=O)CCNC(=O)c2cc(NCc3ccc(F)cc3F)nc(-c3cncc(C(F)(F)F)c3)n2)CC1] | 6-(2,4-Difluoro-benzylamino)-2-(5-trifluoromethyl-pyridin-3-yl)-pyrimidine-4-carboxylic acid [3-(4-methyl-piperazin-1-yl)-3-oxo-propyl]-amide | A | C | 97.81%,; RT: 4.11 min; Mass found[M]+: 564; Yield: 28.7 |

TABLE 2-continued

| Structure | Chemical Name | FAK IC50 | HT-29 IC50 | Purity % retention time Mass found yield % |
|---|---|---|---|---|
| 45 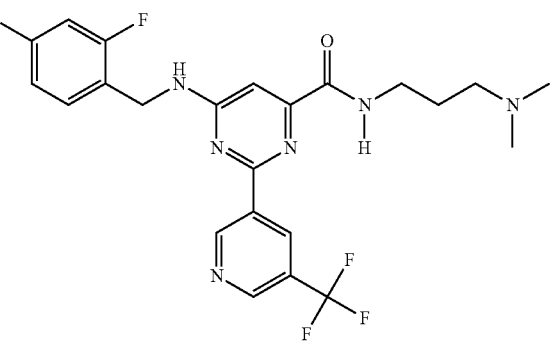 | 6-(2,4-Difluoro-benzylamino)-2-(5-trifluoromethyl-pyridin-3-yl)-pyrimidine-4-carboxylic acid (3-dimethylamino-propyl)-amide | A | C | 99.85%,; RT: 4.23 min; Mass found[M]+: 495.3; Yield: 22.8 |
| 46 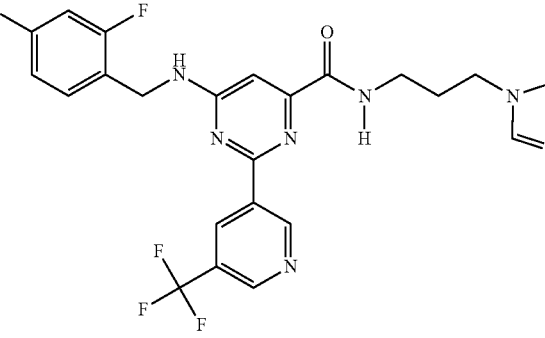 | 6-(2,4-Difluoro-benzylamino)-2-(5-trifluoromethyl-pyridin-3-yl)-pyrimidine-4-carboxylic acid (3-imidazol-1-yl-propyl)-amide | A | C | 98.82%,; RT: 4.28 min; Mass found[M]+: 518.3; Yield: 58 |
| 47 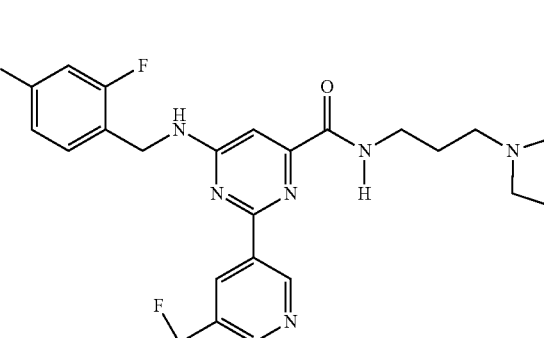 | 6-(2,4-Difluoro-benzylamino)-2-(5-trifluoromethyl-pyridin-3-yl)-pyrimidine-4-carboxylic acid [3-(2-oxo-pyrrolidin-1-yl)-propyl]-amide | A | B | 99.05%,; RT: 4.78 min; Mass found[M]+: 535.3; Yield: 67.6 |
| 48 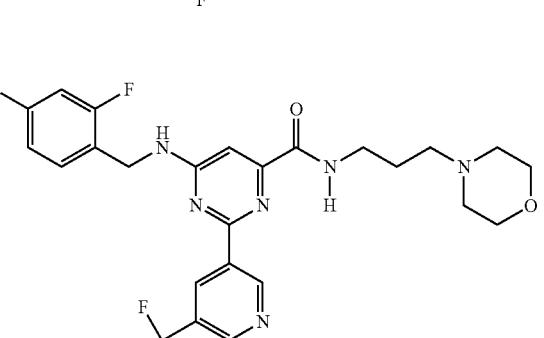 | 6-(2,4-Difluoro-benzylamino)-2-(5-trifluoromethyl-pyridin-3-yl)-pyrimidine-4-carboxylic acid (3-morpholin-4-yl-propyl)-amide | A | D | 98.11%,; RT: 4.25 min; Mass found[M]+: 537.3; Yield: 54.1 |

TABLE 2-continued

| | Structure | Chemical Name | FAK IC50 | HT-29 IC50 | Purity % retention time Mass found yield % |
|---|---|---|---|---|---|
| 49 | 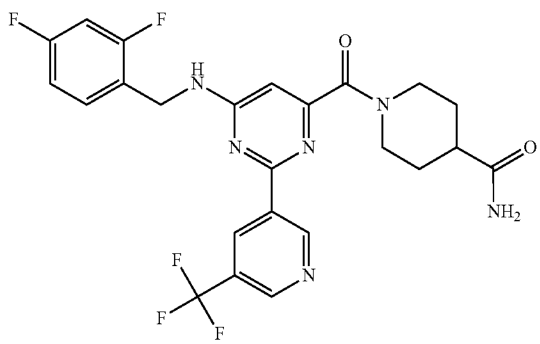 [SMILES: NC(=O)C1CCN(C(=O)c2cc(NCc3ccc(F)cc3F)nc(-c3cncc(C(F)(F)F)c3)n2)CC1] | 1-[6-(2,4-Difluoro-benzylamino)-2-(5-trifluoromethyl-pyridin-3-yl)-pyrimidine-4-carbonyl]-piperidine-4-carboxylic acid amide | A | C | 99.13%,; RT: 4.18 min; Mass found[M]+: 521.3; Yield: 42.6 |
| 50 | 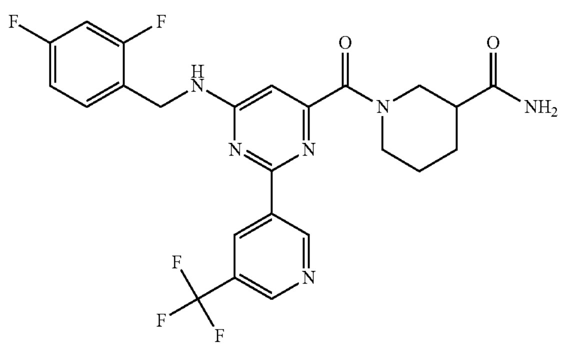 [SMILES: NC(=O)C1CCCN(C(=O)c2cc(NCc3ccc(F)cc3F)nc(-c3cncc(C(F)(F)F)c3)n2)C1] | 1-[6-(2,4-Difluoro-benzylamino)-2-(5-trifluoromethyl-pyridin-3-yl)-pyrimidine-4-carbonyl]-piperidine-3-carboxylic acid amide | A | C | 99.54%,; RT: 4.32 min; Mass found[M]+: 521.3; Yield: 48.3 |
| 51 | 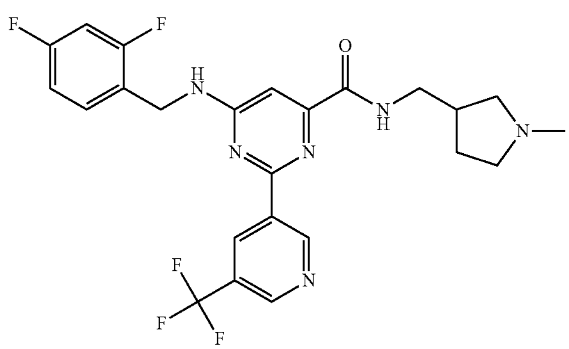 [SMILES: CN1CCC(CNC(=O)c2cc(NCc3ccc(F)cc3F)nc(-c3cncc(C(F)(F)F)c3)n2)C1] | 6-(2,4-Difluoro-benzylamino)-2-(5-trifluoromethyl-pyridin-3-yl)-pyrimidine-4-carboxylic acid (1-methyl-pyrrolidin-3-ylmethyl)-amide | A | C | 97.51%,; RT: 4.25 min; Mass found[M]+: 507.3; Yield: 40.2 |
| 52 | 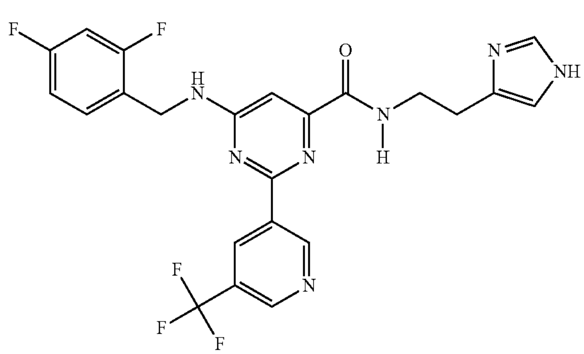 [SMILES: O=C(NCCc1c[nH]cn1)c1cc(NCc2ccc(F)cc2F)nc(-c2cncc(C(F)(F)F)c2)n1] | 6-(2,4-Difluoro-benzylamino)-2-(5-trifluoromethyl-pyridin-3-yl)-pyrimidine-4-carboxylic acid [2-(1H-imidazol-4-yl)-ethyl]-amide | A | C | 99.59%,; RT: 4.22 min; Mass found[M]+: 504; Yield: 61.3 |

TABLE 2-continued

| | Structure | Chemical Name | FAK IC50 | HT-29 IC50 | Purity % retention time Mass found yield % |
|---|---|---|---|---|---|
| 53 | 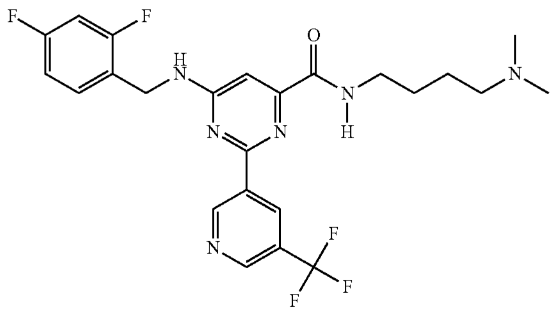 [SMILES: CN(C)CCCCNC(=O)c1cc(NCc2ccc(F)cc2F)nc(-c2cncc(C(F)(F)F)c2)n1] | 6-(2,4-Difluoro-benzylamino)-2-(5-trifluoromethyl-pyridin-3-yl)-pyrimidine-4-carboxylic acid (4-dimethylamino-butyl)-amide | A | C | 98.38%,; RT: 4.29 min; Mass found[M]+: 509.2; Yield: 59.5 |
| 54 | 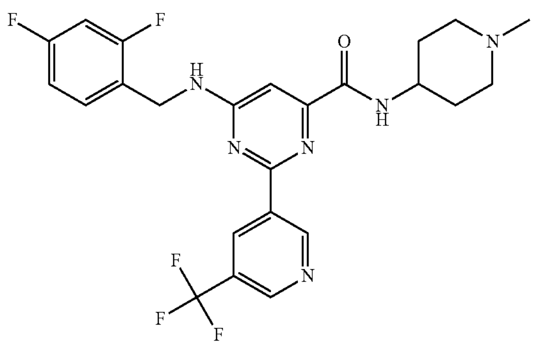 [SMILES: CN1CCC(NC(=O)c2cc(NCc3ccc(F)cc3F)nc(-c3cncc(C(F)(F)F)c3)n2)CC1] | 6-(2,4-Difluoro-benzylamino)-2-(5-trifluoromethyl-pyridin-3-yl)-pyrimidine-4-carboxylic acid (1-methyl-piperidin-4-yl)-amide | A | C | 97.67%, RT: 4.2 min; Mass found[M]+: 507; Yield: 14.1 |
| 55 | 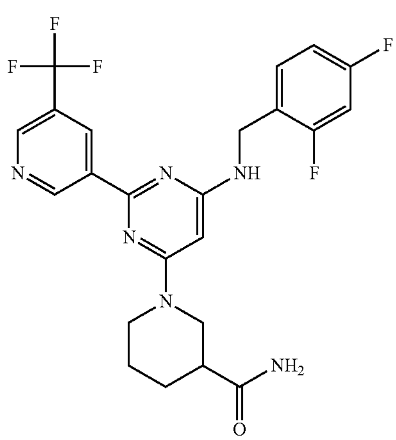 [SMILES: NC(=O)C1CCCN(c2cc(NCc3ccc(F)cc3F)nc(-c3cncc(C(F)(F)F)c3)n2)C1] | 1-[6-(2,4-Difluoro-benzylamino)-2-(5-trifluoromethyl-pyridin-3-yl)-pyrimidin-4-yl]-piperidine-3-carboxylic acid amide | B | C | 96.66%,; RT: 4.03 min; Mass found[M]+: 493; Yield: 20.8 |
| 56 | 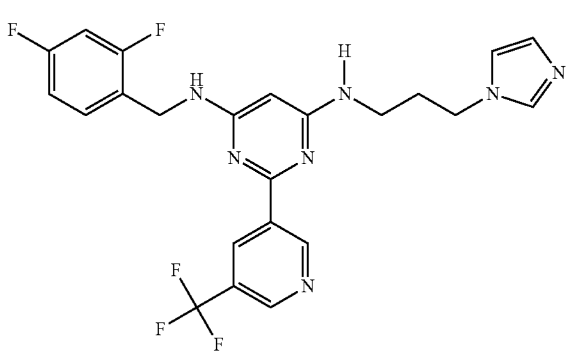 [SMILES: Fc1ccc(CNc2cc(NCCCn3ccnc3)nc(-c3cncc(C(F)(F)F)c3)n2)c(F)c1] | N-(2,4-Difluoro-benzyl)-N'-(3-imidazol-1-yl-propyl)-2-(5-trifluoromethyl-pyridin-3-yl)-pyrimidine-4,6-diamine | B | C | 99.66%,; RT: 3.66 min; Mass found[M]+: 490.3; Yield: 36.7 |

TABLE 2-continued

| | Structure | Chemical Name | FAK IC50 | HT-29 IC50 | Purity % retention time Mass found yield % |
|---|---|---|---|---|---|
| 57 | 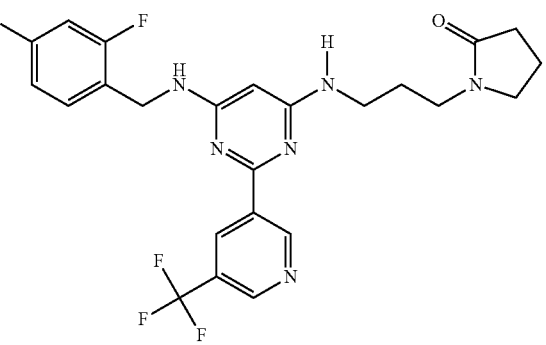 | 1-{3-[6-(2,4-Difluoro-benzylamino)-2-(5-trifluoromethyl-pyridin-3-yl)-pyrimidin-4-ylamino]-propyl}-pyrrolidin-2-one | B | C | 99.76%,; RT: 4.02 min; Mass found[M]+: 507.3; Yield: 27.5 |
| 58 | 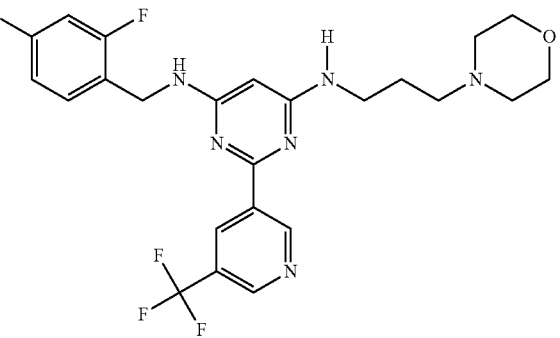 | N-(2,4-Difluoro-benzyl)-N'-(3-morpholin-4-yl-propyl)-2-(5-trifluoromethyl-pyridin-3-yl)-pyrimidine-4,6-diamine | A | C | 99.02%,; RT: 3.66 min; Mass found[M]+: 509.3; Yield: 22.3 |
| 59 | 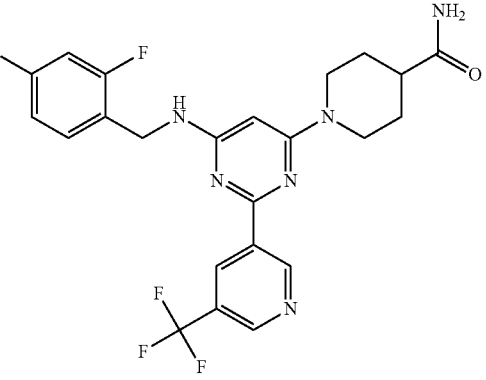 | 1-[6-(2,4-Difluoro-benzylamino)-2-(5-trifluoromethyl-pyridin-3-yl)-pyrimidin-4-yl]-piperidine-4-carboxylic acid amide | B | C | 99.67%,; RT: 3.88 min; Mass found[M]+: 493; Yield: 10.7 |
| 60 | 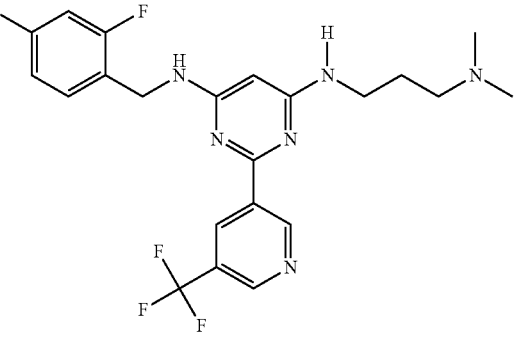 | N-(2,4-Difluoro-benzyl)-N'-(3-dimethylamino-propyl)-2-(5-trifluoromethyl-pyridin-3-yl)-pyrimidine-4,6-diamine | A | C | 97.67%,; RT: 3.63 min; Mass found[M]+: 467.3; Yield: 11.9 |

TABLE 2-continued

| Structure | Chemical Name | FAK IC50 | HT-29 IC50 | Purity % retention time Mass found yield % |
|---|---|---|---|---|
| 61 | 3-[6-(2,4-Difluoro-benzylamino)-2-(5-trifluoromethyl-pyridin-3-yl)-pyrimidin-4-ylamino]-propionamide | B | | 99.38%,; RT: 3.81 min; Mass found[M]+: 453; Yield: 6.2 |
| 62 | 3-[6-(2,4-Difluoro-benzylamino)-2-(5-trifluoromethyl-pyridin-3-yl)-pyrimidin-4-ylamino]-N,N-diethyl-propionamide | B | C | 98.63%,; RT: 4.6 min; Mass found[M]+: 509.3; Yield: 27.5 |
| 63 | 3-[6-(2,4-Difluoro-benzylamino)-2-(5-trifluoromethyl-pyridin-3-yl)-pyrimidin-4-ylamino]-1-morpholin-4-yl-propan-1-one | B | C | 99.59%,; RT: 3.99 min; Mass found[M]+: 523.3; Yield: 40.4 |
| 64 | 3-[6-(2,4-Difluoro-benzylamino)-2-(5-trifluoromethyl-pyridin-3-yl)-pyrimidin-4-ylamino]-1-(4-methyl-piperazin-1-yl)-propan-1-one | B | C | 99.74%,; RT: 3.52 min; Mass found[M]+: 536.3; Yield: 10.4 |

TABLE 2-continued

| | Structure | Chemical Name | FAK IC50 | HT-29 IC50 | Purity % retention time Mass found yield % |
|---|---|---|---|---|---|
| 65 | 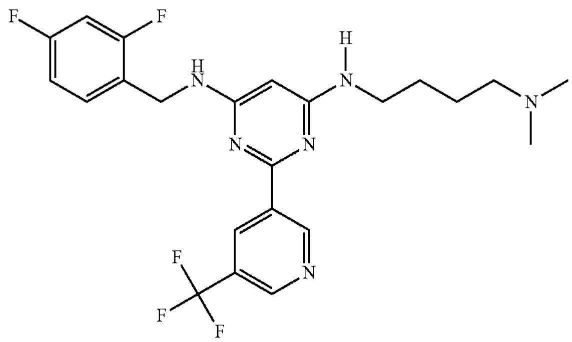 [SMILES: CN(C)CCCCNc1cc(NCc2ccc(F)cc2F)nc(-c2cncc(C(F)(F)F)c2)n1] | N-(2,4-Difluoro-benzyl)-N'-(4-dimethylamino-butyl)-2-(5-trifluoromethyl-pyridin-3-yl)-pyrimidine-4,6-diamine | B | D | 96.81%,; RT: 3.63 min; Mass found[M]+: 481.2; Yield: 20.5 |
| 66 | 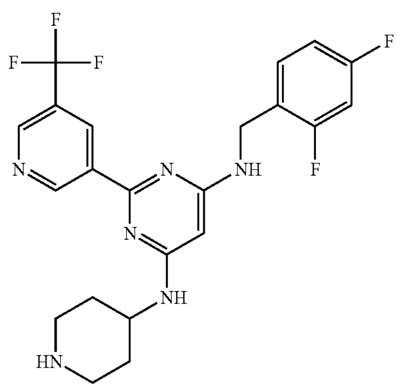 [SMILES: Fc1ccc(CNc2cc(NC3CCNCC3)nc(-c3cncc(C(F)(F)F)c3)n2)c(F)c1] | N-(2,4-Difluoro-benzyl)-N'-piperidin-4-yl-2-(5-trifluoromethyl-pyridin-3-yl)-pyrimidine-4,6-diamine | B | | 96.44%,; RT: 3.78 min; Mass found[M]+: 465; Yield: 4.4 |
| 67 | 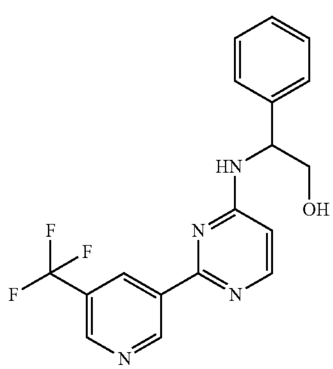 | 2-Phenyl-2-[2-(5-trifluoromethyl-pyridin-3-yl)-pyrimidin-4-ylamino]-ethanol | B | | 98.85%,; RT: 3.24 min; Mass found[M]+: 361; Yield: 23 |
| 68 | 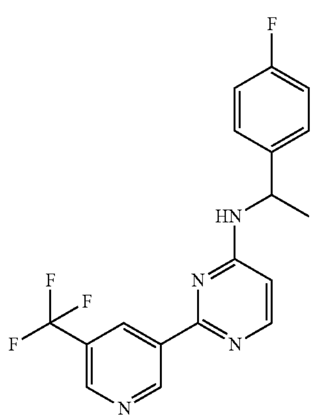 [SMILES: CC(Nc1ccnc(-c2cncc(C(F)(F)F)c2)n1)c1ccc(F)cc1] | [1-(4-Fluoro-phenyl)-ethyl]-[2-(5-trifluoromethyl-pyridin-3-yl)-pyrimidin-4-yl]-amine | B | | 95.58%,; RT: 3.94 min; Mass found[M]+: 363; Yield: 16.2 |

TABLE 2-continued

| | Structure | Chemical Name | FAK IC50 | HT-29 IC50 | Purity % retention time Mass found yield % |
|---|---|---|---|---|---|
| 69 | 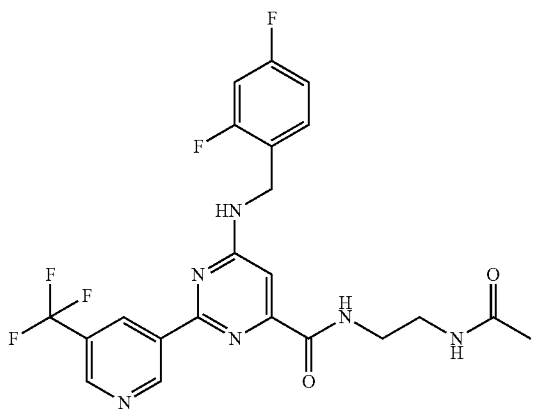 [SMILES: CC(=O)NCCNC(=O)c1cc(NCc2ccc(F)cc2F)nc(-c2cncc(C(F)(F)F)c2)n1] | 6-(2,4-Difluoro-benzylamino)-2-(5-trifluoromethyl-pyridin-3-yl)-pyrimidine-4-carboxylic acid (2-acetylamino-ethyl)-amide | A | | 98.85%,; RT: 4.48 min; Mass found[M]+: 495; Yield: 28.5 |
| 70 | 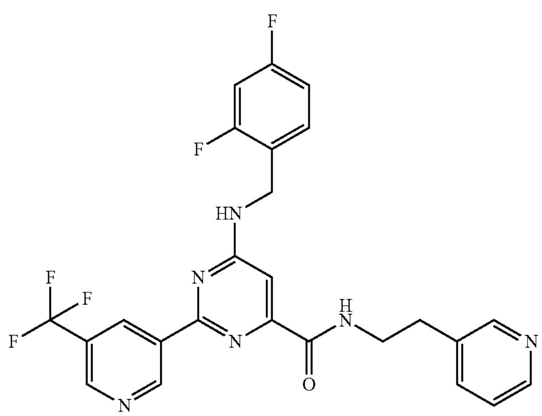 [SMILES: O=C(NCCc1cccnc1)c1cc(NCc2ccc(F)cc2F)nc(-c2cncc(C(F)(F)F)c2)n1] | 6-(2,4-Difluoro-benzylamino)-2-(5-trifluoromethyl-pyridin-3-yl)-pyrimidine-4-carboxylic acid (2-pyridin-3-yl-ethyl)-amide | A | | 99.58%,; RT: 4.32 min; Mass found[M]+: 515; Yield: 49.4 |
| 71 | 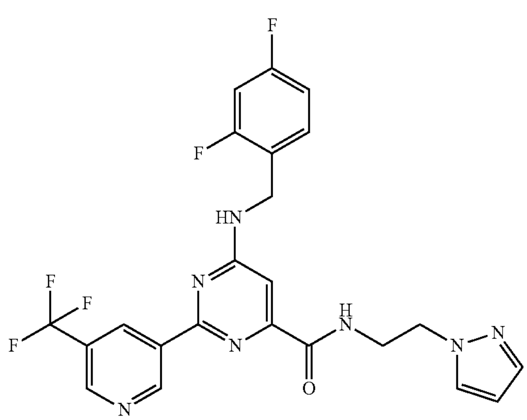 [SMILES: O=C(NCCn1cccn1)c1cc(NCc2ccc(F)cc2F)nc(-c2cncc(C(F)(F)F)c2)n1] | 6-(2,4-Difluoro-benzylamino)-2-(5-trifluoromethyl-pyridin-3-yl)-pyrimidine-4-carboxylic acid (2-pyrazol-1-yl-ethyl)-amide | A | | 95.57%,; RT: 5.06 min; Mass found[M]+: 504; Yield: 7 |

TABLE 2-continued

| Structure | Chemical Name | FAK IC50 | HT-29 IC50 | Purity % retention time Mass found yield % |
|---|---|---|---|---|
| 72 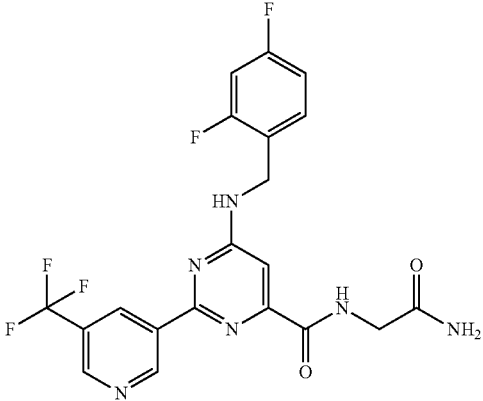 | 6-(2,4-Difluoro-benzylamino)-2-(5-trifluoromethyl-pyridin-3-yl)-pyrimidine-4-carboxylic acid carbamoylmethyl-amide | A | B | 98.19%,; RT: 4.438 min; Mass found[M]+: 467; Yield: 37 |
| 73 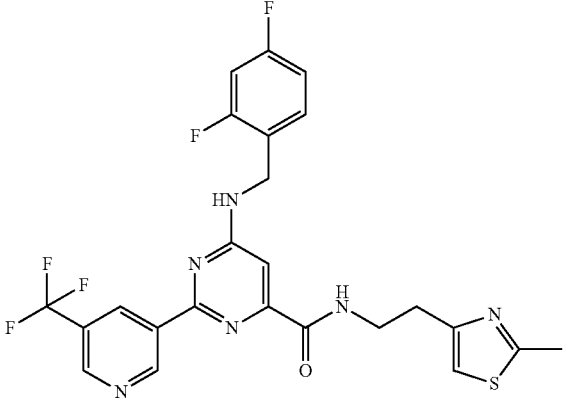 [SMILES: Cc1nc(CCNC(=O)c2cc(NCc3ccc(F)cc3F)nc(-c3cncc(C(F)(F)F)c3)n2)cs1] | 6-(2,4-Difluoro-benzylamino)-2-(5-trifluoromethyl-pyridin-3-yl)-pyrimidine-4-carboxylic acid [2-(2-methyl-thiazol-4-yl)-ethyl]-amide | B |  | 99.15%,; RT: 4.62 min; Mass found[M]+: 535; Yield: 12 |
| 74 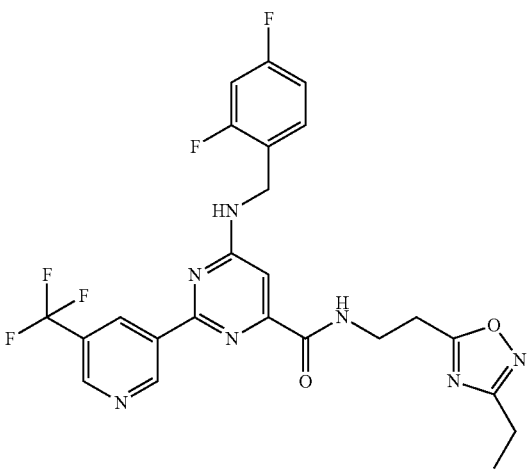 [SMILES: CCc1noc(CCNC(=O)c2cc(NCc3ccc(F)cc3F)nc(-c3cncc(C(F)(F)F)c3)n2)n1] | 6-(2,4-Difluoro-benzylamino)-2-(5-trifluoromethyl-pyridin-3-yl)-pyrimidine-4-carboxylic acid [2-(3-ethyl-[1,2,4]oxadiazol-5-yl)-ethyl]-amide | B |  | 97.72%,; RT: 5.422 min; Mass found[M]+: 534; Yield: 16 |

TABLE 2-continued

| Structure | Chemical Name | FAK IC50 | HT-29 IC50 | Purity % retention time Mass found yield % |
|---|---|---|---|---|
| 75 | 6-(2,4-Difluoro-benzylamino)-2-(5-trifluoromethyl-pyridin-3-yl)-pyrimidine-4-carboxylic acid [2-(2-oxo-imidazolidin-1-yl)-ethyl]-amide | | B | 93.44%,; RT: 4.471 min; Mass found[M]+: 522; Yield: 5 |
| 76 Chiral | 6-(2,4-Difluoro-benzylamino)-2-(5-trifluoromethyl-pyridin-3-yl)-pyrimidine-4-carboxylic acid ((R)-2-methyl-1-methylcarbamoyl-propyl)-amide | | B | 97.04%,; RT: 5.094 min; Mass found[M]+: 523; Yield: 8 |

TABLE 3

| Structure | Chemical Name | FAK IC$_{50}$ | HT-29 IC$_{50}$ | Purity retention time mass found |
|---|---|---|---|---|
| 77 | 2-(2-Aminopyridin-3-yl)-N-[2-(trifluoromethyl)benzyl]pyrimidin-4-amine | B | D | 99%, RT: 3.41 min 346 [M + H]+. $^1$H NMR (400 MHz, DMSO-D$_6$) δ 8.85 (d, J = 7.2, 1H), 8.75 (s, 1H), 8.26 (d, J = 6.1, 1H), 8.17 (d, J = 5.4, 1H), 7.78 (d, J = 7.7, 1H), 7.66 (t, J = 7.2, 1H), 7.59 (d, J = 7.6, 1H), 7.51 (t, J = 7.4, 1H), 7.00 (t, J = 6.8, 1H), 6.76 (d, J = 5.9, 1H), 4.83 (d, J = 4.3, 2H) |

TABLE 3-continued

| Structure | Chemical Name | FAK IC$_{50}$ | HT-29 IC$_{50}$ | Purity retention time mass found |
|---|---|---|---|---|
| 78 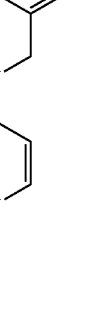 | 2-(2-Aminopyridin-3-yl)-N-(2-fluorobenzyl)pyrimidin-4-amine | B | | 99%, RT: 2.71 min 296 [M + H]+ $^1$H NMR (400 MHz, DMSO-D$_6$) δ 8.99 (d, J = 7.3, 1H), 8.73 (s, 1H), 8.21 (t, J = 6.5, 2H), 7.45 (td, J = 7.7, 1.7, 1H), 7.35 (dd, J = 13.4, 6.6, 1H), 7.28-7.12 (m, 2H), 7.06 (dd, J = 7.7, 6.1, 1H), 6.69 (d, J = 6.2, 1H), 4.70 (d, J = 4.6, 2H) |
| 79 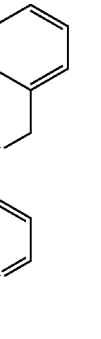 | 2-(2-Aminopyridin-3-yl)-N-(3-fluorobenzyl)pyrimidin-4-amine | D | | 99%, RT: 2.76 min 296 [M + H]+. $^1$H NMR (400 MHz, DMSO-D$_6$) δ 9.41 (s, 1H), 8.91 (d, J = 7.4, 1H), 8.24 (d, J = 6.2, 2H), 7.48-7.34 (m, 1H), 7.23 (d, J = 6.0, 2H), 7.18-7.00 (m, 2H), 6.81 (d, J = 6.2, 1H), 4.69 (d, J = 4.5, 2H) |
| 80 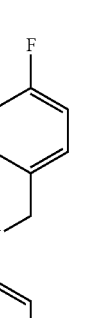 | 2-(2-Aminopyridin-3-yl)-N-(4-fluorobenzyl)pyrimidin-4-amine | C | | 99%, RT: 2.74 min 296 [M + H]+. 1H NMR (400 MHz, DMSO-D$_6$) δ 9.10 (s, 1H), 8.94 (d, J = 7.4, 1H), 8.22 (d, J = 6.0, 2H), 7.43 (dd, J = 7.6, 5.9, 2H), 7.18 (t, J = 8.7, 2H), 7.05 (t, J = 6.8, 1H), 6.74 (d, J = 6.4, 1H), 4.64 (d, J = 4.3, 2H) |
| 81 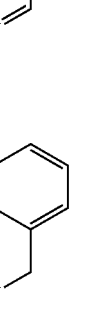 | 2-(2-Aminopyridin-3-yl)-N-benzylpyrimidin-4-amine | C | | 98%, RT: 2.53 min 278 [M + H]+. 1H NMR (400 MHz, DMSO-D$_6$) δ 9.08 (s, 1H), 8.95 (d, J = 7.4, 1H), 8.22 (d, J = 6.1, 2H), 7.46-7.21 (m, 5H), 7.05 (t, J = 6.8, 1H), 6.73 (d, J = 6.3, 1H), 4.66 (d, J = 4.7, 2H) |

TABLE 3-continued

| Structure | Chemical Name | FAK IC$_{50}$ | HT-29 IC$_{50}$ | Purity retention time mass found |
|---|---|---|---|---|
| 82 | 2-(2-Aminopyridin-3-yl)-N-(2-methylbenzyl)pyrimidin-4-amine | C | | 99%, RT: 2.80 min 292 [M + H]+. 1H NMR (400 MHz, DMSO-D$_6$) δ 8.97 (s, 1H), 8.22 (d, J = 6.1, 2H), 7.30 (d, J = 6.9, 1H), 7.26-7.12 (m, 3H), 7.05 (t, J = 6.8, 1H), 6.72 (d, J = 4.4, 1H), 4.63 (d, J = 4.7, 2H), 2.34 (s, 3H) |
| 83 | 2-(2-Aminopyridin-3-yl)-N-(2-methoxybenzyl)pyrimidin-4-amine | C | | 99%, RT: 2.69 min 308 [M + H]+. 1H NMR (400 MHz, DMSO-D$_6$) δ 9.12 (d, J = 7.1, 1H), 8.93 (d, J = 7.4, 1H), 8.24 (d, J = 5.7, 1H), 8.20 (d, J = 6.4, 1H), 7.28 (t, J = 6.6, 2H), 7.07 (d, J = 6.5, 1H), 7.04 (d, J = 8.0, 1H), 6.91 (t, J = 7.3, 1H), 6.76 (d, J = 6.3, 1H), 4.61 (d, J = 4.9, 2H), 3.84 (s, 3H) |
| 84 | 2-(2-Aminopyridin-3-yl)-N-[2-(trifluoromethoxy)benzyl]pyrimidin-4-amine | C | | 99.5%, RT: 3.53 min 362 [M + H]+. 1H NMR (400 MHz, DMSO-D$_6$) δ 8.92 (d, J = 7.5, 1H), 8.67 (s, 1H), 8.23 (d, J = 5.9, 1H), 8.18 (d, J = 5.0, 1H), 7.51 (d, J = 7.3, 1H), 7.48-7.31 (m, 3H), 7.02 (t, J = 6.8, 1H), 6.69 (d, J = 5.4, 1H), 4.73 (d, J = 5.1, 2H) |
| 85 | 2-(2-Aminopyridin-3-yl)-N-(2,3-difluorobenzyl)pyrimidin-4-amine | C | | 99%, RT: 2.70 min 314 [M + H]+. 1H NMR (400 MHz, DMSO-D$_6$) δ 9.09 (s, 1H), 8.95 (d, J = 7.0, 1H), 8.44-8.10 (m, 2H), 7.45-7.30 (m, 1H), 7.27 (t, J = 6.9, 1H), 7.23-7.13 (m, 1H), 7.05 (t, J = 6.9, 1H), 6.74 (s, 1H), 4.74 (d, J = 4.3, 2H) |

TABLE 3-continued

| Structure | Chemical Name | FAK IC$_{50}$ | HT-29 IC$_{50}$ | Purity retention time mass found |
|---|---|---|---|---|
| 86 | 2-(2-Aminopyridin-3-yl)-N-(2-chlorobenzyl)pyrimidin-4-amine | B | | 99%, RT: 3.04 min 312 [M + H]+ (35Cl) 1H NMR (400 MHz, DMSO-D$_6$) δ 9.08 (s, 1H), 8.93 (d, J = 7.2, 1H), 8.24 (d, J = 6.2, 1H), 8.20 (d, J = 5.9, 1H), 7.54-7.42 (m, 2H), 7.42-7.25 (m, 2H), 7.04 (t, J = 6.9, 1H), 6.75 (d, J = 6.0, 1H), 4.73 (d, J = 5.1, 2H) |
| 87 | 2-(2-Aminopyridin-3-yl)-N-[2-(methylsulfonyl)benzyl]pyrimidin-4-amine | C | | 99%, RT: 2.37 min 356 [M + H]+. 1H NMR (400 MHz, DMSO-D$_6$) δ 8.92 (d, J = 7.6, 1H), 8.61 (s, 1H), 8.26 (d, J = 6.1, 1H), 8.16 (d, J = 6.0, 1H), 7.99 (d, J = 7.8, 1H), 7.70 (t, J = 7.5, 1H), 7.60 (d, J = 7.9, 1H), 7.57 (t, J = 7.6, 1H), 6.99 (t, J = 6.9, 1H), 6.76 (d, J = 5.6, 1H), 5.12 (d, J = 4.5, 2H), 3.34 (s, 3H) |
| 88 | N-[3-({[2-(2-Aminopyridin-3-yl)pyrimidin-4-yl]amino}methyl)pyridin-2-yl]-N-methylmethane-sulfonamide | D | | 96%, RT: 2.23 min 386 [M + H]+. 1H NMR (400 MHz, DMSO-D$_6$) δ 8.91 (d, J = 7.2, 1H), 8.74 (s, 1H), 8.45 (d, J = 4.6, 1H), 8.25 (d, J = 5.8, 1H), 8.17 (d, J = 5.4, 1H), 7.84 (dd, J = 7.7, 1.5, 1H), 7.43 (dd, J = 7.4, 4.9, 1H), 6.97 (t, J = 6.9, 1H), 6.74 (d, J = 6.2, 1H), 4.81 (d, J = 5.5, 2H), 3.19 (s, 3H), 3.17 (s, 3H) |
| 89 | 2-Pyridin-3-yl-N-[2-(trifluoromethyl)benzyl]pyrimidin-4-amine | B | D | 99%, RT: 3.25 min 331 [M + H]+. 1H NMR (400 MHz, DMSO-D$_6$) δ 9.82 (s, 1H), 9.38 (d, J = 1.6, 1H), 8.91 (d, J = 5.1, 1H), 8.84 (d, J = 8.0, 1H), 8.31 (d, J = 6.8, 1H), 7.87 (dd, J = 7.9, 5.3, 1H), 7.79 (d, J = 7.8, 1H), 7.68 (t, J = 7.6, 1H), 7.65 (d, J = 7.0, 1H), 7.52 (t, J = 7.3, 1H), 6.96 (d, J = 6.8, 1H), 4.97 (d, J = 5.3, 2H) |

TABLE 3-continued

| | Structure | Chemical Name | FAK IC$_{50}$ | HT-29 IC$_{50}$ | Purity retention time mass found |
|---|---|---|---|---|---|
| 90 | 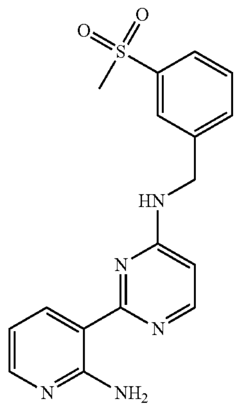 [SMILES: CS(=O)(=O)c1cccc(CNc2ccnc(-c3cccnc3N)n2)c1] | 2-(2-Aminopyridin-3-yl)-N-[3-(methylsulfonyl)benzyl]pyrimidin-4-amine | C | | 99%, RT: 2.22 min 356 [M + H]+. 1H NMR (400 MHz, DMSO-D$_6$) δ 8.50 (s, 1H), 7.96 (d, J = 5.6, 1H), 7.89 (s, 1H), 7.84 (dt, J = 7.2, 1.7, 1H), 7.67 (d, J = 7.7, 1H), 7.63 (t, J = 7.4, 1H), 6.55 (d, J = 5.8, 1H), 4.62 (d, J = 5.3, 2H), 3.21 (s, 3H) |
| 91 | 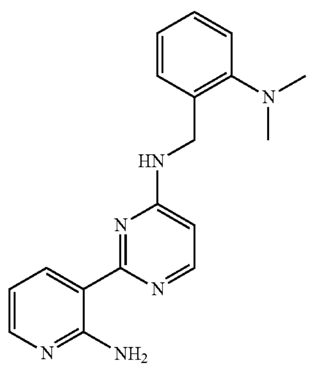 [SMILES: CN(C)c1ccccc1CNc1ccnc(-c2cccnc2N)n1] | 2-(2-Aminopyridin-3-yl)-N-[2-(dimethylamino)benzyl]pyrimidin-4-amine | C | | 97%, RT: 1.88 min 321 [M + H]+. 1H NMR (400 MHz, DMSO-D$_6$) δ 8.99 (d, J = 6.8, 1H), 8.25 (t, J = 6.4, 2H), 7.86 (s, 1H), 7.63-7.41 (m, 4H), 7.05 (t, J = 6.6, 1H), 6.82 (d, J = 6.4, 1H), 5.06 (s, 2H), 3.18 (s, 6H) |
| 92 | 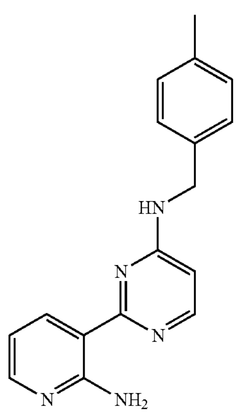 [SMILES: Cc1ccc(CNc2ccnc(-c3cccnc3N)n2)cc1] | 2-(2-Aminopyridin-3-yl)-N-(4-methylbenzyl)pyrimidin-4-amine | D | | 99.6%, RT: 2.88 min 292 [M + H]+. 1H NMR (400 MHz, DMSO-D$_6$) δ 8.97 (d, J = 7.0, 1H), 8.81 (s, 1H), 8.20 (d, J = 6.1, 2H), 7.27 (d, J = 8.0, 2H), 7.15 (d, J = 7.7, 2H), 7.05 (t, J = 6.8, 1H), 6.68 (d, J = 6.2, 1H), 4.60 (d, J = 5.0, 2H), 2.27 (s, 3H) |
| 93 | 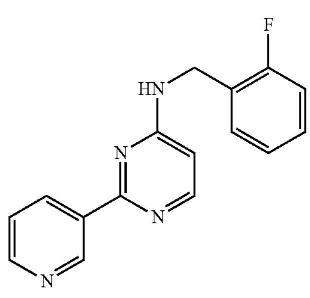 [SMILES: Fc1ccccc1CNc1ccnc(-c2cccnc2)n1] | N-(2-Fluorobenzyl)-2-pyridin-3-ylpyrimidin-4-amine | B | | 96%, RT: 2.68 min 281 [M + H]+. 1H NMR (400 MHz, DMSO-D$_6$) δ 9.79 (s, 1H), 9.49 (s, 1H), 8.94 (dd, J = 5.1, 1.3, 1H), 8.91 (d, J = 7.8, 1H), 8.27 (d, J = 6.8, 1H), 7.88 (dd, J = 7.5, 5.1, 1H), 7.51 (t, J = 7.2, 1H), 7.37 (td, J = 7.4, 1.6, 1H), 7.24 (dd, J = 9.8, 8.8, 2H), 7.19 (dd, J = 7.5, 1.1, 1H), 6.88 (dd, J = 6.8, 2.7, 1H), 4.84 (d, J = 5.5, 2H) |

TABLE 3-continued

| Structure | Chemical Name | FAK IC$_{50}$ | HT-29 IC$_{50}$ | Purity retention time mass found |
|---|---|---|---|---|
| 94 | 2-(6-Aminopyridin-3-yl)-N-[2-(trifluoromethyl)benzyl]pyrimidin-4-amine | C | | 97%, RT: 2.77 min 346 [M + H]+. 1H NMR (400 MHz, DMSO-D$_6$) δ 9.70 (s, 1H), 8.84 (d, J = 1.6, 1H), 8.51 (dd, J = 9.4, 1.8, 1H), 8.20 (d, J = 6.8, 1H), 7.79 (d, J = 7.8, 1H), 7.68 (t, J = 7.4, 1H), 7.63 (d, J = 7.5, 1H), 7.53 (t, J = 7.6, 1H), 7.02 (d, J = 9.3, 1H), 6.83 (d, J = 6.8, 1H), 4.94 (d, J = 5.0, 2H) |
| 95 | 2-(2-Aminopyridin-3-yl)-N-(3-methylbenzyl)pyrimidin-4-amine | D | | 99.2%, RT: 2.90 min 292 [M + H]+. 1H NMR (400 MHz, DMSO-D$_6$) δ 8.97 (d, J = 7.4, 1H), 8.86 (s, 1H), 8.21 (d, J = 6.2, 2H), 7.34-7.13 (m, 3H), 7.13-6.98 (m, 2H), 6.69 (d, J = 6.2, 1H), 4.61 (d, J = 5.2, 2H), 2.29 (s, 3H) |
| 96 | 2-(2-Aminopyridin-3-yl)-N-[4-(trifluoromethyl)benzyl]pyrimidin-4-amine | D | | 99.6%, RT: 3.49 min 346 [M + H]+. 1H NMR (400 MHz, DMSO-D$_6$) δ 9.05 (s, 1H), 8.93 (d, J = 7.3, 1H), 8.24 (d, J = 6.2, 1H), 8.19 (d, J = 5.6, 1H), 7.72 (d, J = 8.1, 2H), 7.61 (d, J = 8.1, 2H), 7.02 (t, J = 6.7, 1H), 6.73 (d, J = 6.1, 1H), 4.76 (d, J = 5.0, 2H) |

TABLE 3-continued

| Structure | Chemical Name | FAK IC$_{50}$ | HT-29 IC$_{50}$ | Purity retention time mass found |
|---|---|---|---|---|
| 97 | 2-(2-Aminopyridin-3-yl)-N-(4-methoxybenzyl)pyrimidin-4-amine | D | | 98%, RT: 2.61 min 308 [M + H]+. 1H NMR (400 MHz, DMSO-D$_6$) δ 8.98 (d, J = 7.5, 1H), 8.85 (s, 1H), 8.22 (d, J = 5.3, 1H), 8.20 (d, J = 6.2, 1H), 7.31 (d, J = 8.5, 2H), 7.06 (dd, J = 7.4, 6.4, 1H), 6.91 (d, J = 8.4, 2H), 6.68 (d, J = 6.2, 1H), 4.58 (d, J = 5.0, 2H), 3.72 (s, 3H) |
| 98 | 2-(2-Aminopyridin-3-yl)-N-(2,4-difluorobenzyl)pyrimidin-4-amine | B | D | 98%, RT: 2.91 min 314 [M + H]+. 1H NMR (400 MHz, DMSO-D$_6$) δ 8.97 (d, J = 7.2, 1H), 8.85 (s, 1H), 8.22 (d, J = 5.9, 2H), 7.51 (dd, J = 15.4, 8.5, 1H), 7.28 (t, J = 8.9, 1H), 7.09 (d, J = 9.3, 1H), 7.06 (dd, J = 7.6, 6.3, 1H), 6.70 (d, J = 6.1, 1H), 4.66 (d, J = 4.7, 2H) |
| 99 | 2-(2-Aminopyridin-3-yl)-N-[4-(methylsulfonyl)benzyl]pyrimidin-4-amine | D | | 98%, RT: 2.22 min 356 [M + H]+. 1H NMR (400 MHz, DMSO-D$_6$) δ 8.94 (d, J = 7.3, 1H), 8.86 (s, 1H), 8.24 (d, J = 6.0, 1H), 8.18 (d, J = 5.8, 1H), 7.90 (d, J = 8.0, 2H), 7.64 (d, J = 8.3, 2H), 7.02 (t, J = 6.7, 1H), 6.71 (d, J = 6.0, 1H), 4.77 (d, J = 5.1, 2H), 3.19 (s, 3H) |

TABLE 3-continued

| Structure | Chemical Name | FAK IC$_{50}$ | HT-29 IC$_{50}$ | Purity retention time mass found |
|---|---|---|---|---|
| 100 | 2-(2-Aminopyridin-3-yl)-N-{[3-(trifluoromethyl)pyridin-2-yl]methyl}pyrimidin-4-amine | C | | 98%, RT: 2.71 min 347 [M + H]+. 1H NMR (400 MHz, DMSO-D$_6$) δ 8.91 (s, 1H), 8.86-8.74 (m, 2H), 8.42-8.00 (m, 3H), 7.58 (dd, J = 6.7, 5.1, 1H), 7.02 (t, J = 6.8, 1H), 6.82 (d, J = 6.2, 1H), 4.95 (s, 2H) |
| 101 | 2-(2-Aminopyridin-3-yl)-N-(2-fluoro-4-methylbenzyl)pyrimidin-4-amine | C | | 99.9%, RT: 3.11 min 310 [M + H]+. 1H NMR (400 MHz, DMSO-D$_6$) δ 9.02 (d, J = 7.2, 1H), 8.55 (s, 1H), 8.20 (t, J = 6.6, 2H), 7.31 (t, J = 8.0, 1H), 7.10-7.02 (m, 2H), 6.99 (d, J = 7.9, 1H), 6.64 (d, J = 6.2, 1H), 4.63 (d, J = 5.0, 2H), 2.29 (s, 3H) |
| 102 | 2-(2-Aminopyridin-3-yl)-N-[5-fluoro-2-(trifluoromethyl)benzyl]pyrimidin-4-amine | C | | 97%, RT: 3.58 min 364 [M + H]+. 1H NMR (400 MHz, DMSO-D$_6$) δ 8.46 (t, J = 5.4, 1H), 8.00 (d, J = 5.7, 1H), 7.84 (dd, J = 9.1, 5.5, 1H), 7.46-7.26 (m, 2H), 6.62 (d, J = 5.7, 1H), 4.68 (d, J = 4.6, 2H) |
| 103 | 2-(2-Aminopyridin-3-yl)-N-{[4-(trifluoromethyl)pyridin-3-yl]methyl}pyrimidin-4-amine | C | | 99.9%, RT: 2.70 min 347 [M + H]+. 1H NMR (400 MHz, DMSO-D$_6$) δ 8.88 (s, 1H), 8.86 (d, J = 7.7, 1H), 8.79 (d, J = 4.8, 1H), 8.27 (d, J = 6.0, 1H), 8.19 (d, J = 5.4, 1H), 7.81 (d, J = 5.0, 1H), 7.02 (t, J = 6.8, 1H), 6.76 (d, J = 6.1, 1H), 4.87 (d, J = 4.0, 2H) |

TABLE 3-continued

| Structure | Chemical Name | FAK IC$_{50}$ | HT-29 IC$_{50}$ | Purity retention time mass found |
|---|---|---|---|---|
| 104 | 3-(3-{[2-(Trifluoromethyl)benzyl]amino}phenyl)pyridin-2-amine | D | | 98%, RT: 4.14 min 344 [M + H]+. 1H NMR (400 MHz, DMSO-D$_6$) δ 7.95 (dd, J = 6.2, 1.7, 1H), 7.79-7.71 (m, 2H), 7.63 (d, J = 4.0, 2H), 7.55-7.37 (m, 3H), 7.22 (t, J = 8.0, 1H), 6.93 (dd, J = 7.3, 6.3, 1H), 6.68 (s, 1H), 6.64-6.54 (m, 3H), 4.48 (s, 2H) |
| 105 | 3-{3-[(2-Fluorobenzyl)amino]phenyl}pyridin-2-amine | D | | 96%, RT: 3.42 min 294 [M + H]+. 1H NMR (400 MHz, DMSO-D6) δ 9.17 (s, 1H), 8.05 (dd, J = 6.2, 1.3, 1H), 7.79 (dd, J = 7.3, 1.5, 3H), 7.49 (t, J = 7.7, 1H), 7.39-7.24 (m, 2H), 7.25-7.10 (m, 2H), 6.97 (dd, J = 7.2, 6.4, 1H), 6.93-6.81 (m, 2H), 6.78 (d, J = 7.1, 1H), 4.39 (s, 2H) |
| 106 | N4-(2-Fluorobenzyl)-2,3'-bipyridine-2',4-diamine | D | | 98%, RT: 2.27 min 295 [M + H]+. 1H NMR (400 MHz, DMSO-D$_6$) δ 9.42 (s, 1H), 8.33 (s, 1H), 8.21 (dd, J = 6.1, 1.6, 1H), 8.06 (dd, J = 7.4, 1.4, 1H), 7.48 (t, J = 7.3, 1H), 7.43-7.36 (m, 1H), 7.31-7.19 (m, 2H), 7.09 (s, 1H), 7.02 (d, J = 6.2, 1H), 7.01 (d, J = 6.2, 1H), 4.62 (s, 2H) |
| 107 | 2-(5-Fluoropyridin-3-yl)-N-[2-(trifluoromethyl)benzyl]pyrimidin-4-amine | B | D | 96%, RT: 3.77 min 349 [M + H]+. 1H NMR (500 MHz, DMSO-D$_6$) δ 9.98 (s, 1H), 9.28 (s, 1H), 8.87 (d, J = 1.8, 1H), 8.63 (s, 1H), 8.30 (d, J = 6.4, 1H), 7.79 (d, J = 8.0, 1H), 7.73-7.60 (m, 2H), 7.52 (t, J = 7.3, 1H), 6.98 (d, J = 6.8, 1H), 4.97 (d, J = 4.4, 2H) |

TABLE 3-continued

| Structure | Chemical Name | FAK IC$_{50}$ | HT-29 IC$_{50}$ | Purity retention time mass found |
|---|---|---|---|---|
| 108 | 2-(5-Chloropyridin-3-yl)-N-[2-(trifluoromethyl)benzyl]pyrimidin-4-amine | A | C | 99.4%, RT: 3.92 min 365 [M + H]+ (35Cl) 1H NMR (500 MHz, DMSO-D$_6$) δ 9.98 (s, 1H), 9.28 (s, 1H), 8.87 (d, J = 1.8, 1H), 8.63 (s, 1H), 8.30 (d, J = 6.4, 1H), 7.79 (d, J = 8.0, 1H), 7.73-7.60 (m, 2H), 7.52 (t, J = 7.3, 1H), 6.98 (d, J = 6.8, 1H), 4.97 (d, J = 4.4, 2H) |
| 109 | 2-(2-Aminopyridin-3-yl)-N-[4-chloro-2-(trifluoromethyl)benzyl]pyrimidin-4-amine | B |  | 99.1%, RT: 3.89 min 380 [M + H]+ (35Cl) 1H NMR (500 MHz, DMSO-D$_6$) δ 8.83 (s, 1H), 8.65 (s, 1H), 8.26 (s, 1H), 8.15 (s, 1H), 7.82 (s, 1H), 7.73 (d, J = 8.0, 1H), 7.58 (d, J = 8.4, 1H), 6.99 (s, 1H), 6.73 (s, 1H), 4.79 (s, 2H) |
| 110 | 2-(2-Aminopyridin-3-yl)-N-[4-fluoro-2-(trifluoromethyl)benzyl]pyrimidin-4-amine | A | C | 99.4%, RT: 3.59 min 364 [M + H]+. 1H NMR (500 MHz, DMSO-D$_6$) δ 8.87 (s, 1H), 8.63 (s, 1H), 8.26 (s, 1H), 8.17 (s, 1H), 7.76-7.59 (m, 2H), 7.54 (t, J = 8.4, 1H), 7.01 (t, J = 6.6, 1H), 6.73 (s, 1H), 4.80 (s, 2H) |
| 111 | 2-(2-Aminopyridin-3-yl)-N-[2-fluoro-6-(trifluoromethyl)benzyl]pyrimidin-4-amine | C |  | 99.7%, RT: 3.41 min 364 [M + H]+. 1H NMR (400 MHz, DMSO-D$_6$) δ 9.07 (d, J = 7.3, 1H), 8.41 (s, 1H), 8.23 (s, 2H), 7.79-7.58 (m, 3H), 7.08 (t, J = 7.2, 1H), 6.62 (d, J = 6.0, 1H), 4.79 (s, 2H) |

TABLE 3-continued

| | Structure | Chemical Name | FAK IC$_{50}$ | HT-29 IC$_{50}$ | Purity retention time mass found |
|---|---|---|---|---|---|
| 112 | 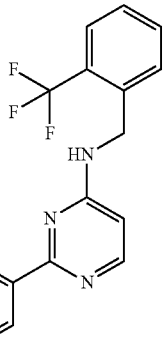 | N-[2-(Trifluoromethyl)benzyl]-2-[5-(trifluoromethyl)pyridin-3-yl]pyrimidin-4-amine | A | C | 98.7%, RT: 4.30 min 399 [M + H]+. 1H NMR (500 MHz, DMSO-D$_6$) δ 9.58 (s, 1H), 9.49 (s, 1H), 9.15 (s, 1H), 8.73 (s, 1H), 8.32 (d, J = 6.1, 1H), 7.77 (d, J = 7.8, 1H), 7.69-7.58 (m, 2H), 7.50 (t, J = 7.5, 1H), 6.91 (d, J = 6.3, 1H) |
| 113 | 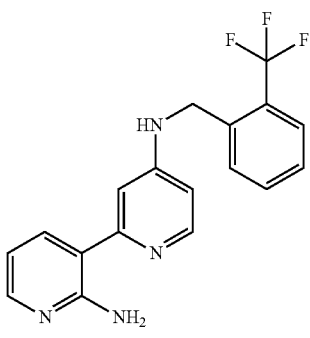 [SMILES: Nc1ncccc1-c1cc(NCc2ccccc2C(F)(F)F)ccn1] | N4-[2-(trifluoromethyl)benzyl]-2,3'-bipyridine-2',4-diamine | | C | 95%, RT: 2.79 min 345 [M + H]+. 1H NMR (500 MHz, DMSO-D$_6$) δ 9.44 (s, 1H), 8.28 (s, 1H), 8.21 (d, J = 4.7, 1H), 8.07 (d, J = 6.7, 1H), 7.81 (d, J = 7.9, 1H), 7.71 (t, J = 7.5, 1H), 7.66-7.51 (m, 2H), 7.26-6.79 (m, 3H), 4.73 (d, J = 4.6, 2H) |
| 114 | 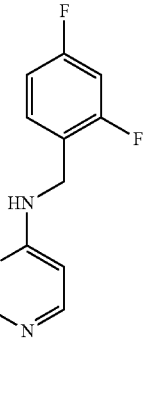 | 2-(5-Chloropyridin-3-yl)-N-(2,4-difluorobenzyl)pyrimidin-4-amine | A | B | 92%, RT: 3.65 min 333 [M + H]+ (35Cl). 1H NMR (500 MHz, DMSO-D$_6$) δ 9.37 (s, 1H), 8.89 (s, 1H), 8.73 (s, 1H), 8.26 (d, J = 6.4, 1H), 7.54 (s, 1H), 7.28 (t, J = 9.8, 1H), 7.09 (t, J = 8.5, 1H), 6.85 (s, 1H), 4.80 (s, 2H) |
| 115 | 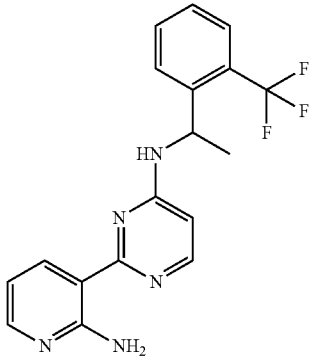 [SMILES: CC(Nc1ccnc(-c2cccnc2N)n1)c1ccccc1C(F)(F)F] | 2-(2-Aminopyridin-3-yl)-N-{1-[2-(trifluoromethyl)phenyl]ethyl}pyrimidin-4-amine | B | D | 98.5%, RT: 3.80 min 360 [M + H]+. 1H NMR (500 MHz, DMSO-D$_6$) δ 8.66 (s, 1H), 8.21 (s, 1H), 8.15 (s, 1H), 7.90-7.58 (m, 3H), 7.46 (s, 1H), 6.97 (s, 1H), 6.75 (s, 1H), 5.55 (s, 1H), 1.52 (d, J = 5.7, 3H) |

TABLE 3-continued

| | Structure | Chemical Name | FAK IC$_{50}$ | HT-29 IC$_{50}$ | Purity retention time mass found |
|---|---|---|---|---|---|
| 116 | 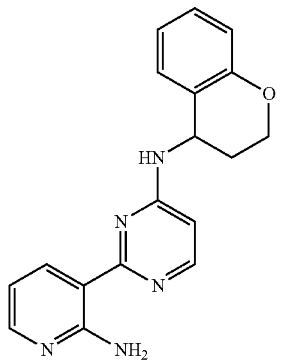 [SMILES: Nc1ncccc1-c1nccc(NC2CCOc3ccccc32)n1] | 2-(2-Aminopyridin-3-yl)-N-(3,4-dihydro-2H-chromen-4-yl)pyrimidin-4-amine | D | | 98%, RT: 3.01 min 320 [M + H]+. 1H NMR (500 MHz, DMSO-D$_6$) δ 9.09 (d, J = 6.8, 1H), 8.53 (s, 1H), 8.23 (d, J = 5.8, 1H), 8.20 (d, J = 5.0, 1H), 7.31-7.15 (m, 2H), 7.05 (dd, J = 7.5, 6.3, 1H), 6.89 (t, J = 7.2, 1H), 6.84 (d, J = 8.2, 1H), 6.62 (s, 1H), 5.45 (br s, 1H), 4.29 (br s, 1H), 4.26-4.18 (m, 1H), 2.20 (br s, 1H), 2.08 (br s, 1H) |
| 117 | 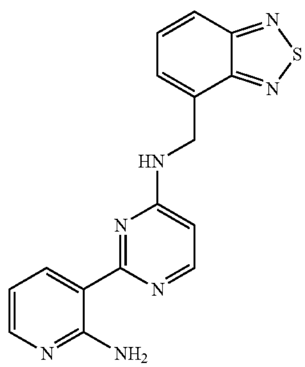 [SMILES: Nc1ncccc1-c1nccc(NCc2cccc3nsnc23)n1] | 2-(2-Aminopyridin-3-yl)-N-(2,1,3-benzothiadiazol-4-ylmethyl)pyrimidin-4-amine | B | | 83%, RT: 2.75 min 336 [M + H]+. 1H NMR (500 MHz, DMSO-D$_6$) δ 8.89 (s, 1H), 8.72 (s, 1H), 8.24 (s, 1H), 8.14 (s, 1H), 8.02 (d, J = 8.3, 1H), 7.76-7.67 (m, 1H), 7.64 (d, J = 6.6, 1H), 6.97 (s, 1H), 6.71 (s, 1H), 5.16 (s, 2H) |
| 118 | 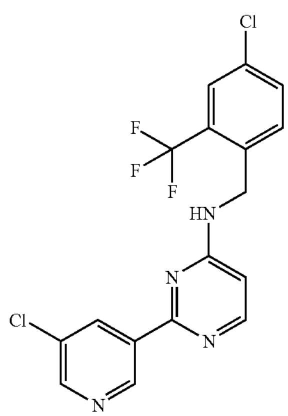 [SMILES: FC(F)(F)c1cc(Cl)ccc1CNc1ccnc(-c2cncc(Cl)c2)n1] | 2-(5-Chloropyridin-3-yl)-N-[4-chloro-2-(trifluoromethyl)benzyl]pyrimidin-4-amine | A | C | 95%, RT: 4.41 min 401 [M + H]+ (35Cl + 37Cl). 1H NMR (500 MHz, DMSO-D$_6$) δ 9.23 (s, 1H), 9.12 (s, 1H), 8.79 (d, J = 1.7, 1H), 8.49 (s, 1H), 8.30 (d, J = 6.1, 1H), 7.84 (d, J = 1.7, 1H), 7.75 (d, J = 8.5, 1H), 7.62 (d, J = 8.5, 1H), 6.82 (s, 1H), 4.89 (s, 2H) |
| 119 | 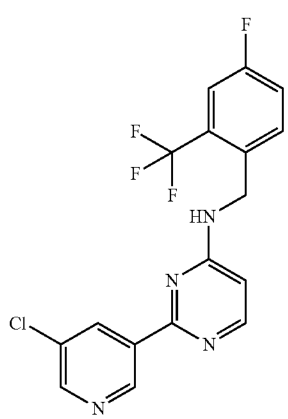 [SMILES: Fc1ccc(CNc2ccnc(-c3cncc(Cl)c3)n2)c(C(F)(F)F)c1] | 2-(5-Chloropyridin-3-yl)-N-[4-fluoro-2-(trifluoromethyl)benzyl]pyrimidin-4-amine | A | C | 99.1%, RT: 4.18 min 383 [M + H]+ (35Cl). 1H NMR (500 MHz, DMSO-D$_6$) δ 9.32 (s, 1H), 9.26 (s, 1H), 8.82 (s, 1H), 8.55 (s, 1H), 8.30 (d, J = 5.6, 1H), 7.76-7.61 (m, 2H), 7.55 (td, J = 8.2, 2.0, 1H), 6.85 (s, 1H), 4.90 (s, 2H) |

TABLE 3-continued

| Structure | Chemical Name | FAK IC$_{50}$ | HT-29 IC$_{50}$ | Purity retention time mass found |
|---|---|---|---|---|
| 120 | 2-[2-(2-Aminopyridin-3-yl)pyrimidin-4-yl]isoindolin-1-one | D | | 98.5%, RT: 3.18 min 304 [M + H]+. 1H NMR (500 MHz, DMSO-D$_6$) δ 9.22 (dd, J = 7.7, 1.6, 1H), 8.90 (d, J = 5.9, 1H), 8.39 (d, J = 5.9, 1H), 8.30 (dd, J = 6.1, 1.6, 1H), 7.89 (d, J = 7.6, 1H), 7.83-7.73 (m, 2H), 7.61 (t, J = 7.3, 1H), 7.13 (dd, J = 7.6, 6.2, 1H), 5.26 (s, 2H) |
| 121 | 2-(2-Aminopyridin-3-yl)-N-(pyridin-3-ylmethyl)pyrimidin-4-amine | D | | 96%, RT: 1.50 min 279 [M + H]+. 1H NMR (500 MHz, DMSO-D$_6$) δ 8.98 (s, 2H), 8.91 (s, 1H), 8.82 (d, J = 5.0, 1H), 8.55 (d, J = 7.1, 1H), 8.27 (s, 1H), 8.19 (d, J = 4.6, 1H), 8.02 (dd, J = 7.6, 5.8, 1H), 7.02 (t, J = 6.7, 1H), 6.74 (d, J = 6.1, 1H), 4.87 (s, 2H) |
| 122 | 2-(2-Aminopyridin-3-yl)-N-(1,3-benzodioxol-4-ylmethyl)pyrimidin-4-amine | B | | 94%, RT: 2.44 min 322 [M + H]+. 1H NMR (500 MHz, DMSO-D$_6$) δ 9.03 (d, J = 7.4, 1H), 8.60 (s, 1H), 8.20 (s, 2H), 7.06 (t, J = 6.8, 1H), 6.94-6.76 (m, 3H), 6.65 (d, J = 5.9, 1H), 6.06 (s, 2H), 4.59 (s, 2H) |
| 123 | N-[4-Fluoro-2-(trifluoromethyl)benzyl]-2-[5-(trifluoromethyl)pyridin-3-yl]pyrimidin-4-amine | A | C | 91%, RT: 4.23 min 417 [M + H]+. 1H NMR (500 MHz, DMSO-D$_6$) δ 9.57 (s, 1H), 9.28 (s, 1H), 9.14 (s, 1H), 8.70 (s, 1H), 8.32 (d, J = 6.3, 1H), 7.72-7.61 (m, 2H), 7.53 (td, J = 9.0, 2.3, 1H), 6.86 (s, 1H), 4.88 (s, 2H) |

TABLE 3-continued

| Structure | Chemical Name | FAK IC$_{50}$ | HT-29 IC$_{50}$ | Purity retention time mass found |
|---|---|---|---|---|
| 124 | 2-(5-Chloropyridin-3-yl)-N-{1-[2-(trifluoromethyl)phenyl]ethyl}pyrimidin-4-amine | A | C | 95%, RT: 4.06 min 379 [M + H]+ (35Cl). 1H NMR (500 MHz, DMSO-D$_6$) δ 9.14 (s, 1H), 8.71 (s, 2H), 8.31 (s, 1H), 8.23 (d, J = 6.1, 1H), 7.86-7.69 (m, 2H), 7.66 (t, J = 7.7, 1H), 7.45 (t, J = 7.4, 1H), 6.70 (s, 1H), 5.56 (s, 1H), 1.52 (d, J = 6.7, 3H) |
| 125 | N-(2,4-Difluorobenzyl)-2-[5-(trifluoromethyl)pyridin-3-yl]pyrimidin-4-amine | A | C | 97%, RT: 3.88 min 367 [M + H]+. 1H NMR (500 MHz, DMSO-D$_6$) δ 9.95 (s, 1H), 9.71 (s, 1H), 9.25 (s, 1H), 8.98 (s, 1H), 8.29 (d, J = 6.7, 1H), 7.56 (d, J = 7.3, 1H), 7.28 (t, J = 9.8, 1H), 7.09 (t, J = 8.0, 1H), 6.92 (s, 1H), 4.81 (s, 2H) |
| 126 | 2-(2-Amino-5-chloropyridin-3-yl)-N-(2,4-difluorobenzyl)pyrimidin-4-amine | A | C | 98%, RT: 3.58 min 348 [M + H]+ (35Cl). 1H NMR (500 MHz, DMSO-D$_6$) δ 9.06 (s, 1H), 8.49 (s, 1H), 8.27 (s, 1H), 8.20 (d, J = 6.2, 1H), 7.49 (d, J = 7.5, 1H), 7.28 (t, J = 9.9, 1H), 7.09 (t, J = 8.0, 1H), 6.69 (d, J = 6.0, 1H), 4.66 (s, 2H) |
| 127 | N-(1,3-Benzodioxol-4-ylmethyl)-2-(5-chloropyridin-3-yl)pyrimidin-4-amine | A | D | 98%, RT: 3.37 min 341 [M + H]+ (35Cl). 1H NMR (500 MHz, DMSO-D$_6$) δ 10.28 (s, 1H), 9.44 (s, 1H), 8.93 (d, J = 2.2, 1H), 8.85 (s, 1H), 8.24 (d, J = 7.0, 1H), 6.95 (d, J = 7.2, 1H), 6.91 (d, J = 7.5, 1H), 6.89-6.79 (m, 2H), 6.06 (s, 2H), 4.75 (d, J = 5.4, 2H) |

TABLE 3-continued

| Structure | Chemical Name | FAK IC$_{50}$ | HT-29 IC$_{50}$ | Purity retention time mass found |
|---|---|---|---|---|
| 128 | 2-(2-Aminopyridin-3-yl)-N-(pyridin-4-ylmethyl)pyrimidin-4-amine | D | | 97%, RT: 1.51 min 279 [M + H]+. 1H NMR (500 MHz, DMSO-D$_6$) δ 8.97 (s, 1H), 8.90-8.74 (m, 3H), 8.30 (s, 1H), 8.16 (s, 1H), 8.02 (d, J = 4.1, 2H), 6.97 (s, 1H), 6.81 (s, 1H), 4.95 (s, 2H) |
| 129 | 2-(2-Amino-5-chloropyridin-3-yl)-N-[2-(trifluoromethyl)benzyl]pyrimidin-4-amine | A | C | 97%, RT: 3.95 min 380 [M + H]+ (35Cl). 1H NMR (500 MHz, DMSO-D$_6$) δ 8.63 (s, 1H), 8.40 (s, 1H), 8.25 (d, J = 6.0, 2H), 7.78 (d, J = 7.6, 1H), 7.66 (t, J = 7.5, 1H), 7.58 (d, J = 7.5, 1H), 7.50 (t, J = 7.3, 1H), 6.79 (d, J = 5.4, 1H), 4.83 (d, J = 4.4, 2H) |
| 130 | N-{1-[2-(Trifluoromethyl)phenyl]ethyl}-2-[5-(trifluoromethyl)pyridin-3-yl]pyrimidin-4-amine | A | D | 97%, RT: 4.33 min 413 [M + H]+. 1H NMR (500 MHz, DMSO-D$_6$) δ 9.76 (s, 1H), 9.48 (s, 1H), 9.14 (s, 1H), 8.58 (s, 1H), 8.29 (d, J = 6.5, 1H), 7.77 (d, J = 7.9, 1H), 7.73 (d, J = 7.8, 1H), 7.68 (t, J = 7.4, 1H), 7.46 (t, J = 7.5, 1H), 6.93 (d, J = 6.3, 1H), 5.73-5.45 (m, 1H), 1.55 (d, J = 6.8, 3H) |
| 131 | N-(2,1,3-Benzothiadiazol-4-ylmethyl)-2-(5-chloropyridin-3-yl)pyrimidin-4-amine | A | D | 94%, RT: 3.30 min 355 [M + H]+ (35Cl). 1H NMR (500 MHz, DMSO-D$_6$) δ 9.78 (s, 1H), 9.27 (s, 1H), 8.84 (s, 1H), 8.61 (s, 1H), 8.28 (d, J = 6.5, 1H), 8.05 (d, J = 8.4, 1H), 7.78-7.64 (m, 2H), 6.89 (d, J = 6.3, 1H), 5.29 (s, 2H) |

TABLE 3-continued

| Structure | Chemical Name | FAK IC50 | HT-29 IC50 | Purity retention time mass found |
|---|---|---|---|---|
| 132 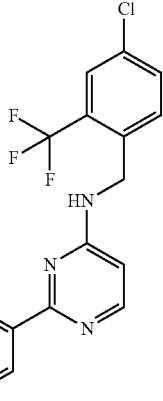 | N-[4-Chloro-2-(trifluoromethyl)benzyl]-2-[5-(trifluoromethyl)pyridin-3-yl]pyrimidin-4-amine | A | C | 84%, RT: 4.61 min 433 [M + H]+ (35Cl). 1H NMR (500 MHz, DMSO-D$_6$) δ 9.71 (s, 1H), 9.57 (s, 1H), 9.17 (s, 1H), 8.71 (s, 1H), 8.34 (d, J = 6.4, 1H), 7.83 (s, 1H), 7.74 (d, J = 8.0, 1H), 7.63 (d, J = 8.4, 1H), 6.95 (d, J = 6.5, 1H), 4.91 (d, J = 4.5, 2H) |
| 133 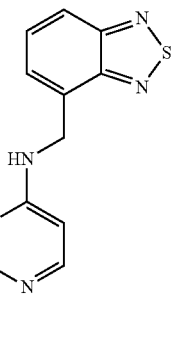 | N-(2,1,3-Benzothiadiazol-4-ylmethyl)-2-[5-(trifluoromethyl)pyridin-3-yl]pyrimidin-4-amine | A | | 98%, RT: 3.64 min 389 [M + H]+. 1H NMR (500 MHz, DMSO-D$_6$) δ 9.98 (s, 1H), 9.60 (s, 1H), 9.20 (s, 1H), 8.89 (s, 1H), 8.31 (d, J = 6.8, 1H), 8.04 (s, 1H), 7.78-7.59 (m, 2H), 6.95 (d, J = 6.1, 1H), 5.30 (d, J = 5.0, 2H) |
| 134 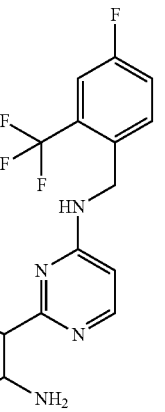 | 2-(2-Amino-5-chloropyridin-3-yl)-N-[4-fluoro-2-(trifluoromethyl)benzyl]pyrimidin-4-amine | A | C | 96%, RT: 4.10 min 398 [M + H]+ (35Cl). 1H NMR (500 MHz, DMSO-D$_6$) δ 9.12 (s, 1H), 8.41 (s, 1H), 8.25 (s, 2H), 7.67 (d, J = 7.5, 1H), 7.62 (s, 1H), 7.53 (t, J = 7.3, 1H), 6.78 (d, J = 4.2, 1H), 4.79 (s, 2H) |
| 135 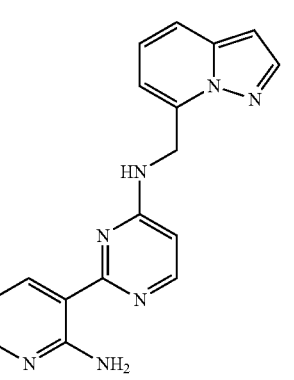 | 2-(2-Aminopyridin-3-yl)-N-(pyrazolo[1,5-a]pyridin-7-ylmethyl)pyrimidin-4-amine | D | | 91%, RT: 2.57 min 318 [M + H]+. 1H NMR (500 MHz, DMSO-D$_6$) δ 8.81 (s, 2H), 8.26 (d, J = 6.0, 1H), 8.16 (s, 1H), 8.12 (s, 1H), 7.68 (d, J = 9.1, 1H), 7.22 (t, J = 7.5, 1H), 6.97 (s, 1H), 6.91 (dd, J = 6.2, 3.6, 1H), 6.78 (t, J = 6.8, 1H), 6.73 (d, J = 1.4, 1H), 5.15 (s, 2H) |

TABLE 3-continued

| Structure | Chemical Name | FAK IC$_{50}$ | HT-29 IC$_{50}$ | Purity retention time mass found |
|---|---|---|---|---|
| 136 | 2-[2-Amino-5-(trifluoromethyl)pyridin-3-yl]-N-[2-(trifluoromethyl)benzyl]pyrimidin-4-amine | A | | 99.6%, RT: 4.30 min 414 [M + H]+. 1H NMR (500 MHz, DMSO-D$_6$) δ 9.11 (s, 1H), 8.51 (s, 1H), 8.48 (s, 1H), 8.26 (d, J = 5.8, 1H), 7.76 (d, J = 7.8, 1H), 7.63 (t, J = 7.7, 1H), 7.56 (d, J = 6.7, 1H), 7.48 (t, J = 7.2, 1H), 6.80 (s, 1H), 4.83 (s, 2H) |
| 137 | 2-(2-Aminopyridin-3-yl)-N-{[2-(trifluoromethyl)pyridin-3-yl]methyl}pyrimidin-4-amine | C | | 98.6%, RT: 2.65 min 347 [M + H]+. 1H NMR (500 MHz, DMSO-D$_6$) δ 8.81 (s, 2H), 8.64 (s, 1H), 8.27 (d, J = 5.1, 1H), 8.17 (d, J = 4.5, 1H), 8.04 (d, J = 7.9, 1H), 7.71 (s, 1H), 6.99 (t, J = 6.9, 1H), 6.77 (d, J = 5.2, 1H), 4.86 (s, 2H) |
| 138 Chiral | 2-(2-Aminopyridin-3-yl)-N-{(1S)-1-[2-(trifluoromethyl)phenyl]ethyl}pyrimidin-4-amine | C | | 97.8%, RT: 3.63 min 360 [M + H]+. 1H NMR (500 MHz, DMSO-D$_6$) δ 8.88 (d, J = 7.2, 1H), 8.74 (s, 1H), 8.20 (d, J = 5.2, 1H), 8.16 (d, J = 4.9, 1H), 7.83 (s, 1H), 7.75 (d, J = 5.7, 1H), 7.58 (s, 2H), 6.97 (t, J = 6.5, 1H), 6.68 (s, 1H), 5.34 (s, 1H), 1.53 (d, J = 6.6, 3H) |
| 139 | N-Benzyl-2-pyridin-3-ylpyrimidin-4-amine | D | | 90%, RT: 263 [M + H]+. 1H NMR (400 MHz, DMSO-D$_6$) δ 9.77 (s, 1H), 9.46 (d, J = 1.4, 1H), 8.91 (dd, J = 5.0, 1.3, 1H), 8.83 (d, J = 8.3, 1H), 8.26 (d, J = 6.9, 1H), 7.82 (dd, J = 7.8, 5.2, 1H), 7.42 (d, J = 7.3, 2H), 7.37 (t, J = 7.5, 2H), 7.29 (t, J = 7.1, 1H), 6.85 (d, J = 6.9, 1H), 4.81 (d, J = 5.6, 2H) |

TABLE 3-continued

| Structure | Chemical Name | FAK IC$_{50}$ | HT-29 IC$_{50}$ | Purity retention time mass found |
|---|---|---|---|---|
| 140 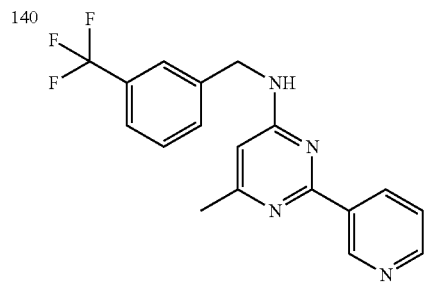 | 6-Methyl-2-pyridin-3-yl-N-[3-(trifluoromethyl)benzyl]pyrimidin-4-amine | D | | 1H NMR (400 MHz, DMSO-D$_6$) δ 10.26 (s, 1H), 9.56 (d, J = 1.4, 1H), 9.04 (d, J = 7.2, 1H), 8.98 (d, J = 5.0, 1H), 7.93 (dd, J = 7.9, 5.3, 1H), 7.81 (s, 1H), 7.73 (d, J = 7.3, 1H), 7.67-7.55 (m, 2H), 6.79 (s, 1H), 4.89 (d, J = 5.5, 2H), 2.53 (s, 3H) |
| 141 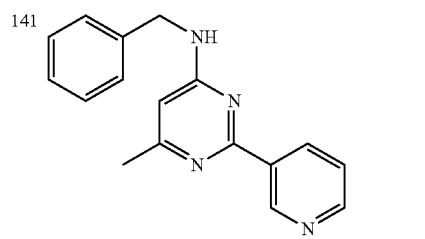 | N-Benzyl-6-methyl-2-pyridin-3-ylpyrimidin-4-amine | D | | 1H NMR (400 MHz, DMSO-D$_6$) δ 9.87 (s, 1H), 9.44 (s, 1H), 8.92 (dd, J = 5.0, 1.2, 1H), 8.85 (d, J = 7.7, 1H), 7.83 (dd, J = 7.6, 5.3, 1H), 7.42-7.34 (m, 4H), 7.28 (t, J = 7.2, 1H), 6.70 (s, 1H), 4.79 (d, J = 5.4, 2H), 2.50 (s, 3H) |
| 142 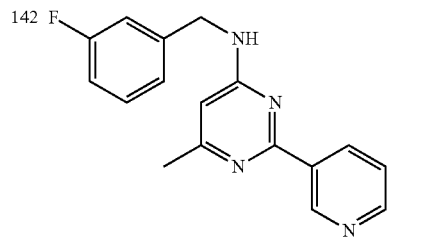 | N-(3-Fluorobenzyl)-6-methyl-2-pyridin-3-ylpyrimidin-4-amine | D | | 1H NMR (400 MHz, DMSO-D$_6$) δ 10.06 (s, 1H), 9.50 (s, 1H), 9.08-8.83 (m, 2H), 7.90 (dd, J = 7.7, 5.5, 1H), 7.40 (dd, J = 14.2, 8.0, 1H), 7.29-7.17 (m, 2H), 7.11 (t, J = 8.3, 1H), 6.76 (s, 1H), 4.82 (d, J = 5.6, 2H), 2.52 (s, 3H) |
| 143 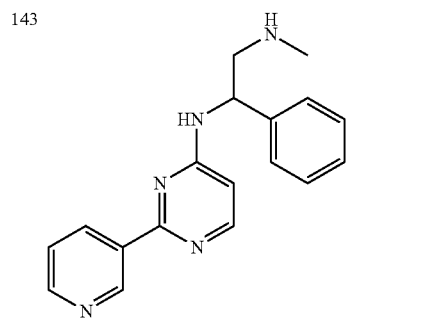 | N2-Methyl-1-phenyl-N1-(2-pyridin-3-ylpyrimidin-4-yl)ethane-1,2-diamine | D | | 99.3%, RT: 2.05 min 306 [M + H]+. 1H NMR (500 MHz, DMSO-D$_6$) δ 9.54 (s, 1H), 9.30 (s, 1H), 9.19 (s, 1H), 8.98 (d, J = 6.0, 1H), 8.91 (d, J = 4.7, 1H), 8.31 (d, J = 6.3, 1H), 7.88 (s, 1H), 7.56 (d, J = 7.3, 2H), 7.41 (td, J = 7.6, 1.8, 2H), 7.33 (dd, J = 7.8, 6.0, 1H), 6.86 (d, J = 6.2, 1H), 5.96 (s, 1H), 3.47 (d, J = 9.8, 1H), 3.37 (s, 1H), 2.61 (d, J = 1.6, 3H) |
| 144 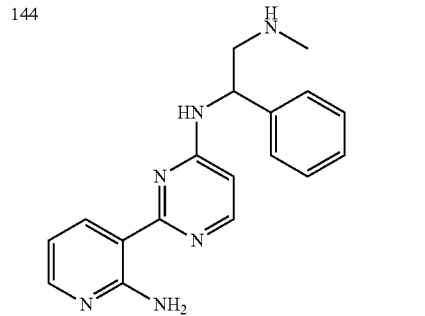 | N1-[2-(2-Aminopyridin-3-yl)pyrimidin-4-yl]-N2-methyl-1-phenylethane-1,2-diamine | D | | 99.3%, RT: 2.31 min 321 [M + H]+. 1H NMR (500 MHz, DMSO-D$_6$) δ 9.35 (s, 1H), 9.17 (s, 2H), 9.06 (d, J = 7.2, 1H), 9.04-8.97 (m, 1H), 8.27 (d, J = 5.3, 1H), 8.19 (d, J = 5.1, 1H), 7.52 (d, J = 7.7, 2H), 7.39 (t, J = 7.5, 2H), 7.31 (t, J = 6.9, 1H), 7.04 (t, J = 6.9, 1H), 6.72 (d, J = 5.7, 1H), 5.75 (s, 1H), 3.40 (d, J = 9.6, 1H), 3.35-3.25 (m, 1H), 2.59 (s, 3H) |

TABLE 3-continued

| Structure | Chemical Name | FAK IC$_{50}$ | HT-29 IC$_{50}$ | Purity retention time mass found |
|---|---|---|---|---|
| 145 | (S)-N1-[2-(2-Amino-pyridin-3-yl)-pyrimidin-4-yl]-1-(3-fluoro-phenyl)-N2-methyl-ethane-1,2-diamine | D | | 1H NMR (300 MHz, DMSO-D$_6$) δ 8.84 (s, 1H), 8.18 (d, J = 2.2, 1H), 7.97 (bs, 1H), 7.86 (d, J = 4.7, 1H), 7.80 (bs, 1H), 7.38 (bs, 1H), 7.39-7.35 (m, 1H), 7.25-7.20 (m, 2H), 7.05-7.01 (m, 1H), 6.90 (t, J = 4.1, 1H), 6.17 (bs, 1H), 5.16 (bs, 1H), 2.86-2.80 (m, 1H), 2.77-2.73 (m, 1H), 2.29 (s, 3H) |
| 146 | (S)-N1-[2-(2-Amino-pyridin-3-yl)-pyrimidin-4-yl]-N2-methyl-1-phenyl-ethane-1,2-diamine | D | | |
| 147 | (R)-N1-[2-(2-Amino-pyridin-3-yl)-pyrimidin-4-yl]-N2-methyl-1-phenyl-ethane-1,2-diamine | D | | |

TABLE 4

| Structure | Chemical Name |
|---|---|
| 148 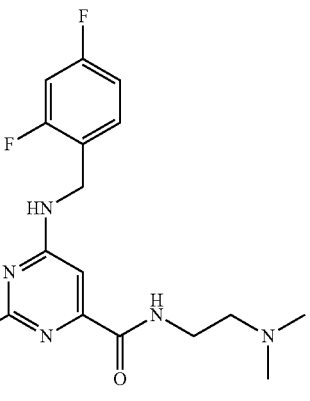 | 6-[(2,4-difluorophenyl)methylamino]-N-(2-dimethylaminoethyl)-2-[5-(trifluoromethyl)-3-pyridyl]pyrimidine-4-carboxamide<br>FAK: A<br>HT-29: B<br>HPLC Retention Time [min]: 3.8<br>HPLC: (Method A) RT 4.22 min, 93.1% (Max), 95.3% (254 nm).<br>LCMS Mass found [M + H]+: 367<br>LCMS: (Method A) 481.0 (M + H), RT. 4.2 min, 97.2% (Max), 97.2% (254 nm)<br>1HNMR (400 MHz, DMSO-d6): δ 9.92 (s, 1H), 9.12 (s, 1H), 9.01-8.96 (m, 2H), 8.61 (s, 1H), 7.50 (d, J = 8.0 Hz, 1H), 7.25-7.17 (m, 2H), 7.06-7.03 (m, 1H), 4.71 (d, J = 4.0 Hz, 2H), 3.31-3.28 (m, 4H), 2.21-2.18 (m, 6H). |
| 149 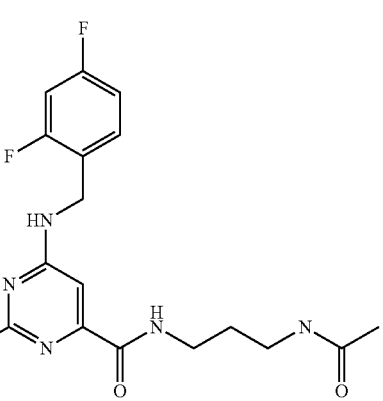 | N-(3-acetamidopropyl)-6-[(2,4-difluorophenyl)methylamino]-2-[5-(trifluoromethyl)-3-pyridyl]pyrimidine-4-carboxamide |
| 150 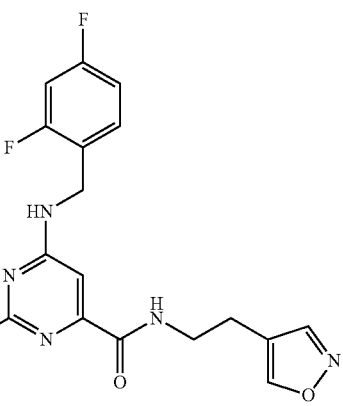 | 6-[(2,4-difluorophenyl)methylamino]-N-(2-isoxazol-4-ylethyl)-2-[5-(trifluoromethyl)-3-pyridyl]pyrimidine-4-carboxamide |

TABLE 4-continued

| Structure | Chemical Name |
|---|---|
| 151 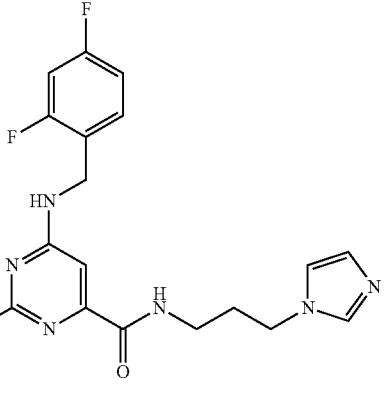 | 6-[(2,4-difluorophenyl)methylamino]-N-(3-imidazol-1-ylpropyl)-2-[5-(trifluoromethyl)-3-pyridyl]pyrimidine-4-carboxamide |
| 152 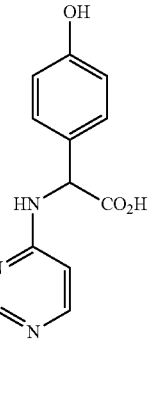 | 2-(4-hydroxyphenyl)-2-[[2-[5-(trifluoromethyl)-3-pyridyl]pyrimidin-4-yl]amino]acetic acid |
| 153 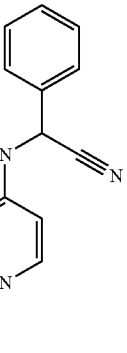 | 2-phenyl-2-[[2-[5-(trifluoromethyl)-3-pyridyl]pyrimidin-4-yl]amino]acetonitrile |
| 154 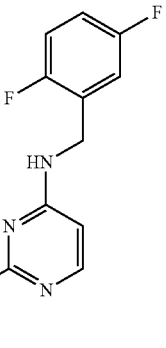 | N-[(2,5-difluorophenyl)methyl]-2-[5-(trifluoromethyl)-3-pyridyl]pyrimidin-4-amine<br>IC50 FAK: B<br>IC50 HT-29: C<br>HPLC Retention Time [min]: 3.8<br>HPLC: (Method A) RT 3.78 min, 99.4% (Max), 99.1% (254 nm).<br>LCMS Mass found [M + H]+: 367<br>LCMS: (Method A) 367.0 (M + H), RT. 3.76 min, 98.4% (Max), 99.0% (254 nm).<br>1H NMR: (400 MHz, DMSO-d6): δ 9.60 (d, J = 4.0 Hz, 1H), 9.12 (d, J = 4.0 Hz, 1H), 8.81 (s, 1H), 8.28-8.24 (m, 2H), 7.27-7.22 (m, 2H), 7.15-7.10 (m, 1H), 6.62 (d, J = 4.0 Hz, 1H), 4.72 (s, 2H). |

TABLE 4-continued
| Structure | Chemical Name |
| --- | --- |
| 155 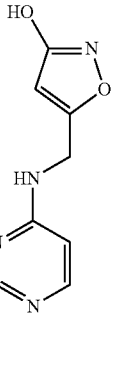 | N-[(3-fluoroisoxazol-5-yl)methyl]-2-[5-(trifluoromethyl)-3-pyridyl]pyrimidin-4-amine |
| 156 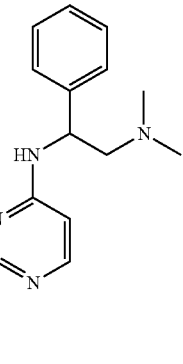 | N',N'-dimethyl-1-phenyl-N-[2-[5-(trifluoromethyl)-3-pyridyl]pyrimidin-4-yl]ethane-1,2-diamine |
| 157 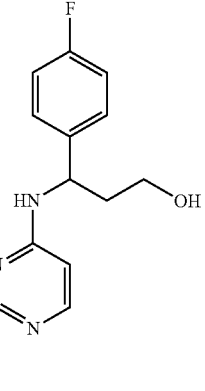 | 2-(4-fluorophenyl)-2-[[2-[5-(trifluoromethyl)-3-pyridyl]pyrimidin-4-yl]amino]ethanol |
| 158 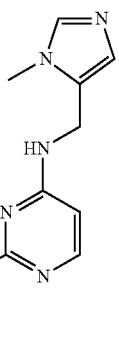 | N-[(3-methylimidazol-4-yl)methyl]-2-[5-(trifluoromethyl)-3-pyridyl]pyrimidin-4-amine |

TABLE 4-continued

| Structure | Chemical Name |
|---|---|
| 159 | 6-[(2,4-difluorophenyl)methylamino]-N-[2-(2-oxooxazolidin-3-yl)ethyl]-2-[5-(trifluoromethyl)-3-pyridyl]pyrimidine-4-carboxamide |
| 160 | 6-[(2,4-difluorophenyl)methylamino]-N-[2-(2-oxopyrrolidin-1-yl)ethyl]-2-[5-(trifluoromethyl)-3-pyridyl]pyrimidine-4-carboxamide<br>IC50 FAK: A<br>IC50 HT-29: B<br>HPLC Retention Time [min]: 4.8<br>HPLC: (Method A) RT 4.75 min, 96.2% (Max), 97.0% (254 nm).<br>LCMS Mass found [M + H]+: 521<br>LCMS: (Method A) 521.0 (M + H), RT. 4.51 min, 96.4% (Max), 97.3% (254 nm).<br>1H NMR: (400 MHz, DMSO-d6): δ 9.9 (s, 1H), 9.2 (s, 1H), 9.1 (s, 1H), 9.0 (s, 1H), 8.6 (t, J = 8.0 Hz, 1H), 7.5 (dd, J = 4.0, 8.0 Hz, 1H), 7.25-7.16 (m, 2H), 7.06-7.05 (m, 1H), 4.7 (d, J = 4.0 Hz, 2H), 3.43-3.69 (m, 6H), 2.19-2.15 (m, 2H), 1.93-1.86 (m, 2H). |
| 161 | 6-[(2,4-difluorophenyl)methylamino]-N-[(3-oxocyclobutyl)methyl]-2-[5-(trifluoromethyl)-3-pyridyl]pyrimidine-4-carboxamide |

TABLE 4-continued

| Structure | Chemical Name |
|---|---|
| 162 | 6-[(2,4-difluorophenyl)methylamino]-N-(4-hydroxycyclohexyl)-2-[5-(trifluoromethyl)-3-pyridyl]pyrimidine-4-carboxamide |
| 163 | 6-[(2,4-difluorophenyl)methylamino]-N-(4-oxocyclohexyl)-2-[5-(trifluoromethyl)-3-pyridyl]pyrimidine-4-carboxamide |
| 164 | N-(2,1,3-benzoxadiazol-4-yl)-6-[(2,4-difluorophenyl)methylamino]-2-[5-(trifluoromethyl)-3-pyridyl]pyrimidine-4-carboxamide |

TABLE 4-continued

| Structure | Chemical Name |
| --- | --- |
| 165 | N-(2,1,3-benzothiadiazol-4-yl)-6-[(2,4-difluorophenyl)methylamino]-2-[5-(trifluoromethyl)-3-pyridyl]pyrimidine-4-carboxamide |
| 166 | N-(5-carbamoyl-1H-imidazol-4-yl)-6-[(2,4-difluorophenyl)methylamino]-2-[5-(trifluoromethyl)-3-pyridyl]pyrimidine-4-carboxamide |
| 167 | 6-[(2,4-difluorophenyl)methylamino]-N-(1H-imidazol-2-ylmethyl)-2-[5-(trifluoromethyl)-3-pyridyl]pyrimidine-4-carboxamide |

TABLE 4-continued

| Structure | Chemical Name |
|---|---|
| 168 | 6-[(2,4-difluorophenyl)methylamino]-N-[(5-oxo-1,4-dihydro-1,2,4-triazol-3-yl)methyl]-2-[5-(trifluoromethyl)-3-pyridyl]pyrimidine-4-carboxamide |
| 169 | 6-[(2,4-difluorophenyl)methylamino]-N-[[1-(3-pyridyl)cyclopentyl]methyl]-2-[5-(trifluoromethyl)-3-pyridyl]pyrimidine-4-carboxamide |
| 170 | 6-[(2,4-difluorophenyl)methylamino]-N-imidazo[1,2-a]pyridin-5-yl-2-[5-(trifluoromethyl)-3-pyridyl]pyrimidine-4-carboxamide |

TABLE 4-continued

| Structure | Chemical Name |
|---|---|
| 171 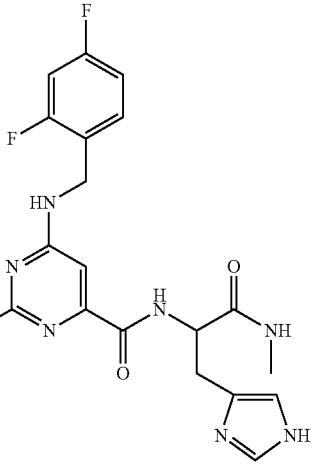 | 6-[(2,4-difluorophenyl)methylamino]-N-[1-(1H-imidazol-4-ylmethyl)-2-(methylamino)-2-oxo-ethyl]-2-[5-(trifluoromethyl)-3-pyridyl]pyrimidine-4-carboxamide |
| 172 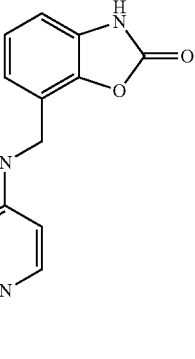 | 7-[[[2-[5-(trifluoromethyl)-3-pyridyl]pyrimidin-4-yl]amino]methyl]-3H-1,3-benzoxazol-2-one |
| 173 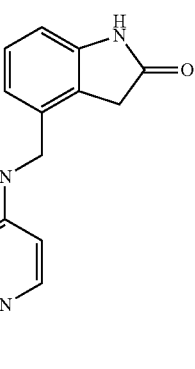 | 4-[[[2-[5-(trifluoromethyl)-3-pyridyl]pyrimidin-4-yl]amino]methyl]indolin-2-one |
| 174 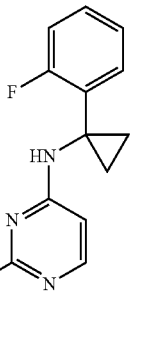 | N-[1-(2-fluorophenyl)cyclopropyl]-2-[5-(trifluoromethyl)-3-pyridyl]pyrimidin-4-amine |

TABLE 4-continued
| Structure | Chemical Name |
|---|---|
| 175 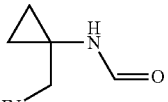 | N-[1-[[2-[5-(trifluoromethyl)-3-pyridyl]pyrimidin-4-yl]amino]cyclopropyl]formamide |
| 176 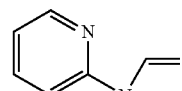 | N-[3-[[[2-[5-(trifluoromethyl)-3-pyridyl]pyrimidin-4-yl]amino]methyl]-2-pyridyl]formamide |
| 177 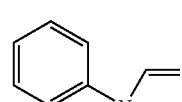 | N-[2-[[[2-[5-(trifluoromethyl)-3-pyridyl]pyrimidin-4-yl]amino]methyl]phenyl]formamide |
| 178 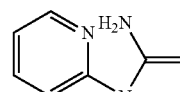 | [3-[[[2-[5-(trifluoromethyl)-3-pyridyl]pyrimidin-4-yl]amino]methyl]-2-pyridyl]urea |

TABLE 4-continued

| Structure | Chemical Name |
|---|---|
| 179 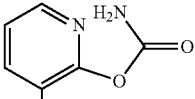 | [3-[[[2-[5-(trifluoromethyl)-3-pyridyl]pyrimidin-4-yl]amino]methyl]-2-pyridyl]carbamate |
| 180 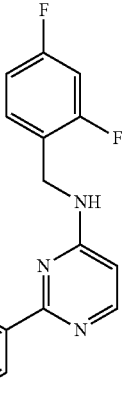 | 5-[4-[(2,4-difluorophenyl)methylamino]pyrimidin-2-yl]pyridine-3-carbonitrile<br>IC50 FAK: B<br>HPLC Retention Time [min]: 3.2<br>HPLC: (Method A) RT 3.20 min, 99.6% (Max), 99.9% (254 nm).<br>LCMS Mass found [M + H]+: 324.3<br>LCMS: (Method A) 324.0 (M + H), RT. 3.21 min, 99.4% (Max), 99.8% (254 nm).<br>1H NMR: (400 MHz, DMSO-d6): δ 9.61 (d, J = 4.0 Hz, 1H), 9.10 (d, J = 4.0 Hz, 1H), 8.91 (s, 1H), 8.23-8.19 (m, 2H), 7.52-7.46 (m, 1H), 7.27-7.21 (m, 1H), 7.07-7.02 (m, 1H), 6.61 (d, J = 4.0 Hz, 1H), 4.71 (s, 1H). |
| 181 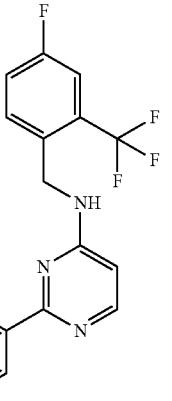 | 5-[4-[[4-fluoro-2-(trifluoromethyl)phenyl]methylamino]pyrimidin-2-yl]pyridine-3-carbonitrile |
| 182 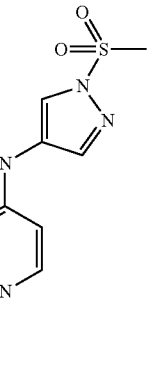 | N-(1-methylsulfonylpyrazol-4-yl)-2-[5-(trifluoromethyl)-3-pyridyl]pyrimidin-4-amine<br>IC50 FAK: B<br>HPLC Retention Time [min]: 3.4<br>LCMS Mass found [M + H]+: 385<br>1H NMR: (400 MHz, DMSO-d6): δ 10.21 (s, 1H), 9.71 (s, 1H), 9.10 (s, 1H), 8.81 (s, 1H), 8.6 (s, 1H), 8.52 (d, J = 4.0 Hz, 1H), 8.18 (s, 1H), 3.51 (s, 3H). |

TABLE 4-continued

| Structure | Chemical Name |
|---|---|
| 183 | N-[2-[[2-[5-(trifluoromethyl)-3-pyridyl]pyrimidin-4-yl]amino]cyclopentyl]methanesulfonamide |
| 184 | N-methyl-1-[[[2-[5-(trifluoromethyl)-3-pyridyl]pyrimidin-4-yl]amino]methyl]cyclopropanecarboxamide |
| 185 | N-[2-[[2-[5-(trifluoromethyl)-3-pyridyl]pyrimidin-4-yl]amino]cyclopentyl]acetamide |

TABLE 5

| Structure | Chemical Name | FAK IC50 | RT [Min] [M + H+] | |
|---|---|---|---|---|
| 186 | (2-Methyl-benzyl)-[2-(5-trifluoromethyl-pyridin-3-yl)-pyrimidin-4-yl]-amine | B | 2.491 345.1 | ¹H NMR (400 MHz, DMSO) δ 9.69-9.64 (d, J = 1.9 Hz, 1H), 9.09-9.04 (dd, J = 2.1, 1.1 Hz, 1H), 8.83-8.76 (s, 1H), 8.27-8.19 (d, J = 5.7 Hz, 1H), 8.12-8.04 (m, 1H), 7.38-7.29 (s, 1H), 7.22-7.11 (m, 3H), 6.65-6.56 (s, 1H), 4.75-4.46 (s, 2H), 2.39-2.35 (s, 3H). |
| 187 | [2-(5-Methoxy-pyridin-3-yl)-pyrimidin-4-yl]-phenethyl-amine | D | 1.756 307.1 | — |
| 188 | Phenethyl-[2-(5-trifluoromethyl-pyridin-3-yl)-pyrimidin-4-yl]-amine | | 1.874 397.1 | ¹H NMR (400 MHz, DMSO, TFA exchange) δ 9.61 (s, 1H), 9.25 (s, 1H), 8.87 (s, 1H), 8.29-8.22 (d, J = 7.2 Hz, 1H), 7.40-7.25 (m, 5H), 6.91-6.86 (d, J = 7.2 Hz, 1H), 3.06-2.95 (m, 2H), 3.99-3.87 (m, 2H). |
| 189 | 6-[(3-Fluoro-pyridin-2-ylmethyl)-amino]-2-(5-trifluoromethyl-pyridin-3-yl)-pyrimidine-4-carboxylic acid (2-acetylamino-ethyl)-amide | B | 2.060 478.1 | — |

TABLE 5-continued

| Structure | Chemical Name | FAK IC50 | RT [Min] [M + H+] | |
|---|---|---|---|---|
| 190 | 6-[(3-Fluoro-pyridin-2-ylmethyl)-amino]-2-(5-trifluoromethyl-pyridin-3-yl)-pyrimidine-4-carboxylic acid carbamoylmethyl-amide | B | 1.996 549.2 | — |
| 191 | [2-(3-Trifluoromethyl-phenyl)-ethyl]-[2-(5-trifluoromethyl-pyridin-3-yl)-pyrimidin-4-yl]-amine | C | 2.648 413.1 | $^1$H NMR (400 MHz, DMSO, TFA exchange) δ 9.60 (s, 1H), 9.27 (s, 1H), 8.87 (s, 1H), 8.29 (d, 1H), 7.66-7.58 (m, 2H), 7.55-7.48 (m, 2H), 6.87 (d, 1H), 3.14-3.07 (m, 2H), 4.01-3.94 (m, 2H). |
| 192 | [2-(4-Fluoro-phenyl)-ethyl]-[2-(5-methoxy-pyridin-3-yl)-pyrimidin-4-yl]-amine | C | 1.788 325.1 | $^1$H NMR (400 MHz, DMSO) δ 9.05 (s, 1H), 8.38 (s, 1H), 8.15 (s, 1H), 8.13-8.08 (m, 1H), 7.62 (s, 1H), 7.35-7.28 (m, 2H), 7.14-7.07 (m, 2H), 6.49-6.41 (d, J = 5.8 Hz, 1H), 3.90 (s, 3H), 3.66-3.60 (m, 2H), 2.93-2.87 (m, 2H). |
| 193 | (2'-Methanesulfonyl-biphenyl-2-ylmethyl)-[2-(5-methoxy-pyridin-3-yl)-pyrimidin-4-yl]-amine | D | 1.721 447.1 | $^1$H NMR (500 MHz, DMSO, TFA exchange) δ 8.87 (s, 1H), 8.76 (d, J = 2.4 Hz, 1H), 8.29 (s, 1H), 8.13 (d, J = 7.0 Hz, 1H), 7.80 (d, J = 7.9 Hz, 1H), 7.91-7.41 (m, 3H), 7.37-7.33 (m, 2H), 7.27-7.24 (m, 2H), 6.70 (d, J = 7.1 Hz, 1H), 4.93 (d, J = 15.1 Hz, 1H), 4.48 (d, J = 15.1 Hz, 1H), 3.99 (s, 3H). |

TABLE 5-continued

| Structure | Chemical Name | FAK IC50 | RT [Min] [M + H+] | ¹H NMR |
|---|---|---|---|---|
| 194 | [2-(5-Methoxy-pyridin-3-yl)-pyrimidin-4-yl]-[2-(3-trifluoromethyl-phenyl)-ethyl]-amine | D | 1.979 375.1 | ¹H NMR (400 MHz, DMSO) δ 9.14 (s, 1H), 8.85 (s, 1H), 8.52-8.49 (m, 1H), 8.25 (d, J = 7.2 Hz, 1H), 7.65-7.58 (m, 3H), 7.54-7.48 (m, 2H), 6.88 (d, J = 7.1 Hz, 1H), 4.06 (s, 3H), 3.98 (t, J = 6.9 Hz, 2H), 3.14-3.09 (m, 2H). |
| 195 | [2-(4-Fluoro-phenyl)-ethyl]-[2-(5-trifluoromethyl-pyridin-3-yl)-pyrimidin-4-yl]-amine | B | 2.449 363.05 | ¹H NMR (400 MHz, DMSO, TFA exchange) δ 9.62 (s, 1H), 9.25 (s, 1H), 8.87 (s, 1H), 8.27 (d, J = 7.2 Hz, 1H), 7.34-7.31 (m, 2H), 7.08-7.03 (m, 2H), 6.88 (d, J = 7.2 Hz, 1H), 3.91-3.89 (m, 2H), 3.01-2.98 (m, 2H). |
| 196 | (2'-Methanesulfonyl-biphenyl-2-ylmethyl)-[2-(5-trifluoromethyl-pyridin-3-yl)-pyrimidin-4-yl]-amine | C | 2.310 485.1 | ¹H NMR (400 MHz, DMSO, TFA exchange) δ 9.43 (s, 1H), 9.23 (s, 1H), 8.75 (s, 1H), 8.21 (d, J = 7.2 Hz, 1H), 7.93 (d, J = 8.0 Hz, 1H), 7.61-7.48 (m, 3H), 7.46-7.41 (m, 2H), 7.35-7.32 (m, 2H), 6.82 (d, J = 7.2 Hz, 1H), 4.92 (d, J = 15.2 Hz, 1H), 4.62 (d, J = 15.0 Hz, 1H), 2.88 (s, 3H). |
| 197 | [2-(1-Methyl-pyrrolidin-2-yl)-ethyl]-[2-(5-trifluoromethyl-pyridin-3-yl)-pyrimidin-4-yl]-amine | D | 1.381 352.1 | ¹H NMR (500 MHz, DMSO, TFA exchange) δ 9.67 (s, 1H), 9.25 (s, 1H), 8.92 (s, 1H), 8.33 (d, J = 7.2 Hz, 1H), 8.11 (s, 1H), 6.92 (d, J = 7.2 Hz, 1H), 3.77 (m, 2H), 3.65 (m, 1H), 3.40 (m, 1H), 3.11 (m, 1H), 2.88 (s, 3H), 2.36 (m, 2H), 1.99 (m, 3H), 1.80 (m, 1H), 0.88 (m, 2H). |

TABLE 5-continued

| Structure | Chemical Name | FAK IC50 | RT [Min] [M + H+] | |
|---|---|---|---|---|
| 198 | [2-(2-Chloro-phenyl)-ethyl]-[2-(5-trifluoromethyl-pyridin-3-yl)-pyrimidin-4-yl]-amine | C | 2.580 379.0 | 1H NMR (500 MHz, DMSO; TFA exchange) δ 9.60 (s, 1H), 9.25 (s, 1H), 8.85 (s, 1H), 8.27 (d, 1H), 7.40-7.34 (m, 2H), 7.26-7.17 (m, 2H), 6.86 (d, 1H), 4.02-3.91 (m, 2H), 3.17-3.09 (t, J = 7.0 Hz, 2H). |
| 199 | 1-{2-[2-(5-Methoxy-pyridin-3-yl)-pyrimidin-4-ylamino]-ethyl}-pyrrolidin-2-one | D | 1.292 314.1 | $^1$H NMR (400 MHz, DMSO) δ 9.26 (s, 1H), 8.85 (d, J = 2.6 Hz, 1H), 8.63 (s, 1H), 8.29 (d, J = 7.2 Hz, 1H), 8.10 (s, 1H), 6.89 (d, J = 7.1 Hz, 1H), 4.09 (s, 3H), 3.85 (m, 2H), 3.54 (m, 2H), 3.48 (m, 2H), 2.23 (m, 2H), 1.91 (m, 2H). |
| 200 | 1-{2-[2-(5-Trifluoromethyl-pyridin-3-yl)-pyrimidin-4-ylamino]-ethyl}-pyrrolidin-2-one | D | 1.684 352.1 | $^1$H NMR (400 MHz, DMSO, TFA exchange) δ 9.71 (s, 1H), 9.23 (s, 1H), 8.95 (s, 1H), 8.26 (d, J = 7.2 Hz, 1H), 8.09 (s, 1H), 6.90 (d, J = 7.2 Hz, 1H), 3.86 (m, 2H), 3.52 (m, 4H), 2.24 (m, 2H), 1.92 (m, 2H). |
| 201 | [2-(2-Methoxy-phenyl)-ethyl]-[2-(5-trifluoromethyl-pyridin-3-yl)-pyrimidin-4-yl]-amine | C | 2.458 375.1 | $^1$H NMR (400 MHz, DMSO) δ 9.66-9.60 (d, J = 2.2 Hz, 1H), 9.28-9.20 (m, 1H), 8.93-8.83 (d, J = 2.2 Hz, 1H), 8.29-8.19 (d, J = 7.8 Hz, 1H), 7.21-7.12 (m, 2H), 6.96-6.89 (d, J = 7.5 Hz, 1H), 6.89-6.81 (m, 2H), 3.84-3.79 (m, 2H), 3.90 (s, 3H), 3.03-2.94 (m, 2H). |

TABLE 5-continued

| Structure | Chemical Name | FAK IC50 | RT [Min] [M + H+] | |
|---|---|---|---|---|
| 202 | [2-(2-Methoxy-phenyl)-ethyl]-[2-(5-methoxy-pyridin-3-yl)-pyrimidin-4-yl]-amine | C | 1.796 357.1 | $^1$H NMR (400 MHz, DMSO) δ 9.18-9.02 (s, 2H), 8.40-8.34 (d, J = 3.0 Hz, 2H), 8.19-8.13 (s, 1H), 8.13-8.08 (s, 2H), 7.70-7.55 (s, 2H), 7.21-7.16 (d, J = 7.4 Hz, 4H), 7.01-6.93 (d, J = 8.1 Hz, 2H), 6.92-6.83 (m, 2H), 6.50-6.36 (d, J = 6.8 Hz, 2H), 3.94-3.87 (s, 6H), 3.87-3.79 (s, 6H). |
| 203 | [2-(2-Chloro-phenyl)-ethyl]-[2-(5-methoxy-pyridin-3-yl)-pyrimidin-4-yl]-amine | C | 1.891 341.1 | $^1$H NMR (400 MHz, DMSO) δ 9.15-9.00 (s, 1H), 8.44-8.35 (d, J = 2.9 Hz, 1H), 8.20-8.13 (s, 1H), 8.13-8.09 (m, 1H), 7.76-7.62 (s, 1H), 7.45-7.39 (m, 1H), 7.39-7.35 (m, 1H), 7.32-7.16 (m, 2H), 6.56-6.38 (d, J = 5.9 Hz, 1H), 3.91 (s, 3H), 3.84-3.58 (m, 2H), 3.12-2.94 (m, 2H). |
| 204 | (4-Fluoro-2-trifluoromethyl-benzyl)-[2-(5-methoxy-pyridin-3-yl)-pyrimidin-4-yl]-amine | A | 2.094 379.05 | — |
| 205 | (2-Fluoro-benzyl)-[2-(2-fluoro-pyridin-3-yl)-pyrimidin-4-yl]-amine | C | 1.644 299.05 | — |

TABLE 5-continued

| | Chemical Name | FAK IC50 | RT [Min] [M + H+] | |
|---|---|---|---|---|
| 206 | (2-Fluoro-benzyl)-[2-(6-fluoro-4-methyl-pyridin-3-yl)-pyrimidin-4-yl]-amine | D | 1.746 313.1 | — |
| 207 | (2-Fluoro-benzyl)-[2-(6-fluoro-pyridin-3-yl)-pyrimidin-4-yl]-amine | D | 1.867 299.1 | — |
| 208 | (3-Fluoro-pyridin-2-ylmethyl)-[2-(5-trifluoromethyl-pyridin-3-yl)-pyrimidin-4-yl]-amine | B | 2.102 350.1 | 1H NMR (500 MHz, DMSO) δ 9.63 (s, 1H), 9.05 (s, 1H), 8.78 (s, 1H), 8.37 (m, 2H), 8.23 (s, 1H), 7.69 (m, 1H), 7.38 (m, 1H), 6.66 (d, J = 6.0 Hz, 1H), 4.80 (s, 2H). |
| 209 | (3,5-Difluoro-pyridin-2-ylmethyl)-[2-(5-trifluoromethyl-pyridin-3-yl)-pyrimidin-4-yl]-amine | A | 2.380 368.05 | 1H NMR (500 MHz, DMSO) δ 9.51 (s, 1H), 9.09 (s, 1H), 8.70 (s, 1H), 8.46 (d, J = 5.1 Hz, 1H), 8.42 (d, J = 2.2 Hz, 1H), 7.87 (m, 3H), 7.42 (d, J = 5.1 Hz, 1H), 4.71 (d, J = 5.7 Hz, 2H). |

TABLE 5-continued
| Structure | Chemical Name | FAK IC50 | RT [Min] [M + H+] | |
|---|---|---|---|---|
| 210 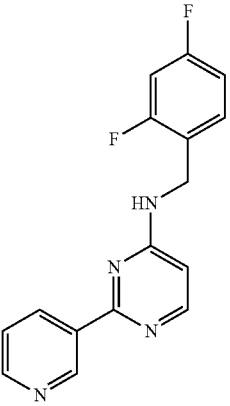 [SMILES: Fc1ccc(CNc2ccnc(-c3cccnc3)n2)c(F)c1] | (2,4-Difluoro-benzyl)-(2-pyridin-3-yl-pyrimidin-4-yl)-amine | B | 1.666 299.05 | — |
| 211 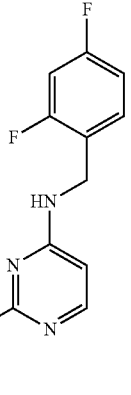 | (2,4-Difluoro-benzyl)-[2-(6-fluoro-4-methyl-pyridin-3-yl)-pyrimidin-4-yl]-amine | D | 1.833 331.1 | — |
| 212 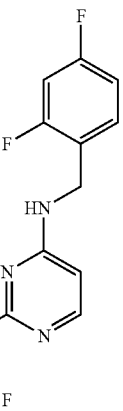 | (2,4-Difluoro-benzyl)-[2-(2-fluoro-pyridin-3-yl)-pyrimidin-4-yl]-amine | C | 1.728 317.05 | — |
| 213 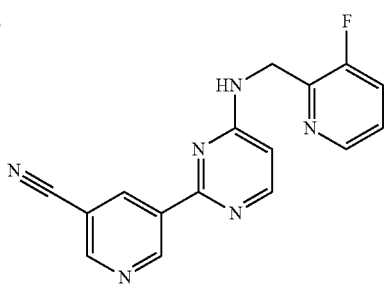 [SMILES: N#Cc1cncc(-c2nccc(NCc3ncccc3F)n2)c1] | 5-{4-[(3-Fluoro-pyridin-2-ylmethyl)-amino]-pyrimidin-2-yl}-nicotinonitrile | C | — | — ¹H NMR (400 MHz, DMSO) δ 9.59 (d, J = 2.0 Hz, 1H), 9.09 (d, J = 2.1 Hz, 1H), 8.89 (t, J = 2.1 Hz, 1H), 8.39 (dt, J = 4.6, 1.5 Hz, 1H), 8.28 (s, 1H), 8.23 (d, J = 5.7 Hz, 1H), 7.71 (m, 1H), 7.40 (m, 1H), 6.66 (d, J = 6.0 Hz, 1H), 4.83 (s, 1H). |

TABLE 5-continued

| Structure | Chemical Name | FAK IC50 | RT [Min] [M + H+] | |
|---|---|---|---|---|
| 214 | (3-Fluoro-pyridin-2-ylmethyl)-[2-(5-methoxy-pyridin-3-yl)-pyrimidin-4-yl]-amine | B | — | — ¹H NMR (400 MHz, DMSO) δ 9.37 (s, 1H), 8.97 (d, J = 1.7 Hz, 1H), 8.54 (d, J = 2.8 Hz, 1H), 8.41 (d, J = 4.7 Hz, 1H), 8.24 (d, J = 5.2 Hz, 1H), 8.20 (m, 1H), 7.75 (m, 1H), 7.43 (m, 1H), 6.84 (d, J = 6.6 Hz, 1H), 4.93 (s, 2H), 3.95 (s, 3H). |
| 215 | 5-[4-(2,4-Difluoro-benzylamino)-5-trifluoromethyl-pyrimidin-2-yl]-nicotinonitrile | D | — | — — |
| 216 | 5-{[2-(5-Methoxy-pyridin-3-yl)-pyrimidin-4-ylamino]-methyl}-1,3-dihydro-benzoimidazol-2-one | D | 1.377 349.1 | — |
| 217 | (2,4-Difluoro-benzyl)-[2-(6-fluoro-pyridin-3-yl)-pyrimidin-4-yl]-amine | D | 1.983 317.1 | — |

| Structure | Chemical Name | FAK IC50 | RT [Min] [M + H+] | |
|---|---|---|---|---|
| 218 | [2-(5-Methoxy-pyridin-3-yl)-pyrimidin-4-yl]-(1H-pyrazol-3-ylmethyl)-amine | C | 1.284 283.1 | — |
| 219 | Pyridin-2-ylmethyl-[2-(5-trifluoromethyl-pyridin-3-yl)-pyrimidin-4-yl]-amine | B | 1.639 332.1 | $^1$H NMR (400 MHz, DMSO) δ 9.60 (s, 1H), 9.05 (s, 1H), 8.70 (s, 1H), 8.54 (d, J = 4.7 Hz, 1H), 8.33 (s, 1H), 8.25 (d, J = 5.3 Hz, 1H), 7.74 (m, 1H), 7.40 (d, J = 7.9 Hz, 1H), 7.26 (m, 1H), 6.67 (s, 1H), 4.74 (s, 2H). |
| 220 | 5-{4-[(Pyridin-2-ylmethyl)-amino]-pyrimidin-2-yl}-nicotinonitrile | C | — | — — |
| 221 | [2-(5-Methoxy-pyridin-3-yl)-pyrimidin-4-yl]-(2-phenyl-thiazol-4-ylmethyl)-amine | D | 1.934 376.1 | — |

TABLE 5-continued

| Structure | Chemical Name | FAK IC50 | RT [Min] [M + H+] | |
|---|---|---|---|---|
| 222 | (2,5-Dimethyl-2H-pyrazol-3-ylmethyl)-[2-(5-methoxy-pyridin-3-yl)-pyrimidin-4-yl]-amine | D | 1.420 311.1 | $^{1}$H NMR (400 MHz, DMSO) δ 9.07 (d, J = 1.4 Hz, 1H), 8.38 (d, J = 2.9 Hz, 1H), 8.22 (d, J = 5.3 Hz, 1H), 8.11 (dd, J = 2.9, 1.7 Hz, 1H), 7.96 (m, 1H), 6.53 (d, J = 5.9 Hz, 1H), 5.99 (s, 1H), 4.65 (s, 2H), 3.91 (s, 3H), 3.74 (s, 3H), 2.07 (s, 3H). |
| 223 | (2,4-Difluoro-benzyl)-[2-(5-methoxy-pyridin-3-yl)-pyrimidin-4-yl]-amine | A | 1.816 329.1 | $^{1}$H NMR (500 MHz, DMSO) δ 9.02 (d, J = 1.6 Hz, 1H), 8.36 (d, J = 2.9 Hz, 1H), 8.21 (d, J = 4.7 Hz, 1H), 8.08 (m, 2H), 7.47 (m, 1H), 7.24 (m, 1H), 7.06 (m, 2H), 6.54 (d, J = 5.9 Hz, 1H), 4.65 (s, 2H), 3.89 (s, 3H). |
| 224 | [2-(5-Methoxy-pyridin-3-yl)-pyrimidin-4-yl]-(2,4,5-trifluoro-benzyl)-amine | B | 1.895 347.1 | $^{1}$H NMR (500 MHz, DMSO) δ 9.02 (d, J = 1.5 Hz, 1H), 8.36 (d, J = 2.9 Hz, 1H), 8.23 (d, J = 5.3 Hz, 1H), 8.08 (m, 2H), 7.52 (m, 2H), 6.56 (d, J = 5.9 Hz, 1H), 4.64 (s, 2H), 3.90 (s, 3H). |
| 225 | 3-{[2-(5-Methoxy-pyridin-3-yl)-pyrimidin-4-ylamino]-methyl}-benzonitrile | C | 1.649 318.1 | — |

TABLE 5-continued

| Structure | Chemical Name | FAK IC50 | RT [Min] [M + H+] | |
|---|---|---|---|---|
| 226 | (2,5-Difluoro-benzyl)-[2-(5-methoxy-pyridin-3-yl)-pyrimidin-4-yl]-amine | B | — | — ¹H NMR (400 MHz, DMSO) δ 9.01 (d, J = 1.6 Hz, 1H), 8.36 (d, J = 2.9 Hz, 1H), 8.23 (d, J = 5.8 Hz, 1H), 8.12 (s, 1H), 8.05 (d, J = 1.7 Hz, 1H), 7.26 (m, 2H), 7.14 (m, 1H), 6.56 (d, J = 5.9 Hz, 1H), 4.67 (s, 2H), 3.89 (s, 3H). |
| 227 | Benzyl-[2-(5-methoxy-pyridin-3-yl)-pyrimidin-4-yl]-amine | B | 1.695 293.1 | — |
| 228 | [2-(5-Methoxy-pyridin-3-yl)-pyrimidin-4-yl]-pyridin-2-ylmethyl-amine | B | 1.239 294.1 | ¹H NMR (400 MHz, DMSO) δ 8.97 (s, 1H), 8.53 (d, J = 4.8 Hz, 1H), 8.34 (d, J = 2.8 Hz, 1H), 8.20 (m, 2H), 8.01 (s, 1H), 7.74 (m, 1H), 7.39 (d, J = 7.8 Hz, 1H), 7.26 (m, 2H), 6.60 (s, 1H), 4.73 (s, 2H), 3.87 (s, 3H). |
| 229 | [2-(5-Methoxy-pyridin-3-yl)-pyrimidin-4-yl]-pyridin-3-ylmethyl-amine | C | 1.111 294.1 | — |

TABLE 5-continued

| Structure | Chemical Name | FAK IC50 | RT [Min] [M + H+] | |
|---|---|---|---|---|
| 230 | [2-(5-Methoxy-pyridin-3-yl)-pyrimidin-4-yl]-pyridin-4-ylmethyl-amine | D | 1.066 294.1 | ¹H NMR (500 MHz, DMSO) δ 9.03 (s, 1H), 8.92 (d, J = 5.3 Hz, 2H), 8.75 (d, J = 2.1 Hz, 1H), 8.43 (d, J = 6.4 Hz, 1H), 8.39 (s, 1H), 8.12 (m, 3H), 5.19 (s, 2H), 4.02 (s, 3H). LCMS-Analysis: Method A Method: A-0.1% TFA in H2O, B-0.1% TFA in ACN: Flow-2.0 mL/min. Column: XBridge C8 (50 × 4.6 mm, 3.5 mm), +ve mode HPLC: Method A Method: A-0.1% TFA in H2O, B-0.1% TFA in ACN: Flow-2.0 mL/min. Column: XBridge C8 (50 × 4.6 mm, 3.5 mm) |
| 231 | (2,4-Difluoro-benzyl)-(5'-trifluoromethyl-[2,3']bipyridinyl-6-yl)-amine | A | 4.57 366.18 | 1H NMR: (400 MHz, DMSO-d6): δ 9.63 (s, 1H), 9.02 (s, 1H), 8.60 (s, 1H), 7.54-7.40 (m, 3H), 7.35 (d, J = 4.0 Hz, 1H), 7.21-7.14 (m, 1H), 7.02-6.87 (m, 2H), 6.62 (d, J = 8.0 Hz, 1H), 4.62 (d, J = 8.0 Hz, 1H). LCMS: (Method A) 366.2 (M + H), RT. 4.73 min, 94.9% (Max), 94.2% (254 nm). HPLC: (Method A) RT 4.57 min, % (Max), 95.0% (254 nm), 94.6% (254 nm) |
| 232 | 6-(2,4-Difluoro-benzylamino)-2-(5-trifluoromethyl-pyridin-3-yl)-pyrimidine-4-carboxylic acid (2-methoxy-pyridin-4-yl)-amide | C | 4.71 517 | 1H NMR: (400 MHz, DMSO-d6): δ 10.8 (s, 1H), 10.0 (s, 1H), 9.12-9.07 (m, 2H), 8.7 (t, J = 4.0 Hz, 1H), 8.1 (d, J = 4.0 Hz, 1 H), 7.55-7.44 (m, 3H), 7.29-7.21 (m, 2H), 7.07-7.03 (m, 1H), 4.7 (d, J = 4.0 Hz, 2H). LCMS: (Method A) 517.0 (M + H), RT. 4.71 min, 98.3% (Max), 99.0% (254 nm) HPLC: (Method A) RT 4.71 min, 97.4% (Max), 98.7% (254 nm). |

TABLE 5-continued

| Structure | Chemical Name | FAK IC50 | RT [Min] [M + H+] | |
|---|---|---|---|---|
| 233 | 6-(2,4-Difluoro-benzylamino)-2-(5-trifluoromethyl-pyridin-3-yl)-pyrimidine-4-carboxylic acid (2-methoxy-pyridin-3-yl)-amide | B | 5.97 517 | 1H NMR: (400 MHz, DMSO-d6): δ 10.6 (s, 1H), 9.8 (s, 1H), 9.2 (s, 1H), 8.9 (s, 1H), 8.8 (t, J = 4.0 Hz, 1H), 8.5 (d, J = 4.0 Hz, 1H), 7.98-7.96 (m, 1H), 7.56-7.50 (m, 1H), 7.28-7.23 (m, 2H), 7.09-7.04 (m, 2H), 4.8 (d, J = 4.0 Hz, 2H), 4.0 (s, 3H). LCMS: (Method A) 517.0 (M + H), RT. 6.00 min, 90.3% (Max), 88.1% (254 nm) HPLC: (Method A) RT 5.97 min, 89.0% (Max), 91.3% (254 nm). |
| 234 | N-Methyl-2-{[2-(5-trifluoromethyl-pyridin-3-yl)-pyrimidin-4-ylamino]-methyl}-benzamide | C | 2.82 388 | 1H NMR: (400 MHz, DMSO-d6): δ 9.61 (d, J = 1.4 Hz, 1H), 9.10 (s, 1H), 8.8 (s, 1H), 8.30-8.06 (m, 3H), 7.51 (d, J = 8.0 Hz, 1H), 7.40-7.36 (m, 2H), 7.31-7.27 (m, 1H), 6.62 (d, J = 4.0 Hz, 1H), 4.81 (s, 2H), 2.81 (s, 3H). LCMS: (Method A) 388.0 (M + H), RT. 2.86 min, 98.7% (Max), 98.6% (254 nm). HPLC: (Method A) RT 2.82 min, % (Max), 99.3% (254 nm), 98.9% (254 nm) |
| 235 | 2-[2-(5-Trifluoromethyl-pyridin-3-yl)-pyrimidin-4-yl]-2,3-dihydro-isoindol-1-one | D | 4.95 357 | 1H NMR: (400 MHz, DMSO-d6): δ 9.85 (d, J = 1.7 Hz, 1H), 9.18 (d, J = 1.3 Hz, 1H), 8.96 (s, 1H), 8.92 (d, J = 5.8 Hz, 1H), 8.51 (d, J = 5.8 Hz, 1H), 7.88 (d, J = 7.6 Hz, 1H), 7.81-7.75 (m, 2H), 7.61-7.57 (m, 1H), 5.31 (s, 2H). LCMS: (Method A) 357.2 (M + H), RT. 5.01 min, 99.3% (Max), 99.6% (254 nm). HPLC: (Method A) RT 4.95 min, 98.4 % (Max), 99.4% (254 nm). |

TABLE 5-continued

| Structure | Chemical Name | FAK IC50 | RT [Min] [M + H+] | |
|---|---|---|---|---|
| 236 | N-{3-[6-(2,4-Difluoro-benzylamino)-9H-purin-2-yl]-phenyl}-methanesulfonamide | D | 3.589 431 | 1H NMR: (400 MHz, DMSO-d6): δ 9.8 (s, 1H), 8.15-8.12 (m, 2H), 8.10-8.09 (m, 1H), 8.07-8.05 (m, 1H), 7.54-7.52 (m, 1H), 7.42-7.40 (m, 2H), 7.30-7.21 (m, 2H), 7.04-7.00 (m, 1H), 4.9 (s, 2H), 3.0 (s, 3H). LCMS: (Method A) 403.3 (M + H), RT. 3.48 min, 99.3% (Max), 99.3% (254 nm). HPLC: (Method A) RT 4.39 min, 99.1% (Max), 98.6% (254 nm) |
| 237 | (2,4-Difluoro-benzyl)-[2-(5-trifluoromethyl-pyridin-3-yl)-9H-purin-6-yl]-amine | B | 4.39 407.1 | 1H NMR: (400 MHz, DMSO-d6): δ 9.7 (s, 1H), 9.0 (s, 1H), 8.8 (s, 1H), 8.70-8.68 (m, 1H), 8.42-8.30 (m, 1H), 7.54-7.48 (m, 1H), 7.23-7.17 (m, 1H), 7.03-6.98 (m, 1H), 4.8 (s, 2H), . LCMS: (Method A) 332.3 (M + H), RT. 4.31 min, 99.3% (Max), 99.3% (254 nm). HPLC: (Method A) RT 4.39 min, 99.1% (Max), 98.6% (254 nm). |
| 238 | Pyridin-3-ylmethyl-[2-(5-trifluoromethyl-pyridin-3-yl)-pyrimidin-4-yl]-amine | B | 1.96 332.3 | 1H NMR: (400 MHz, DMSO-d6): δ 9.80 (s, 1H), 9.06 (s, 1H), 8.76 (s, 1H), 8.63 (d, J = 1.6 Hz, 1H), 8.45-8.44 (m, 1H), 8.30-8.24 (m, 2H), 7.37-7.33 (m, 1H), 6.60 (d, J = 5.9 Hz, 1H), 4.68 (s, 2H). LCMS: (Method A) 332.3 (M + H), RT. 1.96 min, 97.0% (Max), 98.9% (254 nm). HPLC: (Method A) RT 1.96 min, 99.4% (Max), 99.1% (254 nm). |

TABLE 5-continued

| Structure | Chemical Name | FAK IC50 | RT [Min] [M + H+] | |
|---|---|---|---|---|
| 239 | (1H-Pyrazol-4-yl)-[2-(5-trifluoromethyl-pyridin-3-yl)-pyrimidin-4-yl]-amine | C | 2.28 307 | 1H NMR: 400 MHz, DMSO-d6: δ 11.1 (s, 1H), 9.72 (d, J = 4.0 Hz, 1H), 9.21 (s, 1H), 8.90 (s, 1H), 8.01 (s, 2H), 8.41 (d, J = 4.0 Hz, 2H), 6.9 (s, 1H). LCMS: (Method A) 307.0 (M + H), RT. 2.32 min, 96.5% (Max), 96.4% (254 nm). HPLC: (Method A) RT 2.28 min, 96.6% (Max), 96.8% (254 nm). |
| 240 | (2,4-Difluoro-benzyl)-[2-(3-trifluoromethyl-phenyl)-pyrimidin-4-yl]-amine | D | 4.22 366 | 1H NMR: (400 MHz, DMSO-d6): δ 8.55 (t, J = 4.0 Hz, 2H), 8.21 (d, J = 4.6 Hz, 1H), 8.14 (d, J = 5.1 Hz, 1H), 7.82 (d, J = 7.8 Hz, 1H), 7.70 (t, J = 7.7 Hz, 1H), 7.50-7.44 (m, 1H), 7.25-7.19 (m, 1H), 7.06-7.01 (m, 1H), 6.54 (d, J = 5.8 Hz, 1H), 4.63 (s, 2H). LCMS: (Method A) 366.0 (M + H), RT. 4.33 min, 99.4% (Max), 99.2% (254 nm). HPLC: (Method A) RT 4.22 min, 99.8% (Max), 99.7% (254 nm). |
| 241 | N-{3-[4-(2,4-Difluoro-benzylamino)-pyrimidin-2-yl]-phenyl}-methanesulfonamide | D | 3.23 391 | 1H NMR: (400 MHz, DMSO-d6): δ 9.9 (s, 1H), 8.2 (s, 1H), 8.2 (d, J = 8.0 Hz, 1H), 8.04-7.96 (m, 2H), 7.52-7.20 (m, 4H), 7.05-7.01 (m, 1H), 6.5 (d, J = 8.0 Hz, 1H), 4.6 (s, 2H), 3.0 (s, 3H). LCMS: (Method A) 391.2 (M + H), RT. 3.28 min, 97.8% (Max), 98.8% (254 nm). HPLC: (Method A) RT 3.23 min, 98.3% (Max), 98.6% (254 nm) |

TABLE 5-continued

| Structure | Chemical Name | FAK IC50 | RT [Min] [M + H+] | |
|---|---|---|---|---|
| 242 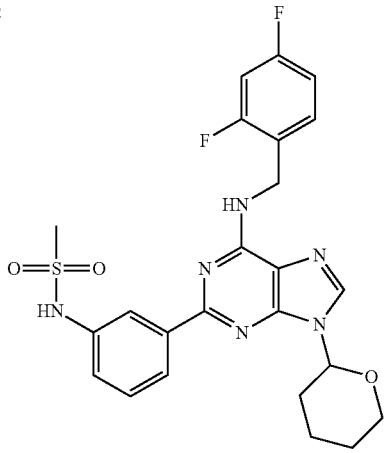 | N-{3-[6-(2,4-Difluoro-benzylamino)-9-(tetrahydro-pyran-2-yl)-9H-purin-2-yl]-phenyl}-methanesulfonamide | D | 4.62 515.2 | 1H NMR: (400 MHz, DMSO-d6): δ 8.53-8.52 (m, 1H), 8.3 (s, 1H), 8.1 (d, J = 8.0 Hz, 1H), 7.51-7.27 (m, 3H), 7.23-7.17 (m, 1H), 7.01-6.98 (m, 1H), 5.7 (t, J = 8.0 Hz, 1H), 4.8 (s, 2H), 4.0 (d, J = 8.0 Hz, 1H), 3.7 (d, J = 4.0 Hz, 1H), 3.3 (s, 3H), 2.50-2.48 (m, 1H), 2.0 (d, J = 8.0 Hz, 2H), 1.61-1.59 (m, 3H). LCMS: (Method A) 515.3 (M + H), RT. 3.48 min, 85.3% (Max), 95.6% (254 nm). HPLC: (Method A) RT 4.62 min, 92.9% (Max), 96.7% (254 nm) |
| 243 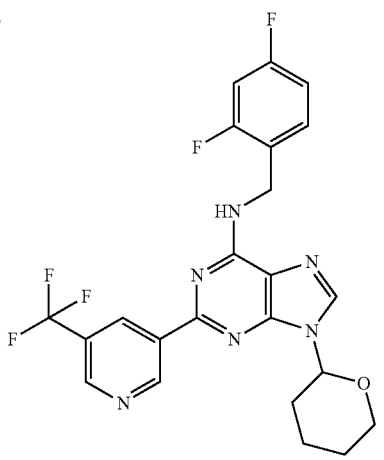 [SMILES: Fc1ccc(CNc2nc(-c3cncc(C(F)(F)F)c3)nc3c2ncn3C2CCCCO2)c(F)c1] | (2,4-Difluoro-benzyl)-[9-(tetrahydro-pyran-2-yl)-2-(5-trifluoromethyl-pyridin-3-yl)-9H-purin-6-yl]-amine | B | 5.6 491 | 1H NMR: (400 MHz, DMSO-d6): δ 9.8 (s, 1H), 9.0 (s, 1H), 8.81-8.75 (m, 2H), 8.5 (s, 1H), 7.52-7.46 (m, 1H), 7.20-7.16 (m, 1H), 7.02-6.97 (m, 1H), 5.8 (d, J = 12.0 Hz, 1H), 4.8 (s, 2H), 4.0 (t, J = 4.0 Hz, 1H), 3.78-3.71 (m, 1H), 2.32-2.29 (m, 1H), 2.00-1.97 (m, 2H), 1.80-1.76 (m, 1H), 1.62-1.59 (m, 2H). LCMS: (Method A) 491.2 (M + H), RT. 5.50 min, 94.2% (Max), 97.8% (254 nm). HPLC: (Method A) RT 5.60 min, 90.6% (Max), 96.5% (254 nm) |
| 244 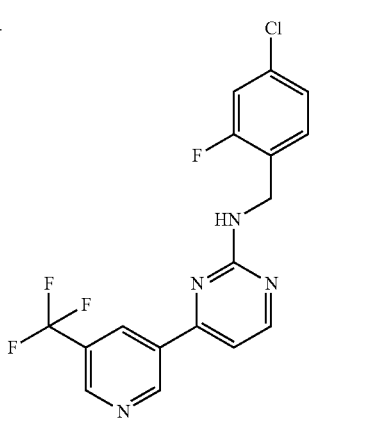 | (4-Chloro-2-fluoro-benzyl)-[4-(5-trifluoromethyl-pyridin-3-yl)-pyrimidin-2-yl]-amine | B | 4.77 383 | 1H NMR: 400 MHz, DMSO-d6: δ 9.61-9.51 (m, 1H), 9.12-9.09 (m, 1H), 8.70-8.68 (m, 1H), 8.50 (d, J = 4.0 Hz, 1H), 8.10-8.06 (m, 1H), 7.44-7.35 (m, 2H), 7.23-7.21 (m, 1H), 4.60 (d, J = 4.0 Hz, 2H). LCMS: (Method A) 383.0 (M + H), RT. 4.80 min, 98.1% (Max), 99.2% (254 nm). HPLC: (Method A) RT 4.77 min, 97.7% (Max), 98.15% (254 nm). |

TABLE 5-continued

| Structure | Chemical Name | FAK IC50 | RT [Min] [M + H+] | 1H NMR |
|---|---|---|---|---|
| 245 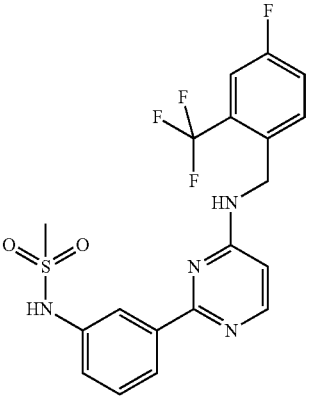 [SMILES: CS(=O)(=O)Nc1cccc(-c2nccc(NCc3ccc(F)cc3C(F)(F)F)n2)c1] | N-{3-[4-(4-Fluoro-2-trifluoromethyl-benzylamino)-pyrimidin-2-yl]-phenyl}-methanesulfonamide | D | 3.68 441 | 1H NMR: (400 MHz, DMSO-d6): δ 9.79 (s, 1H), 9.49 (s, 1H), 8.21 (t, J = 8.92 Hz, 1H), 8.04 (t, J = 5.6 Hz, 1H), 7.94 (d, J = 7.0 Hz, 2H), 7.65-7.62 (m, 1H), 7.53-7.48 (m, 1H), 7.37 (t, J = 7.8 Hz, 1H), 7.27 (d, J = 8.6 Hz, 1H), 6.55 (s, 1H), 4.81 (s, 2H), 2.95 (s, 3H). LCMS: (Method A) 441.0 (M + H), RT. 2.45 min, 97.4% (Max), 98.5% (254 nm). HPLC: (Method A) RT 3.68 min, 98.1% (Max), 99.0% (254 nm). |
| 246 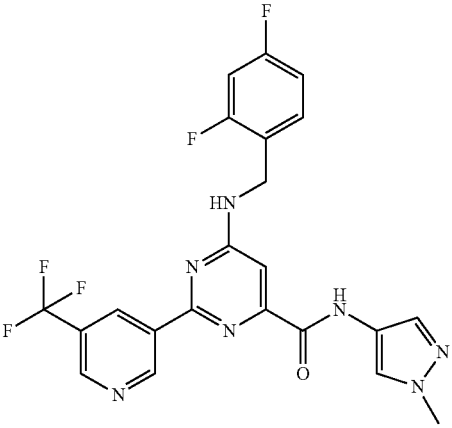 [SMILES: Cn1cc(NC(=O)c2cc(NCc3ccc(F)cc3F)nc(-c3cncc(C(F)(F)F)c3)n2)cn1] | 6-(2,4-Difluoro-benzylamino)-2-(5-trifluoromethyl-pyridin-3-yl)-pyrimidine-4-carboxylic acid (1-methyl-1H-pyrazol-4-yl)-amide | B | 4.94 490 | 1H NMR: (400 MHz, DMSO-d6): δ 10.78 (s, 1H), 10.06 (s, 1H), 9.12 (s, 1H), 9.06 (s, 1H), 8.66 (t, J = 5.9 Hz, 1H), 8.13 (s, 1H), 7.74 (s, 1H), 7.55-7.48 (m, 1H), 7.24 (t, J = 8.1 Hz, 1H), 7.05 (t, J = 8.5 Hz, 1H), 4.73 (d, J = 5.6 Hz, 2H), 3.84 (s, 3H). LCMS: (Method A) 490.0 (M + H), RT. 4.95 min, 96.4% (Max), 94.1% (254 nm) HPLC: (Method A) RT 4.94 min, 95.3% (Max), 93.7% (254 nm). |
| 247 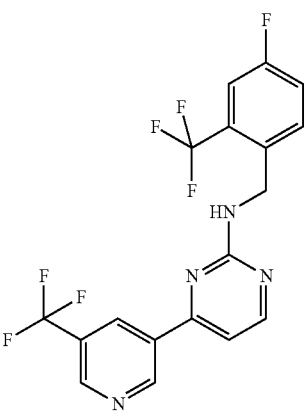 [SMILES: Fc1ccc(CNc2nccc(-c3cncc(C(F)(F)F)c3)n2)c(C(F)(F)F)c1] | (4-Fluoro-2-trifluoromethyl-benzyl)-[4-(5-trifluoromethyl-pyridin-3-yl)-pyrimidin-2-yl]-amine | A | 5.03 417 | 1H NMR: 400 MHz, DMSO-d6: δ 9.45-9.43 (m, 1H), 9.10-9.05 (m, 1H), 8.74-8.49 (m, 2H), 8.20-8.18 (m, 1H), 7.62-7.59 (m, 2H), 7.49-7.46 (m, 2H), 4.71 (d, J = 4.0 Hz, 2H). LCMS: (Method A) 418.0 (M + H), RT. 5.05 min, 98.8% (Max), 99.5% (254 nm). HPLC: (Method A) RT 5.03 min, 99.3% (Max), 99.6% (254 nm). |

TABLE 5-continued

| Structure | Chemical Name | FAK IC50 | RT [Min] [M + H+] | |
|---|---|---|---|---|
| 248 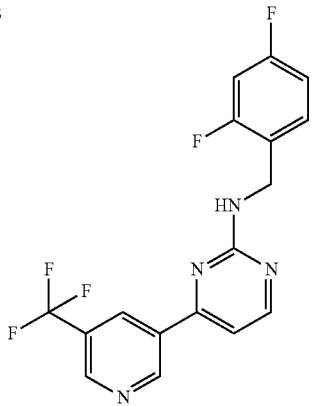 | (2,4-Difluoro-benzyl)-[4-(5-trifluoromethyl-pyridin-3-yl)-pyrimidin-2-yl]-amine | A | 4.46 | 367 |

1H NMR: 400 MHz, DMSO-d6: δ 9.51 (s, 1H), 9.11 (s, 1H), 8.73-8.70 (m, 1H), 8.50 (d, J = 4.0 Hz, 1H), 8.0 (s, 1H), 7.42 (d, J = 4.0 Hz, 2H), 7.20-7.15 (m, 1H), 7.03-6.98 (m, 1H), 4.63 (d, J = 4.0 Hz, 2H).
LCMS: (Method A) 383.0 (M + H), RT. 4.59 min, 96.3% (Max), 99.2% (254 nm).
HPLC: (Method A) RT 4.46 min, 99.8% (Max), 99.6% (254 nm).

| 249 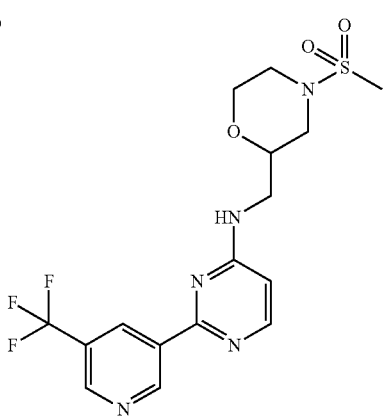 | (4-Methanesulfonyl-morpholin-2-ylmethyl)-[2-(5-trifluoromethyl-pyridin-3-yl)-pyrimidin-4-yl]-amine | C | 2.72 | 418 |

1H NMR: (400 MHz, DMSO-d6): δ 9.70 (s, 1H), 9.08 (d, J = 1.4 Hz, 1H), 8.82 (d, J = 1.8 Hz, 1H), 8.21 (d, J = 5.0 Hz, 1H), 7.83 (s, 1H), 6.59 (d, J = 5.2 Hz, 1H), 3.89-3.95 (m, 1H), 3.69 (s, 1H), 3.57-3.52 (m, 3H), 3.31 (s, 1H), 2.88-2.80 (m, 3H), 2.68-2.62 (m, 1H), 2.50-2.48 (m, 1H).
LCMS: (Method A) 418.0 (M + H), RT. 2.77 min, 95.4% (Max), 95.9% (254 nm).
HPLC: (Method A) RT 2.72 min, 95.8% (Max), 95.0% (254 nm)

| 250 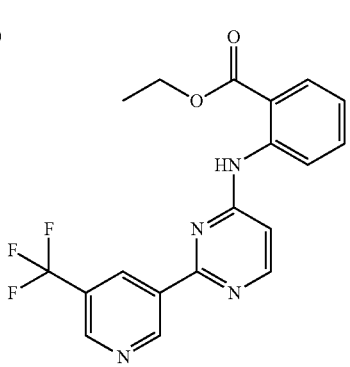 | 2-[2-(5-Trifluoromethyl-pyridin-3-yl)-pyrimidin-4-ylamino]-benzoic acid ethyl ester | D | 5 | 389 |

1H NMR: (400 MHz, DMSO-d6): δ 9.58 (s, 1H), 9.60 (d, J = 1.7 Hz, 1H), 9.09 (d, J = 1.4 Hz, 1H), 8.77 (s, 1H), 8.49 (d, J = 5.8 Hz, 1H), 7.91-7.85 (m, 1H), 7.83 (s, 1H), 7.67-7.63 (m, 1H), 7.29-7.25 (m, 1H), 6.90 (d, J = 5.8 Hz, 1H), 4.06-4.00 (q, J = 7.0 Hz, 2H), 1.01 (t, J = 7.0 Hz, 3H).
LCMS: (Method A) 389.0 (M + H), RT. 4.96 min, 95.1% (Max), 93.0% (254 nm).
HPLC: (Method A) RT 5.0 min, 96.3% (Max), 93.3% (254 nm).

TABLE 5-continued

| Structure | Chemical Name | FAK IC50 | RT [Min] [M + H+] | |
|---|---|---|---|---|
| 251 | N-Methyl-N-(3-{[4-(5-trifluoromethyl-pyridin-3-yl)-pyrimidin-2-ylamino]-methyl}-pyridin-2-yl)-methanesulfonamide | C | 3.44 439 | 1H NMR: (400 MHz, DMSO-d6): δ 9.06 (s, 1H), 8.48-8.55 (m, 1H), 8.40 (t, J = 1.8 Hz, 1H), 8.00 (d, J = 4.8 Hz, 1H), 7.81 (d, J = 7.5 Hz, 1H), 7.44 (d, J = 5.1 Hz, 1H), 7.43-7.37 (m, 1H), 4.72 (s, 2H), 3.31-3.30 (m, 3H), 3.12 (s, 3H). LCMS: (Method A) 439.0 (M + H), RT. 3.45 min, 96.1% (Max), 99.2% (254 nm). HPLC: (Method A) RT 3.44 min, 93.7% (Max), 96.4% (254 nm). |
| 252 | (4-Fluoro-2-trifluoromethyl-benzyl)-[6-(5-trifluoromethyl-pyridin-3-yl)-pyrimidin-4-yl]-amine | C | 4.17 417 | 1H NMR: (400 MHz, DMSO-d6): δ 9.58 (s, 1H), 9.09 (d, J = 1.2 Hz, 1H), 8.67 (s, 1H), 8.58 (d, J = 4.8 Hz, 1H), 8.14 (t, J = 5.9 Hz, 1H), 7.66-7.60 (m, 1H), 7.57-7.49 (m, 2H), 7.29 (s, 1H), 4.76 (d, J = 4.7 Hz, 2H). LCMS: (Method A) 417.0 (M + H), RT. 4.16 min, 96.6% (Max), 99.2% (254 nm). HPLC: (Method A) RT 4.17 min, 99.2% (Max), 99.1% (254 nm). |
| 253 | (4-Chloro-2-fluoro-benzyl)-[6-(5-trifluoromethyl-pyridin-3-yl)-pyrimidin-4-yl]-amine | C | 3.9 383 | 1H NMR: (400 MHz, DMSO-d6): δ 9.58 (s, 1H), 9.08 (d, J = 1.2 Hz, 1H), 8.67 (s, 1H), 8.58 (s, 1H), 8.11 (s, 1H), 7.45-7.37 (m, 2H), 7.27-7.25 (m, 2H), 4.62 (d, J = 5.9 Hz, 2H). LCMS: (Method A) 383.0 (M + H), RT. 3.89 min, 96.7% (Max), 95.2% (254 nm). HPLC: (Method A) RT 3.90 min, 96.0% (Max), 95.5% (254 nm). |

TABLE 5-continued

| Structure | Chemical Name | FAK IC50 | RT [Min] [M + H+] | |
|---|---|---|---|---|
| 254 | (2,4-Difluoro-benzyl)-[6-(5-trifluoromethyl-pyridin-3-yl)-pyrimidin-4-yl]-amine | D | 3.56 367 | 1H NMR: (400 MHz, DMSO-d6): δ 9.43 (s, 1H), 9.08 (d, J = 1.6 Hz, 1H), 8.62 (d, J = 1.7 Hz, 1H), 8.09 (s, 1H), 7.46-7.40 (m, 1H), 7.27-7.21 (m, 2H), 7.08-7.03 (m, 1H), 4.61 (s, 2H). LCMS: (Method A) 367.0 (M + H), RT. 3.57 min, 97.1% (Max), 98.3% (254 nm). HPLC: (Method A) RT 3.56 min, 99.3% (Max), 98.7% (254 nm). |
| 255 | N,N-Dimethyl-2-[2-(5-trifluoromethyl-pyridin-3-yl)-pyrimidin-4-ylamino]-benzamide | D | 3.23 388 | 1H NMR: (400 MHz, DMSO-d6): δ 9.60 (s, 1H), 9.43 (s, 1H), 9.07 (d, J = 1.4 Hz, 1H), 8.79 (s, 1H), 8.42 (d, J = 5.8 Hz, 1H), 7.71 (d, J = 7.9 Hz, 1H), 7.51-7.47 (m, 1H), 7.39-7.36 (m, 1H), 7.31-7.27 (m, 1H), 6.79 (d, J = 5.9 Hz, 1H), 2.85 (s, 3H), 2.74 (s, 3H). LCMS: (Method A) 388.0 (M + H), RT. 3.30 min, 99.2% (Max), 99.6% (254 nm). HPLC: (Method A) RT 3.23 min, 96.3% (Max), 95.1% (254 nm). |
| 256 | N-Methyl-2-[2-(5-trifluoromethyl-pyridin-3-yl)-pyrimidin-4-ylamino]-benzamide | D | 3.35 374 | 1H NMR: (400 MHz, DMSO-d6): δ 10.90 (s, 1H), 9.67 (d, J = 1.7 Hz, 1H), 9.11 (d, J = 1.4 Hz, 1H), 8.84 (t, J = 1.7 Hz, 1H), 8.62 (d, J = 4.4 Hz, 1H), 8.49 (d, J = 5.8 Hz, 1H), 8.32 (d, J = 7.7 Hz, 1H), 7.71-7.69 (m, 1H), 7.59-7.54 (m, 1H), 7.20-7.16 (m, 1H), 2.75 (d, J = 4.5 Hz, 3H). LCMS: (Method A) 374.0 (M + H), RT. 3.39 min, 98.2% (Max), 99.1% (254 nm). HPLC: (Method A) RT 3.35 min, 98.1% (Max), 98.1% (254 nm). |

TABLE 5-continued

| Structure | Chemical Name | FAK IC50 | RT [Min] [M + H+] | |
|---|---|---|---|---|
| 257 | (2,4-Difluoro-benzyl)-[6-(1-methyl-1H-pyrazol-4-yl)-2-(5-trifluoromethyl-pyridin-3-yl)-pyrimidin-4-yl]-amine | B | 4.71 447 | 1H NMR: (400 MHz, DMSO-d6): δ 9.80 (s, 1H), 9.11 (s, 1H), 8.94 (s, 1H), 8.42 (s, 1H), 8.13-8.05 (m, 2H), 7.51 (dd, J = 4.0, 8.0 Hz, 1H), 7.24 (t, J = 8.0 Hz, 1H), 7.05-7.01 (m, 1H), 6.82 (s, 1H), 4.72 (s, 2H), 3.93 (s, 3H). LCMS: (Method A) 447.12 (M + H), RT. 4.64 min, 98.6% (Max), 99.5% (254 nm). HPLC: (Method A) RT 4.71 min, 98.7% (Max), 99.5% (254 nm). |
| 258 | [2,6-Bis-(1-methyl-1H-pyrazol-4-yl)-pyrimidin-4-yl]-(2,4-difluoro-benzyl)-amine | C | 3.267 382 | 1H NMR: (400 MHz, DMSO-d6): δ 8.2 (s, 1H), 8.2 (s, 1H), 7.9 (d, J = 1.6 Hz, 2H), 7.6 (s, 1H), 7.52-7.48 (m, 1H), 7.24-7.19 (m, 1H), 7.06-7.01 (m, 1H), 6.5 (s, 1H), 4.6 (d, J = 4.0 Hz, 2H), 3.9 (s, 6H). LCMS: (Method A) 382.0 (M + H), RT. 3.18 min, 96.2% (Max), 94.7% (254 nm). HPLC: (Method A) RT 3.26 min, 97.2% (Max), 95.5% (254 nm). |
| 259 | [6-(2,4-Difluoro-benzylamino)-2-(5-trifluoromethyl-pyridin-3-yl)-pyrimidin-4-yl]-(4-methyl-piperazin-1-yl)-methanone | B | 4.088 493.3 | 1H NMR: (400 MHz, DMSO-d6): δ 9.63 (d, J = 4.0 Hz, 1H), 9.10 (d, J = 4.0 Hz, 1H), 8.74 (s, 1H), 8.45 (d, J = 4.0 Hz, 1H), 7.50 (t, J = 8.0 Hz, 1H), 7.20 (t, J = 8.0 Hz, 1H), 7.07-7.03 (m, 1H), 6.6 (s, 1H), 4.71 (d, J = 8.0 Hz, 2H), 3.60-3.58 (m, 2H), 3.44-3.42 (m, 2H), 2.38-2.30 (m, 4H), 2.22 (s, 3H), . LCMS: (Method A) 493.0 (M + H), RT. 4.00 min, 93.2% (Max), 97.4% (254 nm) HPLC: (Method A) RT 4.09 min, 94.0 % (Max), 97.4% (254 nm). |

TABLE 5-continued

| Structure | Chemical Name | FAK IC50 | RT [Min] [M + H+] | |
|---|---|---|---|---|
| 260 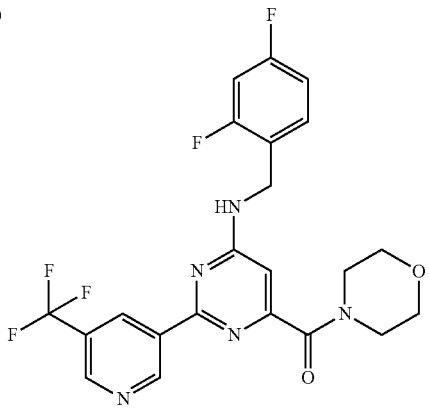 | [6-(2,4-Difluoro-benzylamino)-2-(5-trifluoromethyl-pyridin-3-yl)-pyrimidin-4-yl]-morpholin-4-yl-methanone | A | 4.783 480.3 | 1H NMR: (400 MHz, DMSO-d6): δ 9.62 (d, J = 4.0 Hz, 1H), 9.11 (d, J = 4.0 Hz, 1H), 8.73 (s, 1H), 8.54 (t, J = 8.0 Hz, 1H), 7.54-7.48 (m, 1H), 7.2 (t, J = 8.0 Hz, 1H), 7.06 (t, J = 4.0 Hz, 1H), 4.72 (d, J = 8.0 Hz, 2H), 3.61 (t, J = 4.0 Hz, 8H). LCMS: (Method A) 480.0 (M + H), RT. 4.70 min, 88.7% (Max), 92.3% (254 nm) HPLC: (Method A) RT 4.78 min, 86.2% (Max), 92.2% (254 nm). |
| 261 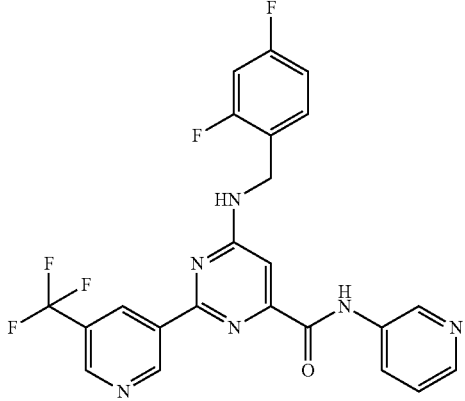 [SMILES: O=C(Nc1cccnc1)c1cc(NCc2ccc(F)cc2F)nc(-c2cncc(C(F)(F)F)c2)n1] | 6-(2,4-Difluoro-benzylamino)-2-(5-trifluoromethyl-pyridin-3-yl)-pyrimidine-4-carboxylic acid pyridin-3-ylamide | B | 4.483 487 | 1H NMR: (400 MHz, DMSO-d6): δ 10.81 (s, 1H), 10.10 (s, 1H), 9.12-9.01 (m, 3H), 8.72 (t, J = 4.0 Hz, 1H), 8.41 (dd, J = 4.0, 8.0 Hz, 1H), 8.20 (dd, J = 8.0 Hz, 1H), 7.55-7.43 (m, 2H), 7.30-7.21 (m, 2H), 7.07-7.03 (m, 1 H), 4.72 (dd, J = 4.0 Hz, 2H). LCMS: (Method A) 487.0 (M + H), RT. 4.37 min, 98.2% (Max), 97.0% (254 nm) HPLC: (Method A) RT 4.48 min, 97.4% (Max), 97.3% (254 nm). |
| 262 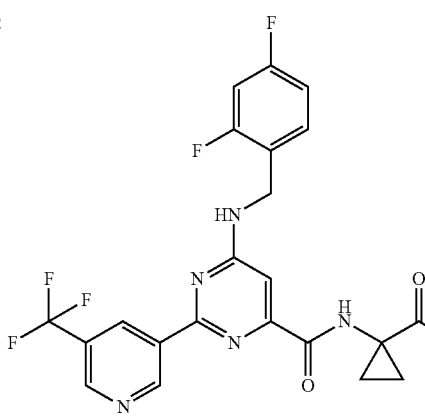 | 6-(2,4-Difluoro-benzylamino)-2-(5-trifluoromethyl-pyridin-3-yl)-pyrimidine-4-carboxylic acid (1-methylcarbamoyl-cyclopropyl)-amide | B | 4.717 507 | 1H NMR: (400 MHz, DMSO-d6): δ 10.01 (s, 1H), 9.46 (s, 1H), 9.08 (s, 2H), 8.59 (d, J = 5.24 Hz, 1H), 7.77 (d, J = 4.56 Hz, 1H), 7.50-7.44 (m, 1H), 7.25-7.21 (m, 2H), 7.04 (t, J = 4.76 Hz, 1H), 4.71 (d, J = 5.40 Hz, 2H), 2.49 (t, J = 1.76 Hz, 3H), 1.20 (s, 2H), 1.04-1.01 (m, 2H). LCMS: (Method A) 507.0 (M + H), RT. 4.72 min, 97.6% (Max), 97.2% (254 nm) HPLC: (Method A) RT 4.72 min, 97.8% (Max), 97.0% (254 nm). |

TABLE 5-continued

| Structure | Chemical Name | FAK IC50 | RT [Min] [M + H+] | |
|---|---|---|---|---|
| 263 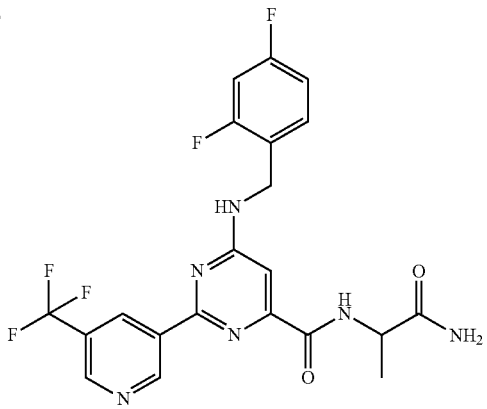 [SMILES: CC(NC(=O)c1cc(NCc2ccc(F)cc2F)nc(-c2cncc(C(F)(F)F)c2)n1)C(N)=O] | 6-(2,4-Difluoro-benzylamino)-2-(5-trifluoromethyl-pyridin-3-yl)-pyrimidine-4-carboxylic acid (1-carbamoyl-ethyl)-amide | A | 4.441 481.2 | 1H NMR: (400 MHz, DMSO-d6): δ 9.92 (s, 1H), 9.17 (d, J = 6.0 Hz, 1H), 9.10 (s, 1H), 8.97 (s, 1H), 8.60 (t, J = 5.6 Hz, 1H), 7.51-7.45 (m, J = 8.8 Hz, 1H), 7.39 (s, 1H), 7.24 (m, J = 4.0 Hz, 1H), 7.20-7.18 (m, 1H), 7.04 (t, J = 9.1 Hz, 1H), 6.88 (s, 1H), 4.71 (d, J = 5.6 Hz, 2H), 3.31 (s, 2H), 2.38 (t, J = 8.0 Hz, 2H). LCMS: (Method A) 481.0 (M + H), RT. 4.65 min, 95.7% (Max), 98.0% (254 nm) HPLC: (Method A) RT 4.44 min, 97.4% (Max), 97.4% (254 nm). |
| 264 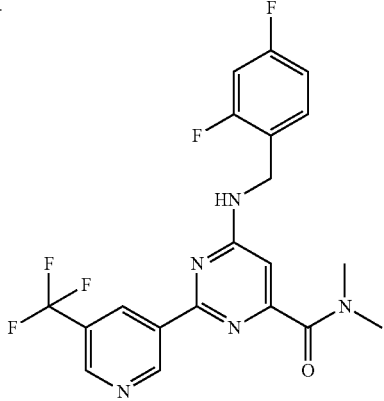 | 6-(2,4-Difluoro-benzylamino)-2-(5-trifluoromethyl-pyridin-3-yl)-pyrimidine-4-carboxylic acid dimethylamide | A | 4.796 438 | 1H NMR: (400 MHz, DMSO-d6): δ 9.65 (d, J = 1.6 Hz, 1H), 9.09 (d, J = 1.4 Hz, 1H), 8.75 (s, 1H), 8.46 (d, J = 6.0 Hz, 1H), 7.54-7.48 (m, 1H), 7.26-7.21 (m, 1H), 7.07-7.03 (m, 1H), 6.65 (s, 1H), 4.70 (d, J = 5.3 Hz, 2H), 2.99 (s, 6H). LCMS: (Method A) 481.0 (M + H), RT. 4.79 min, 95.7% (Max), 98.0% (254 nm). HPLC: (Method A) RT 4.44 min, 97.4% (Max), 97.4% (254 nm). |
| 265 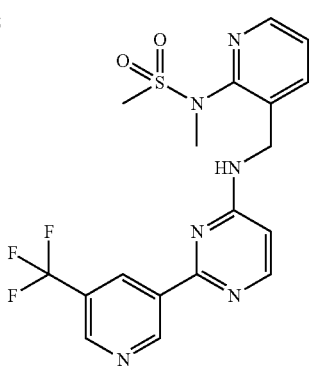 [SMILES: CN(c1ncccc1CNc1ccnc(-c2cncc(C(F)(F)F)c2)n1)S(C)(=O)=O] | N-Methyl-N-(3-{[2-(5-trifluoromethyl-pyridin-3-yl)-pyrimidin-4-ylamino]-methyl}-pyridin-2-yl)-methanesulfonamide | C | 3.073 439 | 1H NMR: (400 MHz, DMSO-d6): δ 9.58 (s, 1H), 9.04 (s, 1H), 8.67 (s, 1H), 8.43 (d, J = 3.2 Hz, 1H), 8.27 (d, J = 7.6 Hz, 2H), 7.81 (d, J = 7.1 Hz, 1H), 7.42-7.39 (m, 1H), 6.67 (s, 1H), 4.83 (s, 2H), 3.19 (s, 3H), 3.13 (s, 1H). LCMS: (Method A) 439.0 (M + H), RT. 2.91 min, 94.5% (Max), 96.9% (254 nm) HPLC: (Method A) RT 3.07 min, 96.4% (Max), 97.0% (254 nm). |

TABLE 5-continued

| Structure | Chemical Name | FAK IC50 | RT [Min] [M + H+] | |
|---|---|---|---|---|
| 266 | [2,6-Bis-(5-trifluoromethyl-pyridin-3-yl)-pyrimidin-4-yl]-(2,4-difluoro-benzyl)-amine | C | 6.067 512 | 1H NMR: (400 MHz, DMSO-d6): δ 9.8 (s, 1H), 9.6 (s, 1H), 9.1 (s, 1H), 8.9 (s, 1H), 8.90-8.80 (m, 1H), 8.4 (s, 1H), 7.54-7.48 (m, 1H), 7.25-7.21 (m, 2H), 7.07-7.03 (m, 1H), 4.7 (s, 1H). LCMS: (Method A) 512.0 (M + H), RT. 4.64 min, 96.4% (Max), 96.5% (254 nm). HPLC: (Method A) RT 6.07 min, 97.5% (Max), 95.9% (254 nm). |
| 267 | [1-(2-Fluoro-phenyl)-ethyl]-[2-(5-trifluoromethyl-pyridin-3-yl)-pyrimidin-4-yl]-amine | B | 3.934 363 | 1H NMR: (400 MHz, DMSO-d6): δ 9.51 (s, 1H), 9.02 (s, 1H), 8.72 (s, 1H), 8.32 (d, J = 4.0 Hz, 1H), 8.22 (d, J = 4.0 Hz, 1H), 7.43-7.39 (m, 1H), 7.21 (d, J = 4.0 Hz, 1H), 7.16-7.11 (m, 1H), 6.61 (d, J = 4.0 Hz, 1H), 5.51 (d, J = 4.0 Hz, 1H), 1.52 (s, 3H). LCMS: (Method A) 363.0 (M + H), RT. 3.86 min, 99.5% (Max), 99.6% (254 nm). HPLC: (Method A) RT 3.93 min, 99.7% (Max), 99.8% (254 nm). |
| 268 | N-Methyl-2-phenyl-2-[2-(5-trifluoromethyl-pyridin-3-yl)-pyrimidin-4-ylamino]-acetamide | C | 3.195 388 | 1H NMR: (400 MHz, DMSO-d6): δ 9.71 (d, J = 4.0 Hz, 1H), 9.12 (d, J = 4.0 Hz, 1H), 8.81 (s, 1H), 8.41-8.23 (m, 3H), 7.61 (t, J = 4.0 Hz, 2H), 7.37-7.26 (m, 2H), 6.81 (d, J = 4.0 Hz, 1H), 5.71 (d, J = 4.0 Hz, 1H), 2.61 (s, 3H). LCMS: (Method A) 388.0 (M + H), RT. 3.20 min, 98.0% (Max), 99.1% (254 nm). HPLC: (Method A) RT 3.20 min, 97.6% (Max), 99.2% (254 nm). |

TABLE 5-continued

| Structure | Chemical Name | FAK IC50 | RT [Min] [M + H+] | |
|---|---|---|---|---|
| 269 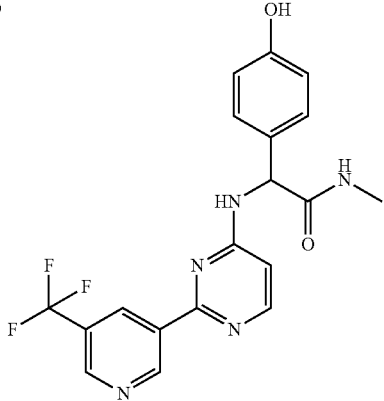 | 2-(4-Hydroxy-phenyl)-N-methyl-2-[2-(5-trifluoromethyl-pyridin-3-yl)-pyrimidin-4-ylamino]-acetamide | D | 2.551 404.3 | 1H NMR: (400 MHz, DMSO-d6): δ 9.71 (d, J = 4.0 Hz, 1H), 9.12 (d, J = 4.0 Hz, 1H), 8.81 (s, 1H), 8.41-8.23 (m, 3H), 7.61 (t, J = 4.0 Hz, 2H), 7.37-7.26 (m, 2H), 6.81 (d, J = 4.0 Hz, 1H), 5.71 (d, J = 4.0 Hz, 1H), 2.61 (s, 3H). LCMS: (Method A) 388.0 (M + H), RT. 3.20 min, 98.0% (Max), 99.1% (254 nm). HPLC: (Method A) RT 3.20 min, 97.6% (Max), 99.2% (254 nm). |
| 270 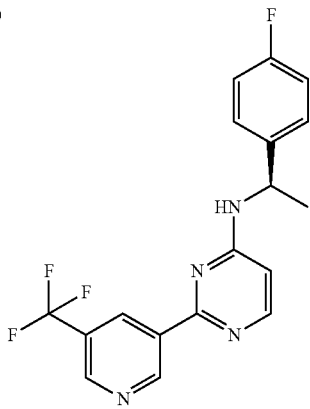 | [(R)-1-(4-Fluoro-phenyl)-ethyl]-[2-(5-trifluoromethyl-pyridin-3-yl)-pyrimidin-4-yl]-amine | B | 3.94 363 | |
| 271 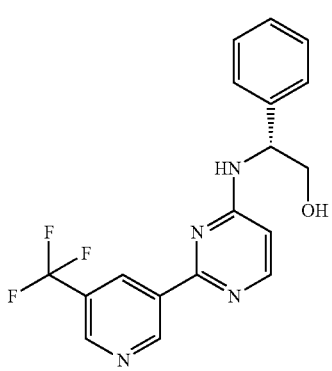 [SMILES: OC[C@H](Nc1ccnc(-c2cncc(C(F)(F)F)c2)n1)c1ccccc1] | (R)-2-Phenyl-2-[2-(5-trifluoromethyl-pyridin-3-yl)-pyrimidin-4-ylamino]-ethanol | B | 3.24 361 | |
| 272 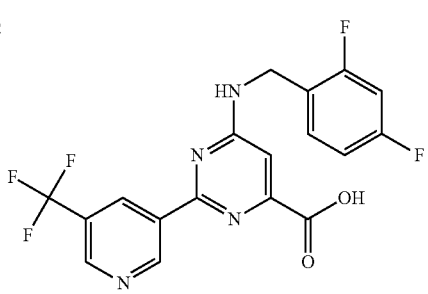 | 6-(2,4-Difluoro-benzylamino)-2-(5-trifluoromethyl-pyridin-3-yl)-pyrimidine-4-carboxylic acid | B | 4.46 411 | 1H NMR (400 MHz, DMSO-d6): δ 9.72 (d, J = 1.6 Hz, 1H), 9.08 (d, J = 1.40 Hz, 1H), 8.89 (s, 1H), 8.58 (s, 1H), 7.53-7.47 (m, 1H), 7.27-7.21 (m, 1H), 7.15 (s, 1H), 7.07-7.03 (m, 1H), 4.71 (d, J = 5.00 Hz, 2H). |

TABLE 5-continued

| Structure | Chemical Name | FAK IC50 | RT [Min] [M + H+] | |
|---|---|---|---|---|
| 273 | 6-(2,4-Difluoro-benzylamino)-2-(5-trifluoromethyl-pyridin-3-yl)-pyrimidine-4-carboxylic acid methyl ester | B | 5.08 425 | 1H NMR (400 MHz, DMSO-d6): δ 9.67 (d, J = 1.52 Hz, 1H), 9.10 (d, J = 1.32 Hz, 1H), 8.77 (s, 1H), 8.66 (t, J = 5.72 Hz, 1H), 7.54-7.48 (m, 1H), 7.27-7.20 (m, 2H), 7.07-7.04 (m, 1H), 4.71 (d, J = 5.48 Hz, 2H), 3.89 (s, 3H). |

The invention claimed is:
1. A compound of Formula (V)

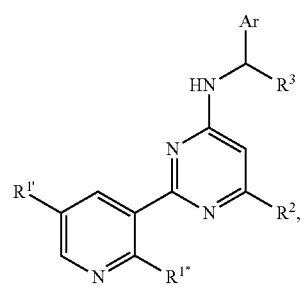

(V)

or its stereoisomers or tautomers, or pharmaceutically acceptable salts of each of the foregoing, wherein
$R^{1\prime}$, $R^{1\prime\prime\prime}$ are each independently H, A, Hal, Cyc, or CO(Cyc),
$R^2$ is H, or $Q^1$-$(C(LA)H)_n$-$Q^2$,
$R^3$ is H, A, or -LA-Cyc
A is unbranched or branched linear or cyclic alkyl having 1, 2, 3, 4 or 5 C atoms, in which one $CH_2$ group may be replaced by an O or S atom and/or by an —NH—, —CO—, —NHCOO—, —NHCONH—, —CONH—, —NHCO—, —CH═CH—, —N═CH— or —CH═N— group, and in which 1-5 H atoms may be replaced by Hal, and in which one CH group may be replaced by N, and in which one $CH_3$ group may be replaced by CN,
Hal is F, Cl, Br or I,
Cyc is a monocyclic, non-aromatic or aromatic, homo- or heterocycle having 0, 1 or 2, N, O and/or S atoms and 4, 5 or 6 skeleton atoms, which is independently of one another, mono- or disubstituted by Hal, LA, OH, carbonyl oxygen, SH, O(LA), NH$_2$, NH(LA), N(LA)$_2$, NO$_2$, CN, OCN, SCN, COOH, COO(LA), CONH$_2$, CONH(LA), CON(LA)$_2$, NHCO(LA), NHCONH(LA), NHCONH$_2$, NHSO$_2$(LA), CHO, CO(LA), SO$_2$NH$_2$, SO$_2$(LA) and/or SO$_2$Hal, Q$^1$ is —NH—, —O—, —COO—, —CONH—, or a bond,
Q$^2$ is NH$_2$, NH(LA), N(LA)$_2$, CONH$_2$, CONH(LA), CON(LA)$_2$, COOH, COO(LA), Cyc, or CO(Cyc),
n is 0, 1, 2, 3 or 4,
Ar is a mono- or bicyclic aromatic homo- or heterocycle having 0, 1, 2, 3 or 4 N, O and/or S atoms and 5, 6, 7, 8, 9, or 10 skeleton atoms, which is independently of one another, mono-, di- or trisubstituted by Hal, A, OH, SH, OA, NH$_2$, NHA, NA$_2$, NO$_2$, CN, OCN, SCN, COOH, CONH$_2$, CONHA, CONA$_2$, NHCOA, NHCONHA, NHCONH$_2$, NHSO$_2$A, CHO, COA, SO$_2$NH$_2$, SO$_2$A, SO$_2$Hal and/or (X)$_m$,-Cyc,
and in which a ring N-atom may be substituted by an O-atom to form an N-oxide group,
and in which in the case of a bicyclic ring system one ring may be aromatic, and the other ring non-aromatic,
X is CH$_2$, NH, or O,
m is 0 or 1,and
LA is H, or unbranched or branched linear alkyl having 1, 2 or 3 or 4 C atoms, wherein 1, 2 or 3 H atoms may be replaced by Hal.

2. A compound according to claim 1, wherein:
Ar is phenyl, pyridyl, 2,1,3-benzothiadiazolyl, 1,3-benzodioxolyl, pyrazolo[1,5-a]pyridyl, pyrimidyl, morpholinyl, 2,3-dihydro-benzofuranyl, or pyrazolyl, all of which may be unsubstituted, or mono- or disubstituted by Hal, LA, OH, SH, O(LA), NH$_2$, NH(LA), N(LA)$_2$, NO$_2$, CN, OCN, SCN, COOH, CONH$_2$, CONH(LA), CON(LA)$_2$, NHCO(LA), NHCONH(LA), NHCONH$_2$, NHSO$_2$(LA), CHO, CO(LA), SO$_2$NH$_2$, S$_{02}$(LA), SO$_2$Hal, or (X)$_m$-Cyc, or its stereoisomers or tautomers, or pharmaceutically acceptable salts of each of the foregoing.

3. A compound according to claim 1, wherein the compound is selected from the group consisting of:
6-(2,4-Difluoro-benzylamino)-2-(5-trifluoromethyl-pyridin-3-yl)-pyrimidine-4-carboxylic acid carbamoylmethyl-amide,
[2-(2-Amino-5-chloro-pyridin-3-yl)-pyrimidin-4-yl]-(4-fluoro-2-trifluoromethyl-benzyl)-amine,
[2-(2-Amino-5-trifluoromethyl-pyridin-3-yl)-pyrimidin-4-yl]-(2-trifluoromethyl-benzyl)-amine,
1-[6-(2,4-Difluoro-benzylamino)-2-(5-trifluoromethyl-pyridin-3-yl)-pyrimidine-4-carbonyl]-piperidine-3-carboxylic acid amide,
[2-(5-Chloro-pyridin-3-yl)-pyrimidin-4-yl]-(4-fluoro-2-trifluoromethyl-benzyl)-amine,
(4-Chloro-2-fluoro-benzyl)-[2-(5-chloro-pyridin-3-yl)-pyrimidin-4-yl]-amine,
6-(2,4-Difluoro-benzylamino)-2-(5-trifluoromethyl-pyridin-3-yl)-pyrimidine-4-carboxylic acid (2-carbamoyl-ethyl)-amide,
(4-Fluoro-2-trifluoromethyl-benzyl)-[2-(5-trifluoromethyl-pyridin-3-yl)-pyrimidin-4-yl]-amine,
[2-(5-Chloro-pyridin-3-yl)-pyrimidin-4-yl]-(2,4-difluoro-benzyl)-amine,
6-(2,4-Difluoro-benzylamino)-2-(5-trifluoromethyl-pyridin-3-yl)-pyrimidine-4-carboxylic acid (2-acetylamino-ethyl)-amide,
6-(2,4-Difluoro-benzylamino)-2-(5-trifluoromethyl-pyridin-3-yl)-pyrimidine-4-carboxylic acid (3-morpholin-4-yl-3-oxo-propyl)-amide,
6-(2,4-Difluoro-benzylamino)-2-(5-trifluoromethyl-pyridin-3-yl)-pyrimidine-4-carboxylic acid (3-morpholin-4-yl-propyl)-amide,
6-(2,4-Difluoro-benzylamino)-2-(5-trifluoromethyl-pyridin-3-yl)-pyrimidine-4-carboxylic acid (2-pyridin-3-yl-ethyl)-amide,
6-(2,4-Difluoro-benzylamino)-2-(5-trifluoromethyl-pyridin-3-yl)-pyrimidine-4-carboxylic acid (3-dimethylamino-propyl)-amide,
[2-(5-Chloro-pyridin-3-yl)-pyrimidin-4-yl]-(4-chloro-2-trifluoromethyl-benzyl)-amine,
6-(2,4-Difluoro-benzylamino)-2-(5-trifluoromethyl-pyridin-3-yl)-pyrimidine-4-carboxylic acid (1-methyl-pyrrolidin-3-ylmethyl)-amide,
6-(2,4-Difluoro-benzylamino)-2-(5-trifluoromethyl-pyridin-3-yl)-pyrimidine-4-carboxylic acid (4-dimethylamino-butyl)-amide,
6-(2,4-Difluoro-benzylamino)-2-(5-trifluoromethyl-pyridin-3-yl)-pyrimidine-4-carboxylic acid (2-dimethylamino-ethyl)-amide,
(4-Chloro-2-fluoro-benzyl)-[2-(5-trifluoromethyl-pyridin-3-yl)-pyrimidin-4-yl]-amine,
1-[6-(2,4-Difluoro-benzylamino)-2-(5-trifluoromethyl-pyridin-3-yl)-pyrimidine-4-carbonyl]-piperidine-4-carboxylic acid amide,
6-(2,4-Difluoro-benzylamino)-2-(5-trifluoromethyl-pyridin-3-yl)-pyrimidine-4-carboxylic acid dimethylamide,
6-(2,4-Difluoro-benzylamino)-2-(5-trifluoromethyl-pyridin-3-yl)-pyrimidine-4-carboxylic acid (1-carbamoyl-ethyl)-amide,
[6-(2,4-Difluoro-benzylamino)-2-(5-trifluoromethyl-pyridin-3-yl)-pyrimidin-4-yl]-morpholin-4-yl-methanone,
(2,4-Difluoro-benzyl)-[4-(5-trifluoromethyl-pyridin-3-yl)-pyrimidin-2-yl]-amine,
(4-Fluoro-2-trifluoromethyl-benzyl)-[4-(5-trifluoromethyl-pyridin-3-yl)-pyrimidin-2-yl]-amine,
(2,4-Difluoro-benzyl)-(5'-trifluoromethyl-[2,3']bipyridinyl-6-yl)-amine,
(2,4-Difluoro-benzyl)-[2-(5-methoxy-pyridin-3-yl)-pyrimidin-4-yl]-amine,
(3,5-Difluoro-pyridin-2-ylmethyl)-[2-(5-trifluoromethyl-pyridin-3-yl)-pyrimidin-4-yl]-amine, and
(4-Fluoro-2-trifluoromethyl-benzyl)-[2-(5-methoxy-pyridin-3-yl)-pyrimidin-4-yl]-amine,
or its stereoisomers or tautomers, or pharmaceutically acceptable salts of each of the foregoing.

4. A pharmaceutical composition comprising a compound of claim 1, or its stereoisomers or tautomers, or pharmaceutically acceptable salts of each of the foregoing, as active ingredient, together with a pharmaceutically acceptable carrier.

5. A kit consisting of separate packs of
a) an effective amount of a compound of claim 1, or its stereoisomers or tautomers, or pharmaceutically acceptable salts of each of the foregoing, and
b) an effective amount of a further medicament active ingredient.

6. Process for the manufacture of compounds of Formula (V) according to claim 1,
wherein a substituted pyrimidine according to Formula (X)

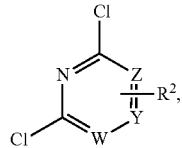

(X)

Wherein $R^2$ is H, or $Q^1$-$(C(LA)H)_n$-$Q^2$, and W is N,
is reacted with an aryl amine according to Formula (IX)

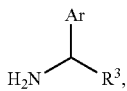

(IX)

Wherein
$R^3$ is H, A, or -LA-Cyc
Ar is a mono- or bicyclic aromatic homo- or heterocycle having 0, 1, 2, 3 or 4 N, O and/or S atoms and 5, 6, 7, 8, 9, or 10 skeleton atoms, which is independently of one another, mono-, di- or trisubstituted by Hal, A, OH, SH, OA, $NH_2$, NHA, $NA_2$, $NO_2$, CN, OCN, SCN, COOH, $CONH_2$, CONHA, $CONA_2$, NHCOA, NHCONHA, $NHCONH_2$, $NHSO_2A$, CHO, COA, $SO_2NH_2$, $SO_2A$, $SO_2Hal$ and/or $(X)_{m-Cyc}$,
and in which a ring N-atom may be substituted by an O-atom to form an N-oxide group,
and in which in the case of a bicyclic ring system one ring may be aromatic, and the other ring non-aromatic,
to yield an intermediate according to Formula (VIII)

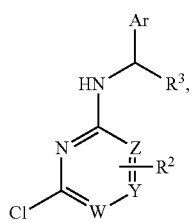

(VIII)

which is then reacted with a boronic acid or ester substituted pyridine according to Formula (VII)

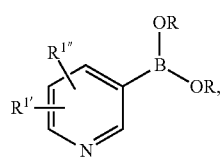

(VII)

Wherein $R^{1'}$, $R^{1'''}$ are each independently H, A, Hal, Cyc, or CO(Cyc), to yield a product according to Formula (V),

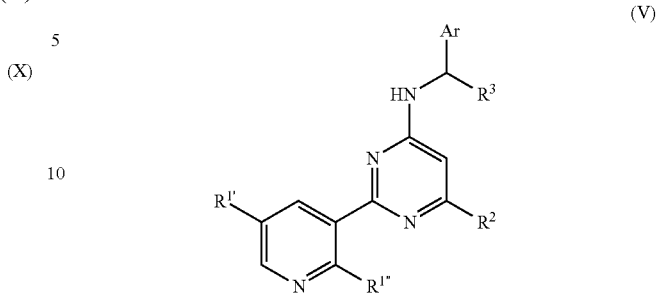

(V)

wherein R is H, LA, or an alkyl chain, linking the boronic acid oxygen atoms, and all other substituents have the meaning as defined for Formula (V) according to claim 1.

7. The compound of claim 1, wherein
Ar is phenyl or pyridyl, which is, independently, mono- or disubstituted in ortho and/or para position by Hal, LA, OH, O(LA), $NH_2$, NH(LA), $N(LA)_2$, $NHSO_2(LA)$, CO(LA), $SO_2NH_2$, $SO_2(LA)$, or $SO_2Hal$,
$R^{1'}$ is H, Hal, LA, O(LA), or CO(Cyc),
$R^{1'''}$ is H, or $NH_2$,
$R^2$ is H, and
$R^3$ is H.

8. The compound of claim 1, wherein
$R^{1'}$ is H, Hal, LA, O(LA), or CO(Cyc),
$R^{1'''}$ is H, or $NH_2$, and
$R^2$ is $Q^1$-$(CH_2)_n$-$Q^2$.

9. The compound of claim 1, wherein
$R^{1'}$ is H, Hal, LA, O(LA), or CO(Cyc),
$R^{1'''}$ is H, or $NH_2$,
$R^2$ is $Q^1$-$(CH_2)_n$-$Q^2$, and
$R^3$ is H.

10. The compound of claim 1, wherein
Ar is phenyl or pyridyl, which is, independently, mono- or disubstituted in ortho and/or para position by Hal, LA, OH, O(LA), $NH_2$, NH(LA), $N(LA)_2$, $NHSO_2(LA)$, CO(LA), $SO_2NH_2$, $S_{02}(LA)$, or $SO_2Hal$,
$R^{1'}$ is H, Hal, LA, O(LA), or CO(Cyc),
$R^{1'''}$ is H, or $NH_2$,
$R^2$ is $Q^1$-$(CH_2)_n$-$Q^2$, and
$R^3$ is H.

11. The compound of claim 1, wherein
Ar is phenyl which is disubstituted in ortho and para position by F,
$R^{1'}$ is $CF_3$,
$R^{1'''}$ is H,
$R^2$ is $Q^1$-$(CH_2)_n$-$Q^2$, and
$R^3$ is H.

12. The compound of claim 1, wherein $R^3$ is H.
13. The compound of claim 1, wherein
$R^{1'}$ is H, Hal, LA, O(LA), or CO(Cyc), and
$R^{1'''}$ is H, or $NH_2$.
14. The compound of claim 1, wherein $R^2$ is H.
15. The compound of claim 1, wherein $R^2$ is $Q^1$-$(C(LA)H)_n$-$Q^2$.
16. The compound of claim 1, wherein Ar is phenyl which is, independently, mono- or disubstituted by Hal, LA, OH, SH, O(LA), $NH_2$, NH(LA), $N(LA)_2$, $NO_2$, CN, OCN, SCN, COOH, $CONH_2$, CONH(LA), $CON(LA)_2$, NHCO(LA), NHCONH(LA), $NHCONH_2$, $NHSO_2(LA)$, CHO, CO(LA), $SO_2NH_2$, $SO_2(LA)$, $SO_2Hal$, Cyc, or O-Cyc.

17. The compound of claim 1, wherein Ar is phenyl or pyridyl, which is, independently, mono- or disubstituted in ortho and/or para position by Hal, LA, OH, O(LA), $NH_2$, NH(LA), $N(LA)_2$, $NHSO_2(LA)$, CO(LA), $SO_2NH_2$, $SO_2(LA)$, or $SO_2Hal$.

18. The compound of claim 1, wherein Ar is phenyl which is, independently, mono- or disubstituted in ortho and/or para position by F, Cl, methyl, or $CF_3$.

19. The compound of claim 1, wherein $R^2$ is H, and $R^3$ is H.

20. The compound of claim 1, wherein
$R^{1'}$ is H, Hal, LA, O(LA), or CO(Cyc),
$R^{1''}$ is H, or $NH_2$,
$R^2$ is H, and
$R^3$ is H.

21. The compound of claim 1, wherein $R^2$ is $Q^1$-$(CH_2)_n$-$Q^2$.

\* \* \* \* \*

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term FITC; C-term CONH2

<400> SEQUENCE: 1

Lys Gly Trp Met Glu Asp Tyr Asp Tyr Val His Leu Gln Gly Lys Lys
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ala Thr Gln Ser Phe Ile Ile Arg
1               5
```